(12) United States Patent
McCall et al.

(10) Patent No.: US 7,256,263 B2
(45) Date of Patent: Aug. 14, 2007

(54) DERMATOPHAGOIDES PROTEINS AND USES THEREOF

(75) Inventors: Catherine A. McCall, Boulder, CO (US); Shirley Wu Hunter, Fort Collins, CO (US); Eric R. Weber, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 571 days.

(21) Appl. No.: 10/218,743

(22) Filed: Aug. 13, 2002

(65) Prior Publication Data

US 2003/0096779 A1 May 22, 2003

Related U.S. Application Data

(62) Division of application No. 09/292,225, filed on Apr. 15, 1999, now Pat. No. 6,455,686.

(51) Int. Cl.
*A61K 38/00* (2006.01)
*C07K 1/00* (2006.01)
*C07K 14/00* (2006.01)

(52) U.S. Cl. ...................... 530/350; 530/300
(58) Field of Classification Search ............... 530/350, 530/300
See application file for complete search history.

(56) References Cited

U.S. PATENT DOCUMENTS

| 5,314,991 | A | 5/1994 | Oka et al. | 530/350 |
|---|---|---|---|---|
| 5,405,758 | A | 4/1995 | Oka et al. | 435/69.3 |
| 5,433,948 | A | 7/1995 | Thomas et al. | 424/185.1 |
| 5,460,977 | A | 10/1995 | Ando et al. | 436/513 |
| 5,496,554 | A | 3/1996 | Oka et al. | 424/276.1 |
| 5,552,142 | A | 9/1996 | Thomas et al. | 424/185.1 |
| 5,770,202 | A | 6/1998 | Thomas et al. | 424/185.1 |
| 5,773,002 | A | 6/1998 | Thomas et al. | 424/184.1 |
| 6,455,686 | B1 * | 9/2002 | McCall et al. | 536/23.4 |

FOREIGN PATENT DOCUMENTS

| EP | 0 473 111 A2 | 3/1992 |
|---|---|---|
| EP | 0 498 124 A1 | 8/1992 |
| JP | 07133227 | 5/1995 |
| WO | WO94/27634 | 12/1994 |

OTHER PUBLICATIONS

Kramer KJ et al. Insect Biochem Mol Biol Sep. 1993;23(6):691-701, Sequence of a cDNA and expression of the gene encoding epidermal and gut chitinases of Manduca sexta.*
Accession No. A56596, in particular 138-149 which matches 152-163 SEQ ID No. 35.*
Aki et al., GenBank Submission Accession No. D17676, Sep. 20, 1993.
Aki et al., GenBank Submission Accession No. 666007, Sep. 20, 1993.
Aki et al., *J. Biochem*, vol. 115, 1994, pp. 435-440.
Chapman et al., *Allergy*, vol. 52, 1997, pp. 374-379.
Esch et al., *13th Proceedings of AAVD/ACVD Meeting*, 1997, pp. 87-88.
Fashandi et al., "Presence of a 97 KDa Allergen in Mite, *Dermatophagoides farinae*," Abstract 509.
Fujikawa et al., *Molecular Immunology*, vol. 33, No. 3, 1996, pp. 311-319.
Kwochka et al., "A New Approach to Immunotherapy for Flea Allergy Dermatitis in Dogs: Flee Salivary Antigen Rush Immunotherapy," BSAVA Abstract, __.
Le Mao et al., *J. Allergy Clin. Immunol.*, 1998, pp. 631-636.
Marshall et al., *Nature Biotechnology*, vol. 15, 1997, pp. 718-719.
Nishioka et al., *Acta Med Okayama*, vol. 48(5), 1994, pp. 279-282.
Noli et al., *Veterinary Immunology and Immunopathology*, vol. 52, 1996, pp. 147-157.
Stewart et al., *Clinical Allergy*, vol. 10, 1980, pp. 617-630, XP-002113315.
Stewart et al., *Aust. J. Exp. Biol. Med. Sci.*, vol. 58, No. 3, 1980, pp. 275-288, No. XP-002113316.
Takai et al., *Nature Biotechnology*, vol. 15, 1997, pp. 754-758.
Tsai et al., *J. Allergy Clin. Immunol.*, vol. 102(2), 1998, pp. 295-303.

* cited by examiner

Primary Examiner—Shin-Lin Chen

(57) ABSTRACT

The present invention relates to high molecular weight *Dermatophagoides* proteins, nucleic acid molecules encoding such proteins, and therapeutic and diagnostic reagents derived from such proteins.

5 Claims, 2 Drawing Sheets

SEQUENCE LISTING

<160> NUMBER OF SEQ ID NOS: 49

<210> SEQ ID NO 1
<211> LENGTH: 14
<212> TYPE: PRT
<213> ORGANISM: Dermatophagoides farinae

<400> SEQUENCE: 1

Ser Ile Lys Arg Asp His Asn Asp Tyr Ser Lys Asn Pro Met
 1               5                  10

<210> SEQ ID NO 2
<211> LENGTH: 20
<212> TYPE: PRT
<213> ORGANISM: Dermatophagoides farinae

<400> SEQUENCE: 2

Asp Tyr Glu Tyr Pro Gly Ser Arg Leu Gly Asn Pro Lys Ala Pro Leu
 1               5                  10                  15

Tyr Lys Arg Pro
            20

<210> SEQ ID NO 3
<211> LENGTH: 20
<212> TYPE: PRT

<213> ORGANISM: Dermatophagoides farinae

<400> SEQUENCE: 3

Asp Ile Pro His Pro Thr Asn Ile His Lys Tyr Leu Val Cys Glu Ser
1               5                   10                  15

Val Asn Gly Gly
            20

<210> SEQ ID NO 4
<211> LENGTH: 20
<212> TYPE: PRT
<213> ORGANISM: Dermatophagoides farinae

<400> SEQUENCE: 4

Asp Pro Ala Lys Gly Met Ser Pro Pro Gly Phe Ile Val Gly Glu Glu
1               5                   10                  15

Gly Val Leu Ser
            20

<210> SEQ ID NO 5
<211> LENGTH: 12
<212> TYPE: PRT
<213> ORGANISM: Dermatophagoides farinae

<400> SEQUENCE: 5

Asp Glu Lys Asn Ser Phe Glu Cys Ile Leu Gly Pro
1               5                   10

<210> SEQ ID NO 6
<211> LENGTH: 18
<212> TYPE: PRT
<213> ORGANISM: Dermatophagoides farinae

<400> SEQUENCE: 6

Asp Ala Phe Glu Pro His Gly Tyr Leu Leu Thr Ala Ala Val Ser Pro
1               5                   10                  15

Gly Lys

<210> SEQ ID NO 7
<211> LENGTH: 13
<212> TYPE: PRT
<213> ORGANISM: Dermatophagoides farinae

<400> SEQUENCE: 7

Asp Lys Gln Asn Tyr Leu Ala Leu Val Arg Glu Leu Lys
1               5                   10

<210> SEQ ID NO 8
<211> LENGTH: 24
<212> TYPE: PRT
<213> ORGANISM: Dermatophagoides farinae

<400> SEQUENCE: 8

Asp Met Ala Gln Asn Tyr Lys Tyr Arg Gln Gln Phe Ile Gln Ser Val
1               5                   10                  15

Leu Asn Asn Gly Ala Thr Arg Gln
            20

<210> SEQ ID NO 9
<211> LENGTH: 23
<212> TYPE: PRT
<213> ORGANISM: Dermatophagoides farinae
<220> FEATURE:

-continued

<223> OTHER INFORMATION: At locations 3 and 7, Xaa = any amino acid

<400> SEQUENCE: 9

Asp Glu Xaa Asn Val Met Xaa Tyr Val Leu Tyr Thr Met His Tyr Tyr
 1               5                  10                  15

Leu Asn Asn Gly Ala Thr Arg
            20

<210> SEQ ID NO 10
<211> LENGTH: 17
<212> TYPE: PRT
<213> ORGANISM: Dermatophagoides farinae
<220> FEATURE:
<223> OTHER INFORMATION: At location 14, Xaa = any amino acid

<400> SEQUENCE: 10

Asp Lys Leu Val Met Gly Val Pro Phe Tyr Gly Arg Ala Xaa Ser Ile
 1               5                  10                  15

Glu

<210> SEQ ID NO 11
<211> LENGTH: 19
<212> TYPE: PRT
<213> ORGANISM: Dermatophagoides farinae

<400> SEQUENCE: 11

Asp Ile Pro His Pro Thr Asn Ile His Lys Tyr Leu Val Cys Glu Ser
 1               5                  10                  15

Val Asn Gly

<210> SEQ ID NO 12
<211> LENGTH: 18
<212> TYPE: PRT
<213> ORGANISM: Dermatophagoides farinae

<400> SEQUENCE: 12

Asp Tyr Ala Lys Asn Pro Lys Arg Ile Val Cys Ile Val Gly Thr Glu
 1               5                  10                  15

Gly Val

<210> SEQ ID NO 13
<211> LENGTH: 20
<212> TYPE: PRT
<213> ORGANISM: Dermatophagoides farinae

<400> SEQUENCE: 13

Asp Pro Ala Lys Gly Met Ser Pro Pro Gly Phe Ile Val Gly Glu Glu
 1               5                  10                  15

Gly Val Leu Ser
            20

<210> SEQ ID NO 14
<211> LENGTH: 1752
<212> TYPE: DNA
<213> ORGANISM: Dermatophagoides farinae
<220> FEATURE:
<221> NAME/KEY: CDS
<222> LOCATION: (1)..(1665)

<400> SEQUENCE: 14 atg aaa acc ata tat gca ata ctt agt att atg gcc tgc att ggc ctt      48
Met Lys Thr Ile Tyr Ala Ile Leu Ser Ile Met Ala Cys Ile Gly Leu
 1               5                  10                  15

-continued

| | |
|---|---|
| atg aat gca tcc atc aaa cga gat cat aat gat tat tcg aaa aat ccg<br>Met Asn Ala Ser Ile Lys Arg Asp His Asn Asp Tyr Ser Lys Asn Pro<br>20               25                  30 | 96 |
| atg aga att gtt tgt tat gtt gga aca tgg tcc gta tat cat aaa gtt<br>Met Arg Ile Val Cys Tyr Val Gly Thr Trp Ser Val Tyr His Lys Val<br>35               40                  45 | 144 |
| gat cca tac act atc gaa gat att gat cca ttc aag tgt aca cat tta<br>Asp Pro Tyr Thr Ile Glu Asp Ile Asp Pro Phe Lys Cys Thr His Leu<br>50               55                  60 | 192 |
| atg tat ggt ttc gct aaa att gat gaa tac aaa tac aca att caa gtt<br>Met Tyr Gly Phe Ala Lys Ile Asp Glu Tyr Lys Tyr Thr Ile Gln Val<br>65               70                  75                 80 | 240 |
| ttc gat cct tac caa gat gat aac cat aac tca tgg gaa aaa cgt ggt<br>Phe Asp Pro Tyr Gln Asp Asp Asn His Asn Ser Trp Glu Lys Arg Gly<br>85               90                  95 | 288 |
| tat gaa cgt ttc aac aac ttg cga ttg aag aat cca gaa tta acc acc<br>Tyr Glu Arg Phe Asn Asn Leu Arg Leu Lys Asn Pro Glu Leu Thr Thr<br>100             105             110 | 336 |
| atg att tca ctt ggt ggt tgg tat gaa ggc tcg gaa aaa tat tcc gat<br>Met Ile Ser Leu Gly Gly Trp Tyr Glu Gly Ser Glu Lys Tyr Ser Asp<br>115             120             125 | 384 |
| atg gct gca aat cca aca tat cgt caa caa ttc ata caa tca gtt ttg<br>Met Ala Ala Asn Pro Thr Tyr Arg Gln Gln Phe Ile Gln Ser Val Leu<br>130             135             140 | 432 |
| gac ttt ttg caa gaa tac aag ttc gac ggt cta gat ttg gat tgg gag<br>Asp Phe Leu Gln Glu Tyr Lys Phe Asp Gly Leu Asp Leu Asp Trp Glu<br>145             150             155             160 | 480 |
| tat cct gga tct cga ttg ggt aac ccg aaa atc gat aaa caa aac tat<br>Tyr Pro Gly Ser Arg Leu Gly Asn Pro Lys Ile Asp Lys Gln Asn Tyr<br>165             170             175 | 528 |
| ttg gct ttg gtt aga gaa ctt aaa gac gct ttt gaa cct cat ggc tac<br>Leu Ala Leu Val Arg Glu Leu Lys Asp Ala Phe Glu Pro His Gly Tyr<br>180             185             190 | 576 |
| ttg ttg act gct gca gta tca cca ggt aaa gac aaa atc gac cga gct<br>Leu Leu Thr Ala Ala Val Ser Pro Gly Lys Asp Lys Ile Asp Arg Ala<br>195             200             205 | 624 |
| tat gat atc aaa gaa ttg aac aaa ttg ttc gat tgg atg aat gtc atg<br>Tyr Asp Ile Lys Glu Leu Asn Lys Leu Phe Asp Trp Met Asn Val Met<br>210             215             220 | 672 |
| aca tat gat tac cac ggt gga tgg gaa aac ttt tac ggt cac aat gct<br>Thr Tyr Asp Tyr His Gly Gly Trp Glu Asn Phe Tyr Gly His Asn Ala<br>225             230             235             240 | 720 |
| ccg ttg tat aaa cga cca gat gaa act gat gag ttg cac act tac ttc<br>Pro Leu Tyr Lys Arg Pro Asp Glu Thr Asp Glu Leu His Thr Tyr Phe<br>245             250             255 | 768 |
| aat gtc aac tac acc atg cac tat tat ttg aac aat ggt gcc acc aga<br>Asn Val Asn Tyr Thr Met His Tyr Tyr Leu Asn Asn Gly Ala Thr Arg<br>260             265             270 | 816 |
| gac aaa ttg gta atg ggt gtt cca ttc tat ggc cgt gct tgg agc att<br>Asp Lys Leu Val Met Gly Val Pro Phe Tyr Gly Arg Ala Trp Ser Ile<br>275             280             285 | 864 |
| gaa gat cga agc aaa ctc aaa ctt gga gat cca gcc aaa ggc atg tcg<br>Glu Asp Arg Ser Lys Leu Lys Leu Gly Asp Pro Ala Lys Gly Met Ser<br>290             295             300 | 912 |
| ccc cca ggt ttc att tct ggt gaa gaa ggt gtc ctc tca tat ata gaa<br>Pro Pro Gly Phe Ile Ser Gly Glu Glu Gly Val Leu Ser Tyr Ile Glu<br>305             310             315             320 | 960 |
| ttg tgt caa ttg ttt caa aaa gaa gaa tgg cat atc caa tac gat gaa<br>Leu Cys Gln Leu Phe Gln Lys Glu Glu Trp His Ile Gln Tyr Asp Glu | 1008 |

```
                    325                 330                 335
tat tac aat gct cca tat ggt tac aat gat aaa atc tgg gtc ggt tac      1056
Tyr Tyr Asn Ala Pro Tyr Gly Tyr Asn Asp Lys Ile Trp Val Gly Tyr
            340                 345                 350 gat gat ctg gcc agt ata tca tgc aag ttg gct ttc ctg aaa gaa tta      1104
Asp Asp Leu Ala Ser Ile Ser Cys Lys Leu Ala Phe Leu Lys Glu Leu
            355                 360                 365 ggc gtt tct ggt gtc atg gtt tgg tca ttg gaa aat gat gat ttc aaa      1152
Gly Val Ser Gly Val Met Val Trp Ser Leu Glu Asn Asp Asp Phe Lys
            370                 375                 380 ggt cac tgc gga ccg aaa aat cca ttg ttg aac aaa gtt cat aat atg      1200
Gly His Cys Gly Pro Lys Asn Pro Leu Leu Asn Lys Val His Asn Met
385                 390                 395                 400 att aat ggc gat gaa aag aac tct ttc gaa tgc att ttg ggt cca agt      1248
Ile Asn Gly Asp Glu Lys Asn Ser Phe Glu Cys Ile Leu Gly Pro Ser
            405                 410                 415 aca acg aca cca act cca acg acg aca ccc aca acc ccg act aca acg      1296
Thr Thr Thr Pro Thr Pro Thr Thr Thr Pro Thr Thr Pro Thr Thr Thr
            420                 425                 430 cca aca act cct tct ccc acc acc ccg aca aca acc cct tct ccc acc      1344
Pro Thr Thr Pro Ser Pro Thr Thr Pro Thr Thr Thr Pro Ser Pro Thr
            435                 440                 445 acc ccg aca aca acc cct tct ccc acc aca ccg aca aca act cct tct      1392
Thr Pro Thr Thr Thr Pro Ser Pro Thr Thr Pro Thr Thr Thr Pro Ser
450                 455                 460 ccc acc aca cca aca cca aca aca cca aca cca gcc cct aca aca tcg      1440
Pro Thr Thr Pro Thr Pro Thr Thr Pro Thr Pro Ala Pro Thr Thr Ser
465                 470                 475                 480 aca cct tcg cca acc acg acc gaa cac aca agc gaa aca cca aaa tat      1488
Thr Pro Ser Pro Thr Thr Thr Glu His Thr Ser Glu Thr Pro Lys Tyr
            485                 490                 495 aca acc tat gtc gat gga cat ctt atc aaa tgt tac aag gaa ggt gat      1536
Thr Thr Tyr Val Asp Gly His Leu Ile Lys Cys Tyr Lys Glu Gly Asp
            500                 505                 510 atc cca cat cca acc aat ata cac aaa tat ttg gtc tgt gaa ttt gtt      1584
Ile Pro His Pro Thr Asn Ile His Lys Tyr Leu Val Cys Glu Phe Val
            515                 520                 525 aat ggt ggc tgg tgg gtt cat att atg ccc tgt cca ccg ggc act att      1632
Asn Gly Gly Trp Trp Val His Ile Met Pro Cys Pro Pro Gly Thr Ile
            530                 535                 540 tgg tgt caa gaa aaa ttg act tgt ata ggc gaa taattctgaa aaaaaaattc    1685
Trp Cys Gln Glu Lys Leu Thr Cys Ile Gly Glu
545                 550                 555 aattaaaatt taaaattcaa tttttaatat gaaaaattca aaaaaaaaaa aaaaaaaaa     1745 aaaaaaa                                                              1752

<210> SEQ ID NO 15
<211> LENGTH: 555
<212> TYPE: PRT
<213> ORGANISM: Dermatophagoides farinae

<400> SEQUENCE: 15

Met Lys Thr Ile Tyr Ala Ile Leu Ser Ile Met Ala Cys Ile Gly Leu
 1               5                  10                  15

Met Asn Ala Ser Ile Lys Arg Asp His Asn Asp Tyr Ser Lys Asn Pro
            20                  25                  30

Met Arg Ile Val Cys Tyr Val Gly Thr Trp Ser Val Tyr His Lys Val
        35                  40                  45
```

```
Asp Pro Tyr Thr Ile Glu Asp Ile Asp Pro Phe Lys Cys Thr His Leu
     50                  55                  60

Met Tyr Gly Phe Ala Lys Ile Asp Glu Tyr Lys Tyr Thr Ile Gln Val
 65                  70                  75                  80

Phe Asp Pro Tyr Gln Asp Asp Asn His Asn Ser Trp Glu Lys Arg Gly
             85                  90                  95

Tyr Glu Arg Phe Asn Asn Leu Arg Leu Lys Asn Pro Glu Leu Thr Thr
            100                 105                 110

Met Ile Ser Leu Gly Gly Trp Tyr Glu Gly Ser Glu Lys Tyr Ser Asp
            115                 120                 125

Met Ala Ala Asn Pro Thr Tyr Arg Gln Gln Phe Ile Gln Ser Val Leu
        130                 135                 140

Asp Phe Leu Gln Glu Tyr Lys Phe Asp Gly Leu Asp Leu Asp Trp Glu
145                 150                 155                 160

Tyr Pro Gly Ser Arg Leu Gly Asn Pro Lys Ile Asp Lys Gln Asn Tyr
                165                 170                 175

Leu Ala Leu Val Arg Glu Leu Lys Asp Ala Phe Glu Pro His Gly Tyr
            180                 185                 190

Leu Leu Thr Ala Ala Val Ser Pro Gly Lys Asp Lys Ile Asp Arg Ala
        195                 200                 205

Tyr Asp Ile Lys Glu Leu Asn Lys Leu Phe Asp Trp Met Asn Val Met
210                 215                 220

Thr Tyr Asp Tyr His Gly Gly Trp Glu Asn Phe Tyr Gly His Asn Ala
225                 230                 235                 240

Pro Leu Tyr Lys Arg Pro Asp Glu Thr Asp Glu Leu His Thr Tyr Phe
                245                 250                 255

Asn Val Asn Tyr Thr Met His Tyr Tyr Leu Asn Asn Gly Ala Thr Arg
            260                 265                 270

Asp Lys Leu Val Met Gly Val Pro Phe Tyr Gly Arg Ala Trp Ser Ile
        275                 280                 285

Glu Asp Arg Ser Lys Leu Lys Leu Gly Asp Pro Ala Lys Gly Met Ser
290                 295                 300

Pro Pro Gly Phe Ile Ser Gly Glu Glu Gly Val Leu Ser Tyr Ile Glu
305                 310                 315                 320

Leu Cys Gln Leu Phe Gln Lys Glu Glu Trp His Ile Gln Tyr Asp Glu
                325                 330                 335

Tyr Tyr Asn Ala Pro Tyr Gly Tyr Asn Asp Lys Ile Trp Val Gly Tyr
            340                 345                 350

Asp Asp Leu Ala Ser Ile Ser Cys Lys Leu Ala Phe Leu Lys Glu Leu
        355                 360                 365

Gly Val Ser Gly Val Met Val Trp Ser Leu Glu Asn Asp Asp Phe Lys
370                 375                 380

Gly His Cys Gly Pro Lys Asn Pro Leu Leu Asn Lys Val His Asn Met
385                 390                 395                 400

Ile Asn Gly Asp Glu Lys Asn Ser Phe Glu Cys Ile Leu Gly Pro Ser
                405                 410                 415

Thr Thr Thr Pro Thr Pro Thr Thr Pro Thr Thr Pro Thr Thr Thr Thr
            420                 425                 430

Pro Thr Thr Pro Ser Pro Thr Thr Pro Thr Thr Thr Pro Ser Pro Thr
        435                 440                 445

Thr Pro Thr Thr Thr Pro Ser Pro Thr Thr Pro Thr Thr Thr Pro Ser
450                 455                 460

Pro Thr Thr Pro Thr Pro Thr Thr Pro Thr Pro Ala Pro Thr Thr Ser
```

```
                465                 470                 475                 480
Thr Pro Ser Pro Thr Thr Thr Glu His Thr Ser Glu Thr Pro Lys Tyr
                    485                 490                 495
Thr Thr Tyr Val Asp Gly His Leu Ile Lys Cys Tyr Lys Glu Gly Asp
                500                 505                 510
Ile Pro His Pro Thr Asn Ile His Lys Tyr Leu Val Cys Glu Phe Val
            515                 520                 525
Asn Gly Gly Trp Trp Val His Ile Met Pro Cys Pro Gly Thr Ile
        530                 535                 540
Trp Cys Gln Glu Lys Leu Thr Cys Ile Gly Glu
545                 550                 555

<210> SEQ ID NO 16
<211> LENGTH: 1752
<212> TYPE: DNA
<213> ORGANISM: Dermatophagoides farinae

<400> SEQUENCE: 16
tttttttttt tttttttttt ttttttttga attttttcata ttaaaaattg aattttaaat      60
tttaattgaa ttttttttc  agaattattc gcctatacaa gtcaattttt cttgacacca     120
aatagtgccc ggtggacagg gcataatatg aacccaccag ccaccattaa caaattcaca     180
gaccaaatat ttgtgtatat tggttggatg tgggatatca ccttccttgt aacatttgat     240
aagatgtcca tcgacatagg ttgtatattt tggtgtttcg cttgtgtgtt cggtcgtggt     300
tggcgaaggt gtcgatgttg tagggctgg tgttggtgtt gttggtgttg gtgtggtggg     360
agaaggagtt gttgtcggtg tggtgggaga aggggttgtt gtcggggtgg tgggagaagg     420
ggttgttgtc ggggtggtgg gagaaggagt tgttggcgtt gtagtcgggg ttgtgggtgt     480
cgtcgttgga gttggtgtcg ttgtacttgg acccaaaatg cattcgaaag agttcttttc     540
atcgccatta atcatattat gaactttgtt caacaatgga ttttttcggtc cgcagtgacc     600
tttgaaatca tcattttcca atgaccaaac catgacacca gaaacgccta attctttcag     660
gaaagccaac ttgcatgata tactggccag atcatcgtaa ccgacccaga ttttatcatt     720
gtaaccatat ggagcattgt aatattcatc gtattggata tgccattctt cttttttgaaa     780
caattgacac aattctatat atgagaggac accttcttca ccagaaatga acctggggg     840
cgacatgcct ttggctggat ctccaagttt gagtttgctt cgatcttcaa tgctccaagc     900
acggccatag aatggaacac ccattaccaa tttgtctctg gtggcaccat tgttcaaata     960
atagtgcatg gtgtagttga cattgaagta agtgtgcaac tcatcagttt catctggtcg    1020
tttatacaac ggagcattgt gaccgtaaaa gttttcccat ccaccgtggt aatcatatgt    1080
catgacattc atccaatcga acaatttgtt caattctttg atatcataag ctcggtcgat    1140
tttgtcttta cctggtgata ctgcagcagt caacaagtag ccatgaggtt caaaagcgtc    1200
tttaagttct ctaaccaaag ccaaatagtt ttgtttatcg attttcgggt tacccaatcg    1260
agatccagga tactcccaat ccaaatctag accgtcgaac ttgtattctt gcaaaaagtc    1320
caaaactgat tgtatgaatt gttgacgata tgttggattt gcagccatat cggaatattt    1380
ttccgagcct tcataccaac caccaagtga atcatggtg  gttaattctg gattcttcaa    1440
tcgcaagttg ttgaaacgtt cataaccacg ttttcccat gagttatggt tatcatcttg     1500
gtaaggatcg aaaacttgaa ttgtgtattt gtattcatca attttagcga aaccatacat    1560
taaatgtgta cacttgaatg gatcaatatc ttcgatagtg tatggatcaa ctttatgata    1620
```

-continued

```
tacggaccat gttccaacat aacaaacaat tctcatcgga ttttcgaat aatcattatg    1680 atctcgtttg atggatgcat tcataaggcc aatgcaggcc ataatactaa gtattgcata    1740
tatggttttc at                                                        1752
```

<210> SEQ ID NO 17
<211> LENGTH: 1665
<212> TYPE: DNA
<213> ORGANISM: Dermatophagoides farinae
<220> FEATURE:
<221> NAME/KEY: CDS
<222> LOCATION: (1)..(1665)

<400> SEQUENCE: 17

```
atg aaa acc ata tat gca ata ctt agt att atg gcc tgc att ggc ctt      48
Met Lys Thr Ile Tyr Ala Ile Leu Ser Ile Met Ala Cys Ile Gly Leu
  1               5                  10                  15 atg aat gca tcc atc aaa cga gat cat aat gat tat tcg aaa aat ccg      96
Met Asn Ala Ser Ile Lys Arg Asp His Asn Asp Tyr Ser Lys Asn Pro
             20                  25                  30 atg aga att gtt tgt tat gtt gga aca tgg tcc gta tat cat aaa gtt     144
Met Arg Ile Val Cys Tyr Val Gly Thr Trp Ser Val Tyr His Lys Val
         35                  40                  45 gat cca tac act atc gaa gat att gat cca ttc aag tgt aca cat tta     192
Asp Pro Tyr Thr Ile Glu Asp Ile Asp Pro Phe Lys Cys Thr His Leu
     50                  55                  60 atg tat ggt ttc gct aaa att gat gaa tac aaa tac aca att caa gtt     240
Met Tyr Gly Phe Ala Lys Ile Asp Glu Tyr Lys Tyr Thr Ile Gln Val
 65                  70                  75                  80 ttc gat cct tac caa gat gat aac cat aac tca tgg gaa aaa cgt ggt     288
Phe Asp Pro Tyr Gln Asp Asp Asn His Asn Ser Trp Glu Lys Arg Gly
                 85                  90                  95 tat gaa cgt ttc aac aac ttg cga ttg aag aat cca gaa tta acc acc     336
Tyr Glu Arg Phe Asn Asn Leu Arg Leu Lys Asn Pro Glu Leu Thr Thr
            100                 105                 110 atg att tca ctt ggt ggt tgg tat gaa ggc tcg gaa aaa tat tcc gat     384
Met Ile Ser Leu Gly Gly Trp Tyr Glu Gly Ser Glu Lys Tyr Ser Asp
        115                 120                 125 atg gct gca aat cca aca tat cgt caa caa ttc ata caa tca gtt ttg     432
Met Ala Ala Asn Pro Thr Tyr Arg Gln Gln Phe Ile Gln Ser Val Leu
    130                 135                 140 gac ttt ttg caa gaa tac aag ttc gac ggt cta gat ttg gat tgg gag     480
Asp Phe Leu Gln Glu Tyr Lys Phe Asp Gly Leu Asp Leu Asp Trp Glu
145                 150                 155                 160 tat cct gga tct cga ttg ggt aac ccg aaa atc gat aaa caa aac tat     528
Tyr Pro Gly Ser Arg Leu Gly Asn Pro Lys Ile Asp Lys Gln Asn Tyr
                165                 170                 175 ttg gct ttg gtt aga gaa ctt aaa gac gct ttt gaa cct cat ggc tac     576
Leu Ala Leu Val Arg Glu Leu Lys Asp Ala Phe Glu Pro His Gly Tyr
            180                 185                 190 ttg ttg act gct gca gta tca cca ggt aaa gac aaa atc gac cga gct     624
Leu Leu Thr Ala Ala Val Ser Pro Gly Lys Asp Lys Ile Asp Arg Ala
        195                 200                 205 tat gat atc aaa gaa ttg aac aaa ttg ttc gat tgg atg aat gtc atg     672
Tyr Asp Ile Lys Glu Leu Asn Lys Leu Phe Asp Trp Met Asn Val Met
    210                 215                 220 aca tat gat tac cac ggt gga tgg gaa aac ttt tac ggt cac aat gct     720
Thr Tyr Asp Tyr His Gly Gly Trp Glu Asn Phe Tyr Gly His Asn Ala
225                 230                 235                 240 ccg ttg tat aaa cga cca gat gaa act gat gag ttg cac act tac ttc     768
Pro Leu Tyr Lys Arg Pro Asp Glu Thr Asp Glu Leu His Thr Tyr Phe
```

|     |     |     |     |     |     |     |     |     |     |     |     |     |     |     |     |
| --- | --- | --- | --- | --- | --- | --- | --- | --- | --- | --- | --- | --- | --- | --- | --- |
|  |  | 245 |  |  |  |  | 250 |  |  |  |  | 255 |  |  |  |
| aat | gtc | aac | tac | acc | atg | cac | tat | tat | ttg | aac | aat | ggt | gcc | acc | aga | 816 |
| Asn | Val | Asn | Tyr | Thr | Met | His | Tyr | Tyr | Leu | Asn | Asn | Gly | Ala | Thr | Arg |  |
|  |  | 260 |  |  |  |  | 265 |  |  |  |  | 270 |  |  |  |  |
| gac | aaa | ttg | gta | atg | ggt | gtt | cca | ttc | tat | ggc | cgt | gct | tgg | agc | att | 864 |
| Asp | Lys | Leu | Val | Met | Gly | Val | Pro | Phe | Tyr | Gly | Arg | Ala | Trp | Ser | Ile |  |
|  |  | 275 |  |  |  |  | 280 |  |  |  |  | 285 |  |  |  |  |
| gaa | gat | cga | agc | aaa | ctc | aaa | ctt | gga | gat | cca | gcc | aaa | ggc | atg | tcg | 912 |
| Glu | Asp | Arg | Ser | Lys | Leu | Lys | Leu | Gly | Asp | Pro | Ala | Lys | Gly | Met | Ser |  |
|  | 290 |  |  |  |  | 295 |  |  |  |  | 300 |  |  |  |  |  |
| ccc | cca | ggt | ttc | att | tct | ggt | gaa | gaa | ggt | gtc | ctc | tca | tat | ata | gaa | 960 |
| Pro | Pro | Gly | Phe | Ile | Ser | Gly | Glu | Glu | Gly | Val | Leu | Ser | Tyr | Ile | Glu |  |
| 305 |  |  |  |  | 310 |  |  |  |  | 315 |  |  |  |  | 320 |  |
| ttg | tgt | caa | ttg | ttt | caa | aaa | gaa | gaa | tgg | cat | atc | caa | tac | gat | gaa | 1008 |
| Leu | Cys | Gln | Leu | Phe | Gln | Lys | Glu | Glu | Trp | His | Ile | Gln | Tyr | Asp | Glu |  |
|  |  |  |  | 325 |  |  |  |  | 330 |  |  |  |  | 335 |  |  |
| tat | tac | aat | gct | cca | tat | ggt | tac | aat | gat | aaa | atc | tgg | gtc | ggt | tac | 1056 |
| Tyr | Tyr | Asn | Ala | Pro | Tyr | Gly | Tyr | Asn | Asp | Lys | Ile | Trp | Val | Gly | Tyr |  |
|  |  |  | 340 |  |  |  |  | 345 |  |  |  |  | 350 |  |  |  |
| gat | gat | ctg | gcc | agt | ata | tca | tgc | aag | ttg | gct | ttc | ctg | aaa | gaa | tta | 1104 |
| Asp | Asp | Leu | Ala | Ser | Ile | Ser | Cys | Lys | Leu | Ala | Phe | Leu | Lys | Glu | Leu |  |
|  |  | 355 |  |  |  |  | 360 |  |  |  |  | 365 |  |  |  |  |
| ggc | gtt | tct | ggt | gtc | atg | gtt | tgg | tca | ttg | gaa | aat | gat | gat | ttc | aaa | 1152 |
| Gly | Val | Ser | Gly | Val | Met | Val | Trp | Ser | Leu | Glu | Asn | Asp | Asp | Phe | Lys |  |
| 370 |  |  |  |  | 375 |  |  |  |  | 380 |  |  |  |  |  |  |
| ggt | cac | tgc | gga | ccg | aaa | aat | cca | ttg | ttg | aac | aaa | gtt | cat | aat | atg | 1200 |
| Gly | His | Cys | Gly | Pro | Lys | Asn | Pro | Leu | Leu | Asn | Lys | Val | His | Asn | Met |  |
| 385 |  |  |  |  | 390 |  |  |  |  | 395 |  |  |  |  | 400 |  |
| att | aat | ggc | gat | gaa | aag | aac | tct | ttc | gaa | tgc | att | ttg | ggt | cca | agt | 1248 |
| Ile | Asn | Gly | Asp | Glu | Lys | Asn | Ser | Phe | Glu | Cys | Ile | Leu | Gly | Pro | Ser |  |
|  |  |  |  | 405 |  |  |  |  | 410 |  |  |  |  | 415 |  |  |
| aca | acg | aca | cca | act | cca | acg | acg | aca | ccc | aca | acc | ccg | act | aca | acg | 1296 |
| Thr | Thr | Thr | Pro | Thr | Pro | Thr | Thr | Thr | Pro | Thr | Thr | Pro | Thr | Thr | Thr |  |
|  |  |  | 420 |  |  |  |  | 425 |  |  |  |  | 430 |  |  |  |
| cca | aca | act | cct | tct | ccc | acc | acc | ccg | aca | aca | acc | cct | tct | ccc | acc | 1344 |
| Pro | Thr | Thr | Pro | Ser | Pro | Thr | Thr | Pro | Thr | Thr | Thr | Pro | Ser | Pro | Thr |  |
|  |  | 435 |  |  |  |  | 440 |  |  |  |  | 445 |  |  |  |  |
| acc | ccg | aca | aca | acc | cct | tct | ccc | acc | aca | ccg | aca | aca | act | cct | tct | 1392 |
| Thr | Pro | Thr | Thr | Thr | Pro | Ser | Pro | Thr | Thr | Pro | Thr | Thr | Thr | Pro | Ser |  |
| 450 |  |  |  |  | 455 |  |  |  |  | 460 |  |  |  |  |  |  |
| ccc | acc | aca | cca | aca | cca | aca | aca | cca | aca | cca | gcc | cct | aca | aca | tcg | 1440 |
| Pro | Thr | Thr | Pro | Thr | Pro | Thr | Thr | Pro | Thr | Pro | Ala | Pro | Thr | Thr | Ser |  |
| 465 |  |  |  | 470 |  |  |  |  | 475 |  |  |  |  | 480 |  |  |
| aca | cct | tcg | cca | acc | acg | acc | gaa | cac | aca | agc | gaa | aca | cca | aaa | tat | 1488 |
| Thr | Pro | Ser | Pro | Thr | Thr | Thr | Glu | His | Thr | Ser | Glu | Thr | Pro | Lys | Tyr |  |
|  |  |  |  | 485 |  |  |  |  | 490 |  |  |  |  | 495 |  |  |
| aca | acc | tat | gtc | gat | gga | cat | ctt | atc | aaa | tgt | tac | aag | gaa | ggt | gat | 1536 |
| Thr | Thr | Tyr | Val | Asp | Gly | His | Leu | Ile | Lys | Cys | Tyr | Lys | Glu | Gly | Asp |  |
|  |  |  | 500 |  |  |  |  | 505 |  |  |  |  | 510 |  |  |  |
| atc | cca | cat | cca | acc | aat | ata | cac | aaa | tat | ttg | gtc | tgt | gaa | ttt | gtt | 1584 |
| Ile | Pro | His | Pro | Thr | Asn | Ile | His | Lys | Tyr | Leu | Val | Cys | Glu | Phe | Val |  |
|  |  | 515 |  |  |  |  | 520 |  |  |  |  | 525 |  |  |  |  |
| aat | ggt | ggc | tgg | tgg | gtt | cat | att | atg | ccc | tgt | cca | ccg | ggc | act | att | 1632 |
| Asn | Gly | Gly | Trp | Trp | Val | His | Ile | Met | Pro | Cys | Pro | Pro | Gly | Thr | Ile |  |
| 530 |  |  |  |  | 535 |  |  |  |  | 540 |  |  |  |  |  |  |
| tgg | tgt | caa | gaa | aaa | ttg | act | tgt | ata | ggc | gaa |  |  |  |  |  | 1665 |
| Trp | Cys | Gln | Glu | Lys | Leu | Thr | Cys | Ile | Gly | Glu |  |  |  |  |  |  |
| 545 |  |  |  |  | 550 |  |  |  | 555 |  |  |  |  |  |  |  |

<210> SEQ ID NO 18
<211> LENGTH: 555
<212> TYPE: PRT
<213> ORGANISM: Dermatophagoides farinae

<400> SEQUENCE: 18

```
Met Lys Thr Ile Tyr Ala Ile Leu Ser Ile Met Ala Cys Ile Gly Leu
 1               5                  10                  15

Met Asn Ala Ser Ile Lys Arg Asp His Asn Asp Tyr Ser Lys Asn Pro
             20                  25                  30

Met Arg Ile Val Cys Tyr Val Gly Thr Trp Ser Val Tyr His Lys Val
         35                  40                  45

Asp Pro Tyr Thr Ile Glu Asp Ile Asp Pro Phe Lys Cys Thr His Leu
     50                  55                  60

Met Tyr Gly Phe Ala Lys Ile Asp Glu Tyr Lys Tyr Thr Ile Gln Val
 65                  70                  75                  80

Phe Asp Pro Tyr Gln Asp Asn His Asn Ser Trp Glu Lys Arg Gly
                 85                  90                  95

Tyr Glu Arg Phe Asn Asn Leu Arg Leu Lys Asn Pro Glu Leu Thr Thr
                100                 105                 110

Met Ile Ser Leu Gly Gly Trp Tyr Glu Gly Ser Glu Lys Tyr Ser Asp
            115                 120                 125

Met Ala Ala Asn Pro Thr Tyr Arg Gln Gln Phe Ile Gln Ser Val Leu
        130                 135                 140

Asp Phe Leu Gln Glu Tyr Lys Phe Asp Gly Leu Asp Leu Asp Trp Glu
145                 150                 155                 160

Tyr Pro Gly Ser Arg Leu Gly Asn Pro Lys Ile Asp Lys Gln Asn Tyr
                165                 170                 175

Leu Ala Leu Val Arg Glu Leu Lys Asp Ala Phe Glu Pro His Gly Tyr
                180                 185                 190

Leu Leu Thr Ala Ala Val Ser Pro Gly Lys Asp Lys Ile Asp Arg Ala
            195                 200                 205

Tyr Asp Ile Lys Glu Leu Asn Lys Leu Phe Asp Trp Met Asn Val Met
        210                 215                 220

Thr Tyr Asp Tyr His Gly Gly Trp Glu Asn Phe Tyr Gly His Asn Ala
225                 230                 235                 240

Pro Leu Tyr Lys Arg Pro Asp Glu Thr Asp Glu Leu His Thr Tyr Phe
                245                 250                 255

Asn Val Asn Tyr Thr Met His Tyr Tyr Leu Asn Asn Gly Ala Thr Arg
                260                 265                 270

Asp Lys Leu Val Met Gly Val Pro Phe Tyr Gly Arg Ala Trp Ser Ile
            275                 280                 285

Glu Asp Arg Ser Lys Leu Lys Leu Gly Asp Pro Ala Lys Gly Met Ser
        290                 295                 300

Pro Pro Gly Phe Ile Ser Gly Glu Glu Gly Val Leu Ser Tyr Ile Glu
305                 310                 315                 320

Leu Cys Gln Leu Phe Gln Lys Glu Glu Trp His Ile Gln Tyr Asp Glu
                325                 330                 335

Tyr Tyr Asn Ala Pro Tyr Gly Tyr Asn Asp Lys Ile Trp Val Gly Tyr
                340                 345                 350

Asp Asp Leu Ala Ser Ile Ser Cys Lys Leu Ala Phe Leu Lys Glu Leu
            355                 360                 365

Gly Val Ser Gly Val Met Val Trp Ser Leu Glu Asn Asp Asp Phe Lys
        370                 375                 380
```

```
Gly His Cys Gly Pro Lys Asn Pro Leu Leu Asn Lys Val His Asn Met
385                 390                 395                 400

Ile Asn Gly Asp Glu Lys Asn Ser Phe Glu Cys Ile Leu Gly Pro Ser
            405                 410                 415

Thr Thr Thr Pro Thr Pro Thr Thr Thr Pro Thr Pro Thr Thr Thr
                420                 425                 430

Pro Thr Thr Pro Ser Pro Thr Thr Pro Thr Thr Thr Pro Ser Pro Thr
            435                 440                 445

Thr Pro Thr Thr Thr Pro Ser Pro Thr Thr Pro Thr Thr Thr Pro Ser
        450                 455                 460

Pro Thr Thr Pro Thr Pro Thr Thr Pro Thr Pro Ala Pro Thr Thr Ser
465                 470                 475                 480

Thr Pro Ser Pro Thr Thr Thr Glu His Thr Ser Glu Thr Pro Lys Tyr
                485                 490                 495

Thr Thr Tyr Val Asp Gly His Leu Ile Lys Cys Tyr Lys Glu Gly Asp
            500                 505                 510

Ile Pro His Pro Thr Asn Ile His Lys Tyr Leu Val Cys Glu Phe Val
        515                 520                 525

Asn Gly Gly Trp Trp Val His Ile Met Pro Cys Pro Pro Gly Thr Ile
    530                 535                 540

Trp Cys Gln Glu Lys Leu Thr Cys Ile Gly Glu
545                 550                 555

<210> SEQ ID NO 19
<211> LENGTH: 1665
<212> TYPE: DNA
<213> ORGANISM: Dermatophagoides farinae

<400> SEQUENCE: 19
ttcgcctata caagtcaatt tttcttgaca ccaaatagtg cccggtggac agggcataat      60
atgaacccac cagccaccat taacaaattc acagaccaaa tatttgtgta tattggttgg     120
atgtgggata tcaccttcct tgtaacattt gataagatgt ccatcgacat aggttgtata     180
ttttggtgtt tcgcttgtgt gttcggtcgt ggttggcgaa ggtgtcgatg ttgtaggggc     240
tggtgttggt gttgttggtg ttggtgtggt gggagaagga gttgttgtcg gtgtggtggg     300
agaagggggtt gttgtcgggg tggtgggaga aggggttgtt gtcggggtgg tgggagaagg     360
agttgttggc gttgtagtcg gggttgtggg tgtcgtcgtt ggagttggtg tcgttgtact     420
tggacccaaa atgcattcga aagagttctt ttcatcgcca ttaatcatat tatgaacttt     480
gttcaacaat ggattttttcg gtccgcagtg accttttgaaa tcatcatttt ccaatgacca     540
aaccatgaca ccagaaacgc ctaattcttt caggaaagcc aacttgcatg atatactggc     600
cagatcatcg taaccgaccc agattttatc attgtaacca tatggagcat tgtaatattc     660
atcgtattgg atatgccatt cttctttttg aaacaattga cacaattcta tatatgagag     720
gacaccttct tcaccagaaa tgaaacctgg gggcgacatg cctttggctg gatctccaag     780
tttgagtttg cttcgatctt caatgctcca agcacggcca tagaatggaa cacccattac     840
caatttgtct ctggtggcac cattgttcaa ataatagtgc atggtgtagt tgacattgaa     900
gtaagtgtgc aactcatcag tttcatctgg tcgtttatac aacggagcat tgtgaccgta     960
aaagttttcc catccaccgt ggtaatcata tgtcatgaca ttcatccaat cgaacaattt    1020
gttcaattct ttgatatcat aagctcggtc gattttgtct ttacctggtg atactgcagc    1080
agtcaacaag tagccatgag gttcaaaagc gtctttaagt tctctaacca aagccaaata    1140
```

-continued

```
gttttgttta tcgatttcg ggttacccaa tcgagatcca ggatactccc aatccaaatc    1200
tagaccgtcg aacttgtatt cttgcaaaaa gtccaaaact gattgtatga attgttgacg    1260
atatgttgga tttgcagcca tatcggaata tttttccgag ccttcatacc aaccaccaag    1320
tgaaatcatg gtggttaatt ctggattctt caatcgcaag ttgttgaaac gttcataacc    1380
acgtttttcc catgagttat ggttatcatc ttggtaagga tcgaaaactt gaattgtgta    1440
tttgtattca tcaattttag cgaaaccata cattaaatgt gtacacttga atggatcaat    1500
atcttcgata gtgtatggat caactttatg atatacggac catgttccaa cataacaaac    1560
aattctcatc ggattttcg aataatcatt atgatctcgt tgatggatg cattcataag    1620 gccaatgcag gccataatac taagtattgc atatatggtt ttcat    1665
```

<210> SEQ ID NO 20
<211> LENGTH: 1608
<212> TYPE: DNA
<213> ORGANISM: Dermatophagoides farinae
<220> FEATURE:
<221> NAME/KEY: CDS
<222> LOCATION: (1)..(1608)

<400> SEQUENCE: 20

```
tcc atc aaa cga gat cat aat gat tat tcg aaa aat ccg atg aga att     48
Ser Ile Lys Arg Asp His Asn Asp Tyr Ser Lys Asn Pro Met Arg Ile
 1               5                  10                  15 gtt tgt tat gtt gga aca tgg tcc gta tat cat aaa gtt gat cca tac     96
Val Cys Tyr Val Gly Thr Trp Ser Val Tyr His Lys Val Asp Pro Tyr
                20                  25                  30 act atc gaa gat att gat cca ttc aag tgt aca cat tta atg tat ggt    144
Thr Ile Glu Asp Ile Asp Pro Phe Lys Cys Thr His Leu Met Tyr Gly
            35                  40                  45 ttc gct aaa att gat gaa tac aaa tac aca att caa gtt ttc gat cct    192
Phe Ala Lys Ile Asp Glu Tyr Lys Tyr Thr Ile Gln Val Phe Asp Pro
        50                  55                  60 tac caa gat gat aac cat aac tca tgg gaa aaa cgt ggt tat gaa cgt    240
Tyr Gln Asp Asp Asn His Asn Ser Trp Glu Lys Arg Gly Tyr Glu Arg
 65                  70                  75                  80 ttc aac aac ttg cga ttg aag aat cca gaa tta acc acc atg att tca    288
Phe Asn Asn Leu Arg Leu Lys Asn Pro Glu Leu Thr Thr Met Ile Ser
                85                  90                  95 ctt ggt ggt tgg tat gaa ggc tcg gaa aaa tat tcc gat atg gct gca    336
Leu Gly Gly Trp Tyr Glu Gly Ser Glu Lys Tyr Ser Asp Met Ala Ala
                100                 105                 110 aat cca aca tat cgt caa caa ttc ata caa tca gtt ttg gac ttt ttg    384
Asn Pro Thr Tyr Arg Gln Gln Phe Ile Gln Ser Val Leu Asp Phe Leu
            115                 120                 125 caa gaa tac aag ttc gac ggt cta gat ttg gat tgg gag tat cct gga    432
Gln Glu Tyr Lys Phe Asp Gly Leu Asp Leu Asp Trp Glu Tyr Pro Gly
        130                 135                 140 tct cga ttg ggt aac ccg aaa atc gat aaa caa aac tat ttg gct ttg    480
Ser Arg Leu Gly Asn Pro Lys Ile Asp Lys Gln Asn Tyr Leu Ala Leu
145                 150                 155                 160 gtt aga gaa ctt aaa gac gct ttt gaa cct cat ggc tac ttg ttg act    528
Val Arg Glu Leu Lys Asp Ala Phe Glu Pro His Gly Tyr Leu Leu Thr
                165                 170                 175 gct gca gta tca cca ggt aaa gac aaa atc gac cga gct tat gat atc    576
Ala Ala Val Ser Pro Gly Lys Asp Lys Ile Asp Arg Ala Tyr Asp Ile
                180                 185                 190 aaa gaa ttg aac aaa ttg ttc gat tgg atg aat gtc atg aca tat gat    624
Lys Glu Leu Asn Lys Leu Phe Asp Trp Met Asn Val Met Thr Tyr Asp
```

-continued

```
                195                 200                 205
tac cac ggt gga tgg gaa aac ttt tac ggt cac aat gct ccg ttg tat    672
Tyr His Gly Gly Trp Glu Asn Phe Tyr Gly His Asn Ala Pro Leu Tyr
    210                 215                 220 aaa cga cca gat gaa act gat gag ttg cac act tac ttc aat gtc aac    720
Lys Arg Pro Asp Glu Thr Asp Glu Leu His Thr Tyr Phe Asn Val Asn
225                 230                 235                 240 tac acc atg cac tat tat ttg aac aat ggt gcc acc aga gac aaa ttg    768
Tyr Thr Met His Tyr Tyr Leu Asn Asn Gly Ala Thr Arg Asp Lys Leu
                245                 250                 255 gta atg ggt gtt cca ttc tat ggc cgt gct tgg agc att gaa gat cga    816
Val Met Gly Val Pro Phe Tyr Gly Arg Ala Trp Ser Ile Glu Asp Arg
            260                 265                 270 agc aaa ctc aaa ctt gga gat cca gcc aaa ggc atg tcg ccc cca ggt    864
Ser Lys Leu Lys Leu Gly Asp Pro Ala Lys Gly Met Ser Pro Pro Gly
        275                 280                 285 ttc att tct ggt gaa gaa ggt gtc ctc tca tat ata gaa ttg tgt caa    912
Phe Ile Ser Gly Glu Glu Gly Val Leu Ser Tyr Ile Glu Leu Cys Gln
    290                 295                 300 ttg ttt caa aaa gaa gaa tgg cat atc caa tac gat gaa tat tac aat    960
Leu Phe Gln Lys Glu Glu Trp His Ile Gln Tyr Asp Glu Tyr Tyr Asn
305                 310                 315                 320 gct cca tat ggt tac aat gat aaa atc tgg gtc ggt tac gat gat ctg   1008
Ala Pro Tyr Gly Tyr Asn Asp Lys Ile Trp Val Gly Tyr Asp Asp Leu
                325                 330                 335 gcc agt ata tca tgc aag ttg gct ttc ctg aaa gaa tta ggc gtt tct   1056
Ala Ser Ile Ser Cys Lys Leu Ala Phe Leu Lys Glu Leu Gly Val Ser
            340                 345                 350 ggt gtc atg gtt tgg tca ttg gaa aat gat gat ttc aaa ggt cac tgc   1104
Gly Val Met Val Trp Ser Leu Glu Asn Asp Asp Phe Lys Gly His Cys
        355                 360                 365 gga ccg aaa aat cca ttg ttg aac aaa gtt cat aat atg att aat ggc   1152
Gly Pro Lys Asn Pro Leu Leu Asn Lys Val His Asn Met Ile Asn Gly
    370                 375                 380 gat gaa aag aac tct ttc gaa tgc att ttg ggt cca agt aca acg aca   1200
Asp Glu Lys Asn Ser Phe Glu Cys Ile Leu Gly Pro Ser Thr Thr Thr
385                 390                 395                 400 cca act cca acg acg aca ccc aca acc ccg act aca acg cca aca act   1248
Pro Thr Pro Thr Thr Thr Pro Thr Thr Pro Thr Thr Thr Pro Thr Thr
                405                 410                 415 cct tct ccc acc acc ccg aca aca acc cct tct ccc acc acc ccg aca   1296
Pro Ser Pro Thr Thr Pro Thr Thr Thr Pro Ser Pro Thr Thr Pro Thr
            420                 425                 430 aca acc cct tct ccc acc aca ccg aca aca act cct tct ccc acc aca   1344
Thr Thr Pro Ser Pro Thr Thr Pro Thr Thr Thr Pro Ser Pro Thr Thr
        435                 440                 445 cca aca cca aca aca cca aca cca gcc cct aca aca tcg aca cct tcg   1392
Pro Thr Pro Thr Thr Pro Thr Pro Ala Pro Thr Thr Ser Thr Pro Ser
    450                 455                 460 cca acc acg acc gaa cac aca agc gaa aca cca aaa tat aca acc tat   1440
Pro Thr Thr Thr Glu His Thr Ser Glu Thr Pro Lys Tyr Thr Thr Tyr
465                 470                 475                 480 gtc gat gga cat ctt atc aaa tgt tac aag gaa ggt gat atc cca cat   1488
Val Asp Gly His Leu Ile Lys Cys Tyr Lys Glu Gly Asp Ile Pro His
                485                 490                 495 cca acc aat ata cac aaa tat ttg gtc tgt gaa ttt gtt aat ggt ggc   1536
Pro Thr Asn Ile His Lys Tyr Leu Val Cys Glu Phe Val Asn Gly Gly
            500                 505                 510 tgg tgg gtt cat att atg ccc tgt cca ccg ggc act att tgg tgt caa   1584
Trp Trp Val His Ile Met Pro Cys Pro Pro Gly Thr Ile Trp Cys Gln
```

```
Trp Trp Val His Ile Met Pro Cys Pro Pro Gly Thr Ile Trp Cys Gln
            515                 520                 525 gaa aaa ttg act tgt ata ggc gaa                                              1608
Glu Lys Leu Thr Cys Ile Gly Glu
        530                 535

<210> SEQ ID NO 21
<211> LENGTH: 536
<212> TYPE: PRT
<213> ORGANISM: Dermatophagoides farinae

<400> SEQUENCE: 21

Ser Ile Lys Arg Asp His Asn Asp Tyr Ser Lys Asn Pro Met Arg Ile
  1               5                  10                  15

Val Cys Tyr Val Gly Thr Trp Ser Val Tyr His Lys Val Asp Pro Tyr
                 20                  25                  30

Thr Ile Glu Asp Ile Asp Pro Phe Lys Cys Thr His Leu Met Tyr Gly
             35                  40                  45

Phe Ala Lys Ile Asp Glu Tyr Lys Tyr Thr Ile Gln Val Phe Asp Pro
         50                  55                  60

Tyr Gln Asp Asp Asn His Asn Ser Trp Glu Lys Arg Gly Tyr Glu Arg
 65                  70                  75                  80

Phe Asn Asn Leu Arg Leu Lys Asn Pro Glu Leu Thr Thr Met Ile Ser
                 85                  90                  95

Leu Gly Gly Trp Tyr Glu Gly Ser Glu Lys Tyr Ser Asp Met Ala Ala
            100                 105                 110

Asn Pro Thr Tyr Arg Gln Gln Phe Ile Gln Ser Val Leu Asp Phe Leu
        115                 120                 125

Gln Glu Tyr Lys Phe Asp Gly Leu Asp Leu Asp Trp Glu Tyr Pro Gly
    130                 135                 140

Ser Arg Leu Gly Asn Pro Lys Ile Asp Lys Gln Asn Tyr Leu Ala Leu
145                 150                 155                 160

Val Arg Glu Leu Lys Asp Ala Phe Glu Pro His Gly Tyr Leu Leu Thr
                165                 170                 175

Ala Ala Val Ser Pro Gly Lys Asp Lys Ile Asp Arg Ala Tyr Asp Ile
            180                 185                 190

Lys Glu Leu Asn Lys Leu Phe Asp Trp Met Asn Val Met Thr Tyr Asp
        195                 200                 205

Tyr His Gly Gly Trp Glu Asn Phe Tyr Gly His Asn Ala Pro Leu Tyr
    210                 215                 220

Lys Arg Pro Asp Glu Thr Asp Glu Leu His Thr Tyr Phe Asn Val Asn
225                 230                 235                 240

Tyr Thr Met His Tyr Tyr Leu Asn Asn Gly Ala Thr Arg Asp Lys Leu
                245                 250                 255

Val Met Gly Val Pro Phe Tyr Gly Arg Ala Trp Ser Ile Glu Asp Arg
            260                 265                 270

Ser Lys Leu Lys Leu Gly Asp Pro Ala Lys Gly Met Ser Pro Pro Gly
        275                 280                 285

Phe Ile Ser Gly Glu Glu Gly Val Leu Ser Tyr Ile Glu Leu Cys Gln
    290                 295                 300

Leu Phe Gln Lys Glu Glu Trp His Ile Gln Tyr Asp Glu Tyr Tyr Asn
305                 310                 315                 320

Ala Pro Tyr Gly Tyr Asn Asp Lys Ile Trp Val Gly Tyr Asp Asp Leu
                325                 330                 335

Ala Ser Ile Ser Cys Lys Leu Ala Phe Leu Lys Glu Leu Gly Val Ser
```

```
                    340             345             350
Gly Val Met Val Trp Ser Leu Glu Asn Asp Phe Lys Gly His Cys
                355             360             365
Gly Pro Lys Asn Pro Leu Leu Asn Lys Val His Asn Met Ile Asn Gly
            370             375             380
Asp Glu Lys Asn Ser Phe Glu Cys Ile Leu Gly Pro Ser Thr Thr Thr
385             390             395             400
Pro Thr Pro Thr Thr Thr Pro Thr Thr Thr Thr Pro Thr Thr
                405             410             415
Pro Ser Pro Thr Thr Pro Thr Thr Thr Pro Ser Pro Thr Thr Pro Thr
            420             425             430
Thr Thr Pro Ser Pro Thr Thr Pro Thr Thr Thr Pro Ser Pro Thr Thr
            435             440             445
Pro Thr Pro Thr Thr Pro Thr Pro Ala Pro Thr Thr Ser Thr Pro Ser
            450             455             460
Pro Thr Thr Thr Glu His Thr Ser Glu Thr Pro Lys Tyr Thr Thr Tyr
465             470             475             480
Val Asp Gly His Leu Ile Lys Cys Tyr Lys Glu Gly Asp Ile Pro His
                485             490             495
Pro Thr Asn Ile His Lys Tyr Leu Val Cys Glu Phe Val Asn Gly Gly
            500             505             510
Trp Trp Val His Ile Met Pro Cys Pro Pro Gly Thr Ile Trp Cys Gln
            515             520             525
Glu Lys Leu Thr Cys Ile Gly Glu
        530             535

<210> SEQ ID NO 22
<211> LENGTH: 1608
<212> TYPE: DNA
<213> ORGANISM: Dermatophagoides farinae

<400> SEQUENCE: 22
ttcgcctata caagtcaatt tttcttgaca ccaaatagtg cccggtggac agggcataat    60
atgaacccac cagccaccat taacaaattc acagaccaaa tatttgtgta tattggttgg   120
atgtgggata tcaccttcct tgtaacattt gataagatgt ccatcgacat aggttgtata   180
ttttggtgtt tcgcttgtgt gttcggtcgt ggttggcgaa ggtgtcgatg ttgtagggc   240
tggtgttggt gttgttggtg ttggtgtggt gggagaagga gttgttgtcg gtgtggtggg   300
agaaggggtt gttgtcgggg tggtgggaga aggggttgtt gtcggggtgg tgggagaagg   360
agttgttggc gttgtagtcg gggttgtggg tgtcgtcgtt ggagttggtg tcgttgtact   420
tggacccaaa atgcattcga aagagttctt ttcatcgcca ttaatcatat tatgaacttt   480
gttcaacaat ggattttcg gtccgcagtg acctttgaaa tcatcatttt ccaatgacca   540
aaccatgaca ccagaaacgc ctaattcttt caggaaagcc aacttgcatg atatactggc   600
cagatcatcg taaccgaccc agattttatc attgtaacca tatggagcat tgtaatattc   660
atcgtattgg atatgccatt cttcttttttg aaacaattga cacaattcta tatatgagag   720
gacaccttct tcaccagaaa tgaaacctgg gggcgacatg cctttggctg gatctccaag   780
tttgagtttg cttcgatctt caatgctcca agcacggcca tagaatgaaa cacccattac   840
caatttgtct ctggtggcac cattgttcaa ataatagtgc atggtgtagt tgacattgaa   900
gtaagtgtgc aactcatcag tttcatctgg tcgtttatac aacggagcat tgtgaccgta   960
aaagttttcc catccaccgt ggtaatcata tgtcatgaca ttcatccaat cgaacaattt  1020
```

-continued

```
gttcaattct ttgatatcat aagctcggtc gattttgtct ttacctggtg atactgcagc    1080
agtcaacaag tagccatgag gttcaaaagc gtctttaagt tctctaacca aagccaaata    1140
gttttgttta tcgattttcg ggttacccaa tcgagatcca ggatactccc aatccaaatc    1200
tagaccgtcg aacttgtatt cttgcaaaaa gtccaaaact gattgtatga attgttgacg    1260
atatgttgga tttgcagcca tatcggaata tttttccgag ccttcatacc aaccaccaag    1320
tgaaatcatg gtggttaatt ctggattctt caatcgcaag ttgttgaaac gttcataacc    1380 acgttttttcc catgagttat ggttatcatc ttggtaagga tcgaaaactt gaattgtgta    1440
tttgtattca tcaattttag cgaaaccata cattaaatgt gtacacttga atggatcaat    1500
atcttcgata gtgtatggat caactttatg atatacggac catgttccaa cataacaaac    1560
aattctcatc ggattttttcg aataatcatt atgatctcgt ttgatgga              1608
```

<210> SEQ ID NO 23
<211> LENGTH: 25
<212> TYPE: PRT
<213> ORGANISM: Dermatophagoides farinae
<220> FEATURE:
<223> OTHER INFORMATION: At location 1, Xaa = any amino acid

<400> SEQUENCE: 23

Xaa Leu Glu Pro Lys Thr Val Cys Tyr Tyr Glu Ser Trp Val His His
 1               5                  10                  15

Arg Gln Gly Glu Gly Lys Met Asp Pro
            20                  25

<210> SEQ ID NO 24
<211> LENGTH: 33
<212> TYPE: PRT
<213> ORGANISM: Dermatophagoides farinae
<220> FEATURE:
<223> OTHER INFORMATION: At locations, 18, 28, 31 and 32, Xaa = any
     amino acid

<400> SEQUENCE: 24

Ser Ile Lys Arg Asp His Asn Asp Tyr Ser Lys Asn Pro Met Met Ile
 1               5                  10                  15

Val Xaa Tyr Gly Gly Ser Ser Gly Tyr Gln Ser Xaa Lys Arg Xaa Xaa
            20                  25                  30

Thr

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
     Primer
<220> FEATURE:
<223> OTHER INFORMATION: At location 24, n = a, c, t or g

<400> SEQUENCE: 25
aaacgtgatc ataaygatta ytcnaaraay c                                    31

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
     Primer

```
<400> SEQUENCE: 26
aaacgtgatc ataaygatta yagyaaraay c                               31

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: At locations 12 and 21,  n = a, c, t or g

<400> SEQUENCE: 27
ccttcttcac cnacratcaa ncc                                        23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<223> OTHER INFORMATION: At locations 12 and 21,  n = a, c, t or g

<400> SEQUENCE: 28
ccttcttcac cnacratgaa ncc                                        23

<210> SEQ ID NO 29
<211> LENGTH: 13
<212> TYPE: PRT
<213> ORGANISM: Dermatophagoides farinae

<400> SEQUENCE: 29

Gln Tyr Gly Val Thr Gln Ala Val Val Thr Gln Pro Ala
 1               5                  10

<210> SEQ ID NO 30
<211> LENGTH: 11
<212> TYPE: PRT
<213> ORGANISM: Dermatophagoides farinae

<400> SEQUENCE: 30

Asp Glu Leu Leu Met Lys Ser Gly Pro Gly Pro
 1               5                  10

<210> SEQ ID NO 31
<211> LENGTH: 24
<212> TYPE: PRT
<213> ORGANISM: Dermatophagoides farinae

<400> SEQUENCE: 31

Asp Met Glu His Phe Thr Gln His Lys Gly Asn Ala Lys Ala Met Ile
 1               5                  10                  15

Ala Val Gly Gly Ser Thr Met Ser
            20

<210> SEQ ID NO 32
<211> LENGTH: 21
<212> TYPE: PRT
<213> ORGANISM: Dermatophagoides farinae

<400> SEQUENCE: 32
```

```
Asp Ala Asn Glu Glu Ala Arg Ser Gln Leu Pro Glu Thr Ala Met Val
 1               5                  10                  15

Leu Ile Lys Ser Gln
            20

<210> SEQ ID NO 33
<211> LENGTH: 21
<212> TYPE: PRT
<213> ORGANISM: Dermatophagoides farinae

<400> SEQUENCE: 33

Gln Ser Arg Asp Arg Asn Asp Lys Pro Tyr Xaa Ile Val Lys Lys Lys
 1               5                  10                  15

Lys Lys Ala Leu Asp
            20

<210> SEQ ID NO 34
<211> LENGTH: 1621
<212> TYPE: DNA
<213> ORGANISM: Dermatophagoides farinae
<220> FEATURE:
<221> NAME/KEY: CDS
<222> LOCATION: (14)..(1540)

<400> SEQUENCE: 34
agaacttatg aaa atg aaa acg aca ttt gca ttg ttt tgt ata tgg gcc         49
            Met Lys Thr Thr Phe Ala Leu Phe Cys Ile Trp Ala
             1               5                  10 tgc att ggc ttg atg aat gcg gcc act aaa cga gat cac aat aat tat        97
Cys Ile Gly Leu Met Asn Ala Ala Thr Lys Arg Asp His Asn Asn Tyr
        15                  20                  25 tcg aaa aat cca atg cga atc gta tgt tat gtt gga aca tgg tcc gtt       145
Ser Lys Asn Pro Met Arg Ile Val Cys Tyr Val Gly Thr Trp Ser Val
    30                  35                  40 tat cat aaa gtt gat cca tac aca att gaa gat att gat cct ttc aaa       193
Tyr His Lys Val Asp Pro Tyr Thr Ile Glu Asp Ile Asp Pro Phe Lys
45                  50                  55                  60 tgt act cat ttg atg tat ggt ttt gct aaa atc gat gaa tac aaa tac       241
Cys Thr His Leu Met Tyr Gly Phe Ala Lys Ile Asp Glu Tyr Lys Tyr
                65                  70                  75 acc att caa gtt ttt gat cca ttt caa gat gat aac cat aac tca tgg       289
Thr Ile Gln Val Phe Asp Pro Phe Gln Asp Asp Asn His Asn Ser Trp
            80                  85                  90 gaa aaa cac ggg tat gaa cgt ttc aac aac ttg aga ttg aag aat cca       337
Glu Lys His Gly Tyr Glu Arg Phe Asn Asn Leu Arg Leu Lys Asn Pro
        95                  100                 105 gaa ttg acc acc atg att tca ttg ggt ggt tgg tat gaa ggt tca gaa       385
Glu Leu Thr Thr Met Ile Ser Leu Gly Gly Trp Tyr Glu Gly Ser Glu
    110                 115                 120 aaa tat tcg gat atg gca gcc aat cca aca tat cgt cag caa ttt gtt      433
Lys Tyr Ser Asp Met Ala Ala Asn Pro Thr Tyr Arg Gln Gln Phe Val
125                 130                 135                 140 caa tca gtt ttg gac ttt ttg caa gaa tac aaa ttc gat ggc cta gat       481
Gln Ser Val Leu Asp Phe Leu Gln Glu Tyr Lys Phe Asp Gly Leu Asp
                145                 150                 155 ttg gat tgg gaa tat cct gga tca cgg tta ggc aat cct aaa atc gat       529
Leu Asp Trp Glu Tyr Pro Gly Ser Arg Leu Gly Asn Pro Lys Ile Asp
            160                 165                 170 aaa caa aac tat tta aca tta gtt aga gaa ctt aaa gag gca ttt gaa       577
Lys Gln Asn Tyr Leu Thr Leu Val Arg Glu Leu Lys Glu Ala Phe Glu
        175                 180                 185
```

```
cct ttc ggc tac ttg ttg act gcc gca gta tca ccc ggt aaa gat aaa      625
Pro Phe Gly Tyr Leu Leu Thr Ala Ala Val Ser Pro Gly Lys Asp Lys
    190                 195                 200 att gac gta gct tat gag ctc aaa gaa ttg aac caa ttg ttc gat tgg      673
Ile Asp Val Ala Tyr Glu Leu Lys Glu Leu Asn Gln Leu Phe Asp Trp
205                 210                 215                 220 atg aat gtc atg act tat gat tac cat ggc gga tgg gaa aat gtt ttc      721
Met Asn Val Met Thr Tyr Asp Tyr His Gly Gly Trp Glu Asn Val Phe
                225                 230                 235 ggc cat aat gct ccg ttg tat aaa cga ccc gat gaa acg gat gaa ttg      769
Gly His Asn Ala Pro Leu Tyr Lys Arg Pro Asp Glu Thr Asp Glu Leu
            240                 245                 250 cac act tac ttc aat gtc aac tac acc atg cac tat tat ttg aac aat      817
His Thr Tyr Phe Asn Val Asn Tyr Thr Met His Tyr Tyr Leu Asn Asn
                255                 260                 265 ggc gct act cga gac aaa ctt gtt atg ggt gtt cca ttc tat ggt cgt      865
Gly Ala Thr Arg Asp Lys Leu Val Met Gly Val Pro Phe Tyr Gly Arg
270                 275                 280 gct tgg agc atc gaa gat cga agc aaa gtc aaa ctt ggc gat ccg gcc      913
Ala Trp Ser Ile Glu Asp Arg Ser Lys Val Lys Leu Gly Asp Pro Ala
285                 290                 295                 300 aaa ggc atg tct cct cct ggt ttt att act ggt gaa gaa ggt gtt ctc      961
Lys Gly Met Ser Pro Pro Gly Phe Ile Thr Gly Glu Glu Gly Val Leu
                305                 310                 315 tca tac atc gaa ttg tgt cag tta ttc cag aaa gaa gaa tgg cat att     1009
Ser Tyr Ile Glu Leu Cys Gln Leu Phe Gln Lys Glu Glu Trp His Ile
            320                 325                 330 caa tac gat gaa tat tac aat gct cca tac gga tat aat gat aaa atc     1057
Gln Tyr Asp Glu Tyr Tyr Asn Ala Pro Tyr Gly Tyr Asn Asp Lys Ile
                335                 340                 345 tgg gtt ggt tac gat gat ctg gct agt ata tca tgc aag ttg gcc ttt     1105
Trp Val Gly Tyr Asp Asp Leu Ala Ser Ile Ser Cys Lys Leu Ala Phe
350                 355                 360 ctc aaa gaa ttg ggc gtc tct ggc gtt atg ata tgg tca ttg gaa aac     1153
Leu Lys Glu Leu Gly Val Ser Gly Val Met Ile Trp Ser Leu Glu Asn
365                 370                 375                 380 gat gat ttc aaa ggt cat tgc gga ccg aaa tat cca ttg ttg aac aaa     1201
Asp Asp Phe Lys Gly His Cys Gly Pro Lys Tyr Pro Leu Leu Asn Lys
                385                 390                 395 gtt cac aat atg atc aat ggt gat gaa aag aac tct tac gaa tgt ctt     1249
Val His Asn Met Ile Asn Gly Asp Glu Lys Asn Ser Tyr Glu Cys Leu
            400                 405                 410 ttg ggc cca agt aca acc aca cca aca cca acc acc ccg tca act act     1297
Leu Gly Pro Ser Thr Thr Thr Pro Thr Pro Thr Thr Pro Ser Thr Thr
                415                 420                 425 tcg act acc aca cca acg cct acc acc acc gat agc aca agc gaa aca     1345
Ser Thr Thr Thr Pro Thr Pro Thr Thr Thr Asp Ser Thr Ser Glu Thr
430                 435                 440 cca aaa tac act acg tat att gat gga cat ttg att aaa tgc tat aaa     1393
Pro Lys Tyr Thr Thr Tyr Ile Asp Gly His Leu Ile Lys Cys Tyr Lys
445                 450                 455                 460 caa ggt tat ctt cca cat cca act gat gtt cat aaa tat tta gtt tgt     1441
Gln Gly Tyr Leu Pro His Pro Thr Asp Val His Lys Tyr Leu Val Cys
                465                 470                 475 gaa tat att gcc aca cca aac ggt ggt tgg tgg gta cac att atg gat     1489
Glu Tyr Ile Ala Thr Pro Asn Gly Gly Trp Trp Val His Ile Met Asp
            480                 485                 490 tgt cca aaa gga act aga tgg cac gca aca tta aaa aat tgt att caa     1537
Cys Pro Lys Gly Thr Arg Trp His Ala Thr Leu Lys Asn Cys Ile Gln
                495                 500                 505
```

```
gaa tgatctgata tatttgtaac tgtttttttgc taaatgaaat ttaaataaaa        1590
Glu ttatttgaat ccattaaaaa aaaaaaaaaa a                                 1621
```

<210> SEQ ID NO 35
<211> LENGTH: 509
<212> TYPE: PRT
<213> ORGANISM: Dermatophagoides farinae

<400> SEQUENCE: 35

```
Met Lys Thr Thr Phe Ala Leu Phe Cys Ile Trp Ala Cys Ile Gly Leu
  1               5                  10                  15

Met Asn Ala Ala Thr Lys Arg Asp His Asn Asn Tyr Ser Lys Asn Pro
             20                  25                  30

Met Arg Ile Val Cys Tyr Val Gly Thr Trp Ser Val Tyr His Lys Val
         35                  40                  45

Asp Pro Tyr Thr Ile Glu Asp Ile Asp Pro Phe Lys Cys Thr His Leu
     50                  55                  60

Met Tyr Gly Phe Ala Lys Ile Asp Glu Tyr Lys Tyr Thr Ile Gln Val
 65                  70                  75                  80

Phe Asp Pro Phe Gln Asp Asn His Asn Ser Trp Glu Lys His Gly
                 85                  90                  95

Tyr Glu Arg Phe Asn Asn Leu Arg Leu Lys Asn Pro Glu Leu Thr Thr
                100                 105                 110

Met Ile Ser Leu Gly Gly Trp Tyr Glu Gly Ser Glu Lys Tyr Ser Asp
            115                 120                 125

Met Ala Ala Asn Pro Thr Tyr Arg Gln Gln Phe Val Gln Ser Val Leu
        130                 135                 140

Asp Phe Leu Gln Glu Tyr Lys Phe Asp Gly Leu Asp Leu Asp Trp Glu
145                 150                 155                 160

Tyr Pro Gly Ser Arg Leu Gly Asn Pro Lys Ile Asp Lys Gln Asn Tyr
                165                 170                 175

Leu Thr Leu Val Arg Glu Leu Lys Glu Ala Phe Glu Pro Phe Gly Tyr
            180                 185                 190

Leu Leu Thr Ala Ala Val Ser Pro Gly Lys Asp Lys Ile Asp Val Ala
        195                 200                 205

Tyr Glu Leu Lys Glu Leu Asn Gln Leu Phe Asp Trp Met Asn Val Met
    210                 215                 220

Thr Tyr Asp Tyr His Gly Gly Trp Glu Asn Val Phe Gly His Asn Ala
225                 230                 235                 240

Pro Leu Tyr Lys Arg Pro Asp Glu Thr Asp Glu Leu His Thr Tyr Phe
                245                 250                 255

Asn Val Asn Tyr Thr Met His Tyr Tyr Leu Asn Asn Gly Ala Thr Arg
            260                 265                 270

Asp Lys Leu Val Met Gly Val Pro Phe Tyr Gly Arg Ala Trp Ser Ile
        275                 280                 285

Glu Asp Arg Ser Lys Val Lys Leu Gly Asp Pro Ala Lys Gly Met Ser
    290                 295                 300

Pro Pro Gly Phe Ile Thr Gly Glu Glu Gly Val Leu Ser Tyr Ile Glu
305                 310                 315                 320

Leu Cys Gln Leu Phe Gln Lys Glu Glu Trp His Ile Gln Tyr Asp Glu
                325                 330                 335

Tyr Tyr Asn Ala Pro Tyr Gly Tyr Asn Asp Lys Ile Trp Val Gly Tyr
```

```
                   340               345               350
Asp Asp Leu Ala Ser Ile Ser Cys Lys Leu Ala Phe Leu Lys Glu Leu
            355                 360                 365
Gly Val Ser Gly Val Met Ile Trp Ser Leu Glu Asn Asp Asp Phe Lys
        370                 375                 380
Gly His Cys Gly Pro Lys Tyr Pro Leu Leu Asn Lys Val His Asn Met
385                 390                 395                 400
Ile Asn Gly Asp Glu Lys Asn Ser Tyr Glu Cys Leu Leu Gly Pro Ser
                405                 410                 415
Thr Thr Thr Pro Thr Pro Thr Thr Pro Ser Thr Thr Ser Thr Thr Thr
            420                 425                 430
Pro Thr Pro Thr Thr Thr Asp Ser Thr Ser Glu Thr Pro Lys Tyr Thr
            435                 440                 445
Thr Tyr Ile Asp Gly His Leu Ile Lys Cys Tyr Lys Gln Gly Tyr Leu
        450                 455                 460
Pro His Pro Thr Asp Val His Lys Tyr Leu Val Cys Glu Tyr Ile Ala
465                 470                 475                 480
Thr Pro Asn Gly Gly Trp Trp Val His Ile Met Asp Cys Pro Lys Gly
                485                 490                 495
Thr Arg Trp His Ala Thr Leu Lys Asn Cys Ile Gln Glu
            500                 505

<210> SEQ ID NO 36
<211> LENGTH: 1621
<212> TYPE: DNA
<213> ORGANISM: Dermatophagoides farinae

<400> SEQUENCE: 36
tttttttttt tttttttaatg gattcaaata attttattta aatttcattt agcaaaaaac      60
agttacaaat atatcagatc attcttgaat acaattttt aatgttgcgt gccatctagt      120
tcctttgga caatccataa tgtgtaccca ccaaccaccg tttggtgtgg caatatattc      180
acaaactaaa tatttatgaa catcagttgg atgtggaaga taaccttgtt tatagcattt      240
aatcaaatgt ccatcaatat acgtagtgta ttttggtgtt tcgcttgtgc tatcggtggt      300
ggtaggcgtt ggtgtggtag tcgaagtagt tgacggggtg gttggtgttg gtgtggttgt      360
acttgggccc aaaagacatt cgtaagagtt cttttcatca ccattgatca tattgtgaac      420
tttgttcaac aatggatatt tcggtccgca atgacctttg aaatcatcgt tttccaatga      480
ccatatcata acgccagaga cgcccaattc tttgagaaag gccaacttgc atgatatact      540
agccagatca tcgtaaccaa cccagatttt atcattatat ccgtatggag cattgtaata      600
ttcatcgtat tgaatatgcc attcttcttt ctggaataac tgacacaatt cgatgtatga      660
gagaacacct tcttcaccag taataaaacc aggaggagac atgcctttgg ccggatcgcc      720
aagtttgact ttgcttcgat cttcgatgct ccaagcacga ccatagaatg gaacacccat      780
aacaagtttg tctcgagtag cgccattgtt caaataatag tgcatggtgt agttgacatt      840
gaagtaagtg tgcaattcat ccgtttcatc gggtcgttta tacaacggag cattatggcc      900
gaaaacattt tcccatccgc catggtaatc ataagtcatg acattcatcc aatcgaacaa      960
ttggttcaat tctttgagct cataagctac gtcaatttta tctttaccgg gtgatactgc     1020
ggcagtcaac aagtagccga aaggttcaaa tgcctcttta agttctctaa ctaatgttaa     1080
atagttttgt ttatcgattt taggattgcc taaccgtgat ccaggatatt cccaatccaa     1140
atctaggcca tcgaatttgt attcttgcaa aaagtccaaa actgattgaa caaattgctg     1200
```

-continued

```
acgatatgtt ggattggctg ccatatccga atattttct gaaccttcat accaaccacc   1260
caatgaaatc atggtggtca attctggatt cttcaatctc aagttgttga aacgttcata   1320
cccgtgtttt tcccatgagt tatggttatc atcttgaaat ggatcaaaaa cttgaatggt   1380
gtatttgtat tcatcgattt tagcaaaacc atacatcaaa tgagtacatt tgaaaggatc   1440
aatatcttca attgtgtatg gatcaacttt atgataaacg gaccatgttc aacataaca   1500 tacgattcgc attggatttt tcgaataatt attgtgatct cgtttagtgg ccgcattcat   1560
caagccaatg caggcccata tacaaaacaa tgcaaatgtc gttttcattt tcataagttc   1620
t                                                                  1621
```

<210> SEQ ID NO 37
<211> LENGTH: 1527
<212> TYPE: DNA
<213> ORGANISM: Dermatophagoides farinae
<220> FEATURE:
<221> NAME/KEY: CDS
<222> LOCATION: (1)..(1527)

<400> SEQUENCE: 37

```
atg aaa acg aca ttt gca ttg ttt tgt ata tgg gcc tgc att ggc ttg      48
Met Lys Thr Thr Phe Ala Leu Phe Cys Ile Trp Ala Cys Ile Gly Leu
  1               5                  10                  15 atg aat gcg gcc act aaa cga gat cac aat aat tat tcg aaa aat cca      96
Met Asn Ala Ala Thr Lys Arg Asp His Asn Asn Tyr Ser Lys Asn Pro
             20                  25                  30 atg cga atc gta tgt tat gtt gga aca tgg tcc gtt tat cat aaa gtt     144
Met Arg Ile Val Cys Tyr Val Gly Thr Trp Ser Val Tyr His Lys Val
         35                  40                  45 gat cca tac aca att gaa gat att gat cct ttc aaa tgt act cat ttg     192
Asp Pro Tyr Thr Ile Glu Asp Ile Asp Pro Phe Lys Cys Thr His Leu
     50                  55                  60 atg tat ggt ttt gct aaa atc gat gaa tac aaa tac acc att caa gtt     240
Met Tyr Gly Phe Ala Lys Ile Asp Glu Tyr Lys Tyr Thr Ile Gln Val
 65                  70                  75                  80 ttt gat cca ttt caa gat gat aac cat aac tca tgg gaa aaa cac ggg     288
Phe Asp Pro Phe Gln Asp Asp Asn His Asn Ser Trp Glu Lys His Gly
                 85                  90                  95 tat gaa cgt ttc aac aac ttg aga ttg aag aat cca gaa ttg acc acc     336
Tyr Glu Arg Phe Asn Asn Leu Arg Leu Lys Asn Pro Glu Leu Thr Thr
            100                 105                 110 atg att tca ttg ggt ggt tgg tat gaa ggt tca gaa aaa tat tcg gat     384
Met Ile Ser Leu Gly Gly Trp Tyr Glu Gly Ser Glu Lys Tyr Ser Asp
        115                 120                 125 atg gca gcc aat cca aca tat cgt cag caa ttt gtt caa tca gtt ttg     432
Met Ala Ala Asn Pro Thr Tyr Arg Gln Gln Phe Val Gln Ser Val Leu
    130                 135                 140 gac ttt ttg caa gaa tac aaa ttc gat ggc cta gat ttg gat tgg gaa     480
Asp Phe Leu Gln Glu Tyr Lys Phe Asp Gly Leu Asp Leu Asp Trp Glu
145                 150                 155                 160 tat cct gga tca cgg tta ggc aat cct aaa atc gat aaa caa aac tat     528
Tyr Pro Gly Ser Arg Leu Gly Asn Pro Lys Ile Asp Lys Gln Asn Tyr
                165                 170                 175 tta aca tta gtt aga gaa ctt aaa gag gca ttt gaa cct ttc ggc tac     576
Leu Thr Leu Val Arg Glu Leu Lys Glu Ala Phe Glu Pro Phe Gly Tyr
            180                 185                 190 ttg ttg act gcc gca gta tca ccc ggt aaa gat aaa att gac gta gct     624
Leu Leu Thr Ala Ala Val Ser Pro Gly Lys Asp Lys Ile Asp Val Ala
        195                 200                 205
```

```
tat gag ctc aaa gaa ttg aac caa ttg ttc gat tgg atg aat gtc atg     672
Tyr Glu Leu Lys Glu Leu Asn Gln Leu Phe Asp Trp Met Asn Val Met
    210                 215                 220 act tat gat tac cat ggc gga tgg gaa aat gtt ttc ggc cat aat gct     720
Thr Tyr Asp Tyr His Gly Gly Trp Glu Asn Val Phe Gly His Asn Ala
225                 230                 235                 240 ccg ttg tat aaa cga ccc gat gaa acg gat gaa ttg cac act tac ttc     768
Pro Leu Tyr Lys Arg Pro Asp Glu Thr Asp Glu Leu His Thr Tyr Phe
                245                 250                 255 aat gtc aac tac acc atg cac tat tat ttg aac aat ggc gct act cga     816
Asn Val Asn Tyr Thr Met His Tyr Tyr Leu Asn Asn Gly Ala Thr Arg
            260                 265                 270 gac aaa ctt gtt atg ggt gtt cca ttc tat ggt cgt gct tgg agc atc     864
Asp Lys Leu Val Met Gly Val Pro Phe Tyr Gly Arg Ala Trp Ser Ile
        275                 280                 285 gaa gat cga agc aaa gtc aaa ctt ggc gat ccg gcc aaa ggc atg tct     912
Glu Asp Arg Ser Lys Val Lys Leu Gly Asp Pro Ala Lys Gly Met Ser
    290                 295                 300 cct cct ggt ttt att act ggt gaa gaa ggt gtt ctc tca tac atc gaa     960
Pro Pro Gly Phe Ile Thr Gly Glu Glu Gly Val Leu Ser Tyr Ile Glu
305                 310                 315                 320 ttg tgt cag tta ttc cag aaa gaa gaa tgg cat att caa tac gat gaa    1008
Leu Cys Gln Leu Phe Gln Lys Glu Glu Trp His Ile Gln Tyr Asp Glu
                325                 330                 335 tat tac aat gct cca tac gga tat aat gat aaa atc tgg gtt ggt tac    1056
Tyr Tyr Asn Ala Pro Tyr Gly Tyr Asn Asp Lys Ile Trp Val Gly Tyr
            340                 345                 350 gat gat ctg gct agt ata tca tgc aag ttg gcc ttt ctc aaa gaa ttg    1104
Asp Asp Leu Ala Ser Ile Ser Cys Lys Leu Ala Phe Leu Lys Glu Leu
        355                 360                 365 ggc gtc tct ggc gtt atg ata tgg tca ttg gaa aac gat gat ttc aaa    1152
Gly Val Ser Gly Val Met Ile Trp Ser Leu Glu Asn Asp Asp Phe Lys
    370                 375                 380 ggt cat tgc gga ccg aaa tat cca ttg ttg aac aaa gtt cac aat atg    1200
Gly His Cys Gly Pro Lys Tyr Pro Leu Leu Asn Lys Val His Asn Met
385                 390                 395                 400 atc aat ggt gat gaa aag aac tct tac gaa tgt ctt ttg ggc cca agt    1248
Ile Asn Gly Asp Glu Lys Asn Ser Tyr Glu Cys Leu Leu Gly Pro Ser
                405                 410                 415 aca acc aca cca aca cca acc acc ccg tca act act tcg act acc aca    1296
Thr Thr Thr Pro Thr Pro Thr Thr Pro Ser Thr Thr Ser Thr Thr Thr
            420                 425                 430 cca acg cct acc acc acc gat agc aca agc gaa aca cca aaa tac act    1344
Pro Thr Pro Thr Thr Thr Asp Ser Thr Ser Glu Thr Pro Lys Tyr Thr
        435                 440                 445 acg tat att gat gga cat ttg att aaa tgc tat aaa caa ggt tat ctt    1392
Thr Tyr Ile Asp Gly His Leu Ile Lys Cys Tyr Lys Gln Gly Tyr Leu
    450                 455                 460 cca cat cca act gat gtt cat aaa tat tta gtt tgt gaa tat att gcc    1440
Pro His Pro Thr Asp Val His Lys Tyr Leu Val Cys Glu Tyr Ile Ala
465                 470                 475                 480 aca cca aac ggt ggt tgg tgg gta cac att atg gat tgt cca aaa gga    1488
Thr Pro Asn Gly Gly Trp Trp Val His Ile Met Asp Cys Pro Lys Gly
                485                 490                 495 act aga tgg cac gca aca tta aaa aat tgt att caa gaa                1527
Thr Arg Trp His Ala Thr Leu Lys Asn Cys Ile Gln Glu
            500                 505
```

<210> SEQ ID NO 38

<211> LENGTH: 509
<212> TYPE: PRT
<213> ORGANISM: Dermatophagoides farinae

<400> SEQUENCE: 38

```
Met Lys Thr Thr Phe Ala Leu Phe Cys Ile Trp Ala Cys Ile Gly Leu
 1               5                  10                  15
Met Asn Ala Ala Thr Lys Arg Asp His Asn Asn Tyr Ser Lys Asn Pro
                20                  25                  30
Met Arg Ile Val Cys Tyr Val Gly Thr Trp Ser Val Tyr His Lys Val
            35                  40                  45
Asp Pro Tyr Thr Ile Glu Asp Ile Asp Pro Phe Lys Cys Thr His Leu
        50                  55                  60
Met Tyr Gly Phe Ala Lys Ile Asp Glu Tyr Lys Tyr Thr Ile Gln Val
 65                  70                  75                  80
Phe Asp Pro Phe Gln Asp Asp Asn His Asn Ser Trp Glu Lys His Gly
                85                  90                  95
Tyr Glu Arg Phe Asn Asn Leu Arg Leu Lys Asn Pro Glu Leu Thr Thr
                100                 105                 110
Met Ile Ser Leu Gly Gly Trp Tyr Glu Gly Ser Glu Lys Tyr Ser Asp
            115                 120                 125
Met Ala Ala Asn Pro Thr Tyr Arg Gln Gln Phe Val Gln Ser Val Leu
        130                 135                 140
Asp Phe Leu Gln Glu Tyr Lys Phe Asp Gly Leu Asp Leu Asp Trp Glu
145                 150                 155                 160
Tyr Pro Gly Ser Arg Leu Gly Asn Pro Lys Ile Asp Lys Gln Asn Tyr
                165                 170                 175
Leu Thr Leu Val Arg Glu Leu Lys Glu Ala Phe Glu Pro Phe Gly Tyr
            180                 185                 190
Leu Leu Thr Ala Ala Val Ser Pro Gly Lys Asp Lys Ile Asp Val Ala
        195                 200                 205
Tyr Glu Leu Lys Glu Leu Asn Gln Leu Phe Asp Trp Met Asn Val Met
    210                 215                 220
Thr Tyr Asp Tyr His Gly Gly Trp Glu Asn Val Phe Gly His Asn Ala
225                 230                 235                 240
Pro Leu Tyr Lys Arg Pro Asp Glu Thr Asp Glu Leu His Thr Tyr Phe
                245                 250                 255
Asn Val Asn Tyr Thr Met His Tyr Tyr Leu Asn Asn Gly Ala Thr Arg
            260                 265                 270
Asp Lys Leu Val Met Gly Val Pro Phe Tyr Gly Arg Ala Trp Ser Ile
        275                 280                 285
Glu Asp Arg Ser Lys Val Lys Leu Gly Asp Pro Ala Lys Gly Met Ser
    290                 295                 300
Pro Pro Gly Phe Ile Thr Gly Glu Glu Gly Val Leu Ser Tyr Ile Glu
305                 310                 315                 320
Leu Cys Gln Leu Phe Gln Lys Glu Glu Trp His Ile Gln Tyr Asp Glu
                325                 330                 335
Tyr Tyr Asn Ala Pro Tyr Gly Tyr Asn Asp Lys Ile Trp Val Gly Tyr
            340                 345                 350
Asp Asp Leu Ala Ser Ile Ser Cys Lys Leu Ala Phe Leu Lys Glu Leu
        355                 360                 365
Gly Val Ser Gly Val Met Ile Trp Ser Leu Glu Asn Asp Asp Phe Lys
    370                 375                 380
Gly His Cys Gly Pro Lys Tyr Pro Leu Leu Asn Lys Val His Asn Met
```

```
              385                 390                 395                 400
Ile Asn Gly Asp Glu Lys Asn Ser Tyr Glu Cys Leu Leu Gly Pro Ser
                405                 410                 415
Thr Thr Thr Pro Thr Pro Thr Thr Pro Ser Thr Thr Ser Thr Thr Thr
                420                 425                 430
Pro Thr Pro Thr Thr Thr Asp Ser Thr Ser Glu Thr Pro Lys Tyr Thr
                435                 440                 445
Thr Tyr Ile Asp Gly His Leu Ile Lys Cys Tyr Lys Gln Gly Tyr Leu
    450                 455                 460
Pro His Pro Thr Asp Val His Lys Tyr Leu Val Cys Glu Tyr Ile Ala
465                 470                 475                 480
Thr Pro Asn Gly Gly Trp Trp Val His Ile Met Asp Cys Pro Lys Gly
                485                 490                 495
Thr Arg Trp His Ala Thr Leu Lys Asn Cys Ile Gln Glu
                500                 505
```

<210> SEQ ID NO 39
<211> LENGTH: 1527
<212> TYPE: DNA
<213> ORGANISM: Dermatophagoides farinae

<400> SEQUENCE: 39

```
ttcttgaata caatttttta atgttgcgtg ccatctagtt ccttttggac aatccataat    60
gtgtacccac caaccaccgt ttggtgtggc aatatattca caaactaaat atttatgaac   120
atcagttgga tgtggaagat aaccttgttt atagcattta atcaaatgtc catcaatata   180
cgtagtgtat tttggtgttt cgcttgtgct atcggtggtg gtaggcgttg gtgtggtagt   240
cgaagtagtt gacggggtgg ttggtgttgg tgtggttgta cttgggccca aaagacattc   300
gtaagagttc ttttcatcac cattgatcat attgtgaact tgttcaaca atggatattt    360
cggtccgcaa tgacctttga aatcatcgtt ttccaatgac catatcataa cgccagagac   420
gcccaattct ttgagaaagg ccaacttgca tgatatacta ccagatcat cgtaaccaac    480
ccagatttta tcattatatc cgtatggagc attgtaatat tcatcgtatt gaatatgcca   540
ttcttctttc tggaataact gacacaattc gatgtatgag agaacacctt cttcaccagt   600
aataaaacca ggaggagaca tgcctttggc cggatcgcca gtttgactt tgcttcgatc    660
ttcgatgctc caagcacgac catagaatgg aacacccata caagtttgt ctcgagtagc    720
gccattgttc aaataatagt gcatggtgta gttgacattg aagtaagtgt gcaattcatc   780
cgtttcatcg ggtcgtttat acaacggagc attatggccg aaaacatttt cccatccgcc   840
atggtaatca taagtcatga cattcatcca atcgaacaat tggttcaatt ctttgagctc   900
ataagctacg tcaattttat ctttaccggg tgatactgcg gcagtcaaca agtagccgaa   960
aggttcaaat gcctctttaa gttctctaac taatgttaaa tagttttgtt tatcgatttt  1020
aggattgcct aaccgtgatc caggatattc ccaatccaaa tctaggccat cgaatttgta  1080
ttcttgcaaa aagtccaaaa ctgattgaac aaattgctga cgatatgttg gattggctgc  1140
catatccgaa tattttttctg aaccttcata ccaaccaccc aatgaaatca tggtggtcaa  1200
ttctggattc ttcaatctca agttgttgaa acgttcatac ccgtgttttt cccatgagtt  1260
atggttatca tcttgaaatg gatcaaaaac ttgaatggtg tatttgtatt catcgatttt  1320
agcaaaacca tacatcaaat gagtacattt gaaaggatca atatcttcaa ttgtgtatgg  1380
atcaacttta tgataaacgg accatgttcc aacataacat acgattcgca ttggattttt  1440
```

```
cgaataatta ttgtgatctc gtttagtggc cgcattcatc aagccaatgc aggcccatat    1500
acaaaacaat gcaaatgtcg ttttcat                                        1527

<210> SEQ ID NO 40
<211> LENGTH: 1470
<212> TYPE: DNA
<213> ORGANISM: Dermatophagoides farinae
<220> FEATURE:
<221> NAME/KEY: CDS
<222> LOCATION: (1)..(1470)

<400> SEQUENCE: 40 gcc act aaa cga gat cac aat aat tat tcg aaa aat cca atg cga atc      48
Ala Thr Lys Arg Asp His Asn Asn Tyr Ser Lys Asn Pro Met Arg Ile
 1               5                  10                  15 gta tgt tat gtt gga aca tgg tcc gtt tat cat aaa gtt gat cca tac      96
Val Cys Tyr Val Gly Thr Trp Ser Val Tyr His Lys Val Asp Pro Tyr
             20                  25                  30 aca att gaa gat att gat cct ttc aaa tgt act cat ttg atg tat ggt     144
Thr Ile Glu Asp Ile Asp Pro Phe Lys Cys Thr His Leu Met Tyr Gly
         35                  40                  45 ttt gct aaa atc gat gaa tac aaa tac acc att caa gtt ttt gat cca     192
Phe Ala Lys Ile Asp Glu Tyr Lys Tyr Thr Ile Gln Val Phe Asp Pro
     50                  55                  60 ttt caa gat gat aac cat aac tca tgg gaa aaa cac ggg tat gaa cgt     240
Phe Gln Asp Asp Asn His Asn Ser Trp Glu Lys His Gly Tyr Glu Arg
 65                  70                  75                  80 ttc aac aac ttg aga ttg aag aat cca gaa ttg acc acc atg att tca     288
Phe Asn Asn Leu Arg Leu Lys Asn Pro Glu Leu Thr Thr Met Ile Ser
                 85                  90                  95 ttg ggt ggt tgg tat gaa ggt tca gaa aaa tat tcg gat atg gca gcc     336
Leu Gly Gly Trp Tyr Glu Gly Ser Glu Lys Tyr Ser Asp Met Ala Ala
            100                 105                 110 aat cca aca tat cgt cag caa ttt gtt caa tca gtt ttg gac ttt ttg     384
Asn Pro Thr Tyr Arg Gln Gln Phe Val Gln Ser Val Leu Asp Phe Leu
        115                 120                 125 caa gaa tac aaa ttc gat ggc cta gat ttg gat tgg gaa tat cct gga     432
Gln Glu Tyr Lys Phe Asp Gly Leu Asp Leu Asp Trp Glu Tyr Pro Gly
    130                 135                 140 tca cgg tta ggc aat cct aaa atc gat aaa caa aac tat tta aca tta     480
Ser Arg Leu Gly Asn Pro Lys Ile Asp Lys Gln Asn Tyr Leu Thr Leu
145                 150                 155                 160 gtt aga gaa ctt aaa gag gca ttt gaa cct ttc ggc tac ttg ttg act     528
Val Arg Glu Leu Lys Glu Ala Phe Glu Pro Phe Gly Tyr Leu Leu Thr
                165                 170                 175 gcc gca gta tca ccc ggt aaa gat aaa att gac gta gct tat gag ctc     576
Ala Ala Val Ser Pro Gly Lys Asp Lys Ile Asp Val Ala Tyr Glu Leu
            180                 185                 190 aaa gaa ttg aac caa ttg ttc gat tgg atg aat gtc atg act tat gat     624
Lys Glu Leu Asn Gln Leu Phe Asp Trp Met Asn Val Met Thr Tyr Asp
        195                 200                 205 tac cat ggc gga tgg gaa aat gtt ttc ggc cat aat gct ccg ttg tat     672
Tyr His Gly Gly Trp Glu Asn Val Phe Gly His Asn Ala Pro Leu Tyr
    210                 215                 220 aaa cga ccc gat gaa acg gat gaa ttg cac act tac ttc aat gtc aac     720
Lys Arg Pro Asp Glu Thr Asp Glu Leu His Thr Tyr Phe Asn Val Asn
225                 230                 235                 240 tac acc atg cac tat tat ttg aac aat ggc gct act cga gac aaa ctt     768
Tyr Thr Met His Tyr Tyr Leu Asn Asn Gly Ala Thr Arg Asp Lys Leu
                245                 250                 255
```

|  |  |
|---|---|
| gtt atg ggt gtt cca ttc tat ggt cgt gct tgg agc atc gaa gat cga<br>Val Met Gly Val Pro Phe Tyr Gly Arg Ala Trp Ser Ile Glu Asp Arg<br>260                         265                     270 | 816 |
| agc aaa gtc aaa ctt ggc gat ccg gcc aaa ggc atg tct cct cct ggt<br>Ser Lys Val Lys Leu Gly Asp Pro Ala Lys Gly Met Ser Pro Pro Gly<br>275                       280                     285 | 864 |
| ttt att act ggt gaa gaa ggt gtt ctc tca tac atc gaa ttg tgt cag<br>Phe Ile Thr Gly Glu Glu Gly Val Leu Ser Tyr Ile Glu Leu Cys Gln<br>290                       295                     300 | 912 |
| tta ttc cag aaa gaa gaa tgg cat att caa tac gat gaa tat tac aat<br>Leu Phe Gln Lys Glu Glu Trp His Ile Gln Tyr Asp Glu Tyr Tyr Asn<br>305                       310                     315                     320 | 960 |
| gct cca tac gga tat aat gat aaa atc tgg gtt ggt tac gat gat ctg<br>Ala Pro Tyr Gly Tyr Asn Asp Lys Ile Trp Val Gly Tyr Asp Asp Leu<br>325                       330                     335 | 1008 |
| gct agt ata tca tgc aag ttg gcc ttt ctc aaa gaa ttg ggc gtc tct<br>Ala Ser Ile Ser Cys Lys Leu Ala Phe Leu Lys Glu Leu Gly Val Ser<br>340                       345                     350 | 1056 |
| ggc gtt atg ata tgg tca ttg gaa aac gat gat ttc aaa ggt cat tgc<br>Gly Val Met Ile Trp Ser Leu Glu Asn Asp Asp Phe Lys Gly His Cys<br>355                       360                     365 | 1104 |
| gga ccg aaa tat cca ttg ttg aac aaa gtt cac aat atg atc aat ggt<br>Gly Pro Lys Tyr Pro Leu Leu Asn Lys Val His Asn Met Ile Asn Gly<br>370                       375                     380 | 1152 |
| gat gaa aag aac tct tac gaa tgt ctt ttg ggc cca agt aca acc aca<br>Asp Glu Lys Asn Ser Tyr Glu Cys Leu Leu Gly Pro Ser Thr Thr Thr<br>385                       390                     395                     400 | 1200 |
| cca aca cca acc acc ccg tca act act tcg act acc aca cca acg cct<br>Pro Thr Pro Thr Thr Pro Ser Thr Thr Ser Thr Thr Thr Pro Thr Pro<br>405                       410                     415 | 1248 |
| acc acc acc gat agc aca agc gaa aca cca aaa tac act acg tat att<br>Thr Thr Thr Asp Ser Thr Ser Glu Thr Pro Lys Tyr Thr Thr Tyr Ile<br>420                       425                     430 | 1296 |
| gat gga cat ttg att aaa tgc tat aaa caa ggt tat ctt cca cat cca<br>Asp Gly His Leu Ile Lys Cys Tyr Lys Gln Gly Tyr Leu Pro His Pro<br>435                       440                     445 | 1344 |
| act gat gtt cat aaa tat tta gtt tgt gaa tat att gcc aca cca aac<br>Thr Asp Val His Lys Tyr Leu Val Cys Glu Tyr Ile Ala Thr Pro Asn<br>450                       455                     460 | 1392 |
| ggt ggt tgg tgg gta cac att atg gat tgt cca aaa gga act aga tgg<br>Gly Gly Trp Trp Val His Ile Met Asp Cys Pro Lys Gly Thr Arg Trp<br>465                       470                     475                     480 | 1440 |
| cac gca aca tta aaa aat tgt att caa gaa<br>His Ala Thr Leu Lys Asn Cys Ile Gln Glu<br>485                       490 | 1470 |

<210> SEQ ID NO 41
<211> LENGTH: 490
<212> TYPE: PRT
<213> ORGANISM: Dermatophagoides farinae

<400> SEQUENCE: 41

Ala Thr Lys Arg Asp His Asn Asn Tyr Ser Lys Asn Pro Met Arg Ile
1                  5                     10                  15

Val Cys Tyr Val Gly Thr Trp Ser Val Tyr His Lys Val Asp Pro Tyr
                 20                     25                     30

Thr Ile Glu Asp Ile Asp Pro Phe Lys Cys Thr His Leu Met Tyr Gly
                 35                     40                     45

Phe Ala Lys Ile Asp Glu Tyr Lys Tyr Thr Ile Gln Val Phe Asp Pro
 50                    55                     60

-continued

```
Phe Gln Asp Asp Asn His Asn Ser Trp Glu Lys His Gly Tyr Glu Arg
 65                  70                  75                  80

Phe Asn Asn Leu Arg Leu Lys Asn Pro Glu Leu Thr Thr Met Ile Ser
                 85                  90                  95

Leu Gly Gly Trp Tyr Glu Gly Ser Glu Lys Tyr Ser Asp Met Ala Ala
            100                 105                 110

Asn Pro Thr Tyr Arg Gln Gln Phe Val Gln Ser Val Leu Asp Phe Leu
        115                 120                 125

Gln Glu Tyr Lys Phe Asp Gly Leu Asp Leu Asp Trp Glu Tyr Pro Gly
130                 135                 140

Ser Arg Leu Gly Asn Pro Lys Ile Asp Lys Gln Asn Tyr Leu Thr Leu
145                 150                 155                 160

Val Arg Glu Leu Lys Glu Ala Phe Glu Pro Phe Gly Tyr Leu Leu Thr
                165                 170                 175

Ala Ala Val Ser Pro Gly Lys Asp Lys Ile Asp Val Ala Tyr Glu Leu
            180                 185                 190

Lys Glu Leu Asn Gln Leu Phe Asp Trp Met Asn Val Met Thr Tyr Asp
        195                 200                 205

Tyr His Gly Gly Trp Glu Asn Val Phe Gly His Asn Ala Pro Leu Tyr
210                 215                 220

Lys Arg Pro Asp Glu Thr Asp Glu Leu His Thr Tyr Phe Asn Val Asn
225                 230                 235                 240

Tyr Thr Met His Tyr Tyr Leu Asn Asn Gly Ala Thr Arg Asp Lys Leu
                245                 250                 255

Val Met Gly Val Pro Phe Tyr Gly Arg Ala Trp Ser Ile Glu Asp Arg
            260                 265                 270

Ser Lys Val Lys Leu Gly Asp Pro Ala Lys Gly Met Ser Pro Pro Gly
        275                 280                 285

Phe Ile Thr Gly Glu Glu Gly Val Leu Ser Tyr Ile Glu Leu Cys Gln
290                 295                 300

Leu Phe Gln Lys Glu Glu Trp His Ile Gln Tyr Asp Glu Tyr Tyr Asn
305                 310                 315                 320

Ala Pro Tyr Gly Tyr Asn Asp Lys Ile Trp Val Gly Tyr Asp Asp Leu
                325                 330                 335

Ala Ser Ile Ser Cys Lys Leu Ala Phe Leu Lys Glu Leu Gly Val Ser
            340                 345                 350

Gly Val Met Ile Trp Ser Leu Glu Asn Asp Asp Phe Lys Gly His Cys
        355                 360                 365

Gly Pro Lys Tyr Pro Leu Leu Asn Lys Val His Asn Met Ile Asn Gly
370                 375                 380

Asp Glu Lys Asn Ser Tyr Glu Cys Leu Leu Gly Pro Ser Thr Thr Thr
385                 390                 395                 400

Pro Thr Pro Thr Thr Pro Ser Thr Thr Ser Thr Thr Thr Pro Thr Pro
                405                 410                 415

Thr Thr Thr Asp Ser Thr Ser Glu Thr Pro Lys Tyr Thr Thr Tyr Ile
            420                 425                 430

Asp Gly His Leu Ile Lys Cys Tyr Lys Gln Gly Tyr Leu Pro His Pro
        435                 440                 445

Thr Asp Val His Lys Tyr Leu Val Cys Glu Tyr Ile Ala Thr Pro Asn
450                 455                 460

Gly Gly Trp Trp Val His Ile Met Asp Cys Pro Lys Gly Thr Arg Trp
465                 470                 475                 480
```

```
His Ala Thr Leu Lys Asn Cys Ile Gln Glu
              485                 490
```

```
<210> SEQ ID NO 42
<211> LENGTH: 1470
<212> TYPE: DNA
<213> ORGANISM: Dermatophagoides farinae

<400> SEQUENCE: 42
ttcttgaata caattttta atgttgcgtg ccatctagtt ccttttggac aatccataat      60
gtgtacccac caaccaccgt ttggtgtggc aatatattca caaactaaat atttatgaac    120
atcagttgga tgtggaagat aaccttgttt atagcattta atcaaatgtc catcaatata    180
cgtagtgtat tttggtgttt cgcttgtgct atcggtggtg gtaggcgttg gtgtggtagt    240
cgaagtagtt gacggggtgg ttggtgttgg tgtggttgta cttgggccca aaagacattc    300
gtaagagttc ttttcatcac cattgatcat attgtgaact tgttcaaca atggatattt     360
cggtccgcaa tgacctttga aatcatcgtt ttccaatgac catatcataa cgccagagac    420
gcccaattct ttgagaaagg ccaacttgca tgatatacta gccagatcat cgtaaccaac    480
ccagatttta tcattatatc cgtatggagc attgtaatat tcatcgtatt gaatatgcca    540
ttcttctttc tggaataact gacacaattc gatgtatgag agaacacctt cttcaccagt    600
aataaaacca ggaggagaca tgcctttggc cggatcgcca agtttgactt tgcttcgatc    660
ttcgatgctc caagcacgac catagaatgg aacacccata acaagtttgt ctcgagtagc    720
gccattgttc aaataatagt gcatggtgta gttgacattg aagtaagtgt gcaattcatc    780
cgtttcatcg ggtcgtttat acaacggagc attatggccg aaaacatttt cccatccgcc    840
atggtaatca taagtcatga cattcatcca atcgaacaat tggttcaatt ctttgagctc    900
ataagctacg tcaattttat ctttaccggg tgatactgcg gcagtcaaca agtagccgaa    960
aggttcaaat gcctctttaa gttctctaac taatgttaaa tagttttgtt tatcgatttt   1020
aggattgcct aaccgtgatc caggatattc ccaatccaaa tctaggccat cgaatttgta   1080
ttcttgcaaa aagtccaaaa ctgattgaac aaattgctga cgatatgttg gattggctgc   1140
catatccgaa tattttttctg aaccttcata ccaaccaccc aatgaaatca tggtggtcaa   1200
ttctggattc ttcaatctca agttgttgaa acgttcatac ccgtgttttt cccatgagtt   1260
atggttatca tcttgaaatg gatcaaaaac ttgaatggtg tatttgtatt catcgatttt   1320
agcaaaacca tacatcaaat gagtacattt gaaaggatca atatcttcaa ttgtgtatgg   1380
atcaactta tgataaacgg accatgttcc aacataacat acgattcgca ttggattttt   1440
cgaataatta ttgtgatctc gtttagtggc                                    1470
```

```
<210> SEQ ID NO 43
<211> LENGTH: 510
<212> TYPE: DNA
<213> ORGANISM: Dermatophagoides farinae
<220> FEATURE:
<221> NAME/KEY: CDS
<222> LOCATION: (1)..(510)

<400> SEQUENCE: 43 gat atg gaa cat ttt aca caa cat aag ggc aac gcc aaa gcc atg atc      48
Asp Met Glu His Phe Thr Gln His Lys Gly Asn Ala Lys Ala Met Ile
 1               5                  10                  15 gcc gtc ggt ggt tcg act atg tcc gat caa ttt tcc aag act gca gcg     96
Ala Val Gly Gly Ser Thr Met Ser Asp Gln Phe Ser Lys Thr Ala Ala
            20                  25                  30
```

```
gta gaa cat tat cgg gaa acg ttt gtt gtt agc aca gtt gat ctt atg         144
Val Glu His Tyr Arg Glu Thr Phe Val Val Ser Thr Val Asp Leu Met
         35                  40                  45 act cgt tat ggt ttc gat ggt gtc atg att gat tgg tct ggc atg caa         192
Thr Arg Tyr Gly Phe Asp Gly Val Met Ile Asp Trp Ser Gly Met Gln
 50                  55                  60 gcc aaa gat agt gat aat ttc att aaa ttg ttg gac aaa ttc gac gaa         240
Ala Lys Asp Ser Asp Asn Phe Ile Lys Leu Leu Asp Lys Phe Asp Glu
 65                  70                  75                  80 aag ttt gct cac acc tcg ttt gtg atg ggt gtt acc ttg ccg gca acg         288
Lys Phe Ala His Thr Ser Phe Val Met Gly Val Thr Leu Pro Ala Thr
                 85                  90                  95 atc gca tca tac gat aac tat aac att cct gcc atc tcc aac tat gtc         336
Ile Ala Ser Tyr Asp Asn Tyr Asn Ile Pro Ala Ile Ser Asn Tyr Val
                100                 105                 110 gat ttt atg aac gtg ctt agt ctg gat tac act gga tca tgg gcc cat         384
Asp Phe Met Asn Val Leu Ser Leu Asp Tyr Thr Gly Ser Trp Ala His
            115                 120                 125 acg gtc ggt cat gct tct ccg ttt cct gaa caa ctc aaa acg cta gaa         432
Thr Val Gly His Ala Ser Pro Phe Pro Glu Gln Leu Lys Thr Leu Glu
        130                 135                 140 gct tac cac aaa cga ggc gct cca cgt cat aag atg gtc atg gct gta         480
Ala Tyr His Lys Arg Gly Ala Pro Arg His Lys Met Val Met Ala Val
145                 150                 155                 160 cca ttt tat gca cgt acc tgg att ctc gag                                 510
Pro Phe Tyr Ala Arg Thr Trp Ile Leu Glu
                165                 170

<210> SEQ ID NO 44
<211> LENGTH: 170
<212> TYPE: PRT
<213> ORGANISM: Dermatophagoides farinae

<400> SEQUENCE: 44

Asp Met Glu His Phe Thr Gln His Lys Gly Asn Ala Lys Ala Met Ile
 1               5                  10                  15

Ala Val Gly Gly Ser Thr Met Ser Asp Gln Phe Ser Lys Thr Ala Ala
            20                  25                  30

Val Glu His Tyr Arg Glu Thr Phe Val Val Ser Thr Val Asp Leu Met
        35                  40                  45

Thr Arg Tyr Gly Phe Asp Gly Val Met Ile Asp Trp Ser Gly Met Gln
 50                  55                  60

Ala Lys Asp Ser Asp Asn Phe Ile Lys Leu Leu Asp Lys Phe Asp Glu
 65                  70                  75                  80

Lys Phe Ala His Thr Ser Phe Val Met Gly Val Thr Leu Pro Ala Thr
                 85                  90                  95

Ile Ala Ser Tyr Asp Asn Tyr Asn Ile Pro Ala Ile Ser Asn Tyr Val
                100                 105                 110

Asp Phe Met Asn Val Leu Ser Leu Asp Tyr Thr Gly Ser Trp Ala His
            115                 120                 125

Thr Val Gly His Ala Ser Pro Phe Pro Glu Gln Leu Lys Thr Leu Glu
        130                 135                 140

Ala Tyr His Lys Arg Gly Ala Pro Arg His Lys Met Val Met Ala Val
145                 150                 155                 160

Pro Phe Tyr Ala Arg Thr Trp Ile Leu Glu
                165                 170
```

```
<210> SEQ ID NO 45
<211> LENGTH: 510
<212> TYPE: DNA
<213> ORGANISM: Dermatophagoides farinae

<400> SEQUENCE: 45
ctcgagaatc caggtacgtg cataaaatgg tacagccatg accatcttat gacgtggagc    60
gcctcgtttg tggtaagctt ctagcgtttt gagttgttca ggaaacggag aagcatgacc   120
gaccgtatgg gcccatgatc cagtgtaatc cagactaagc acgttcataa aatcgacata   180
gttggagatg gcaggaatgt tatagttatc gtatgatgcg atcgttgccg gcaaggtaac   240
acccatcaca aacgaggtgt gagcaaactt ttcgtcgaat ttgtccaaca atttaatgaa   300
attatcacta tctttggctt gcatgccaga ccaatcaatc atgacaccat cgaaaccata   360
acgagtcata agatcaactg tgctaacaac aaacgtttcc cgataatgtt ctaccgctgc   420
agtcttggaa aattgatcgg acatagtcga accaccgacg gcgatcatgg ctttggcgtt   480
gcccttatgt tgtgtaaaat gttccatatc                                    510

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:   Synthetic
      Primer
<220> FEATURE:
<223> OTHER INFORMATION: At location 15,  n = a, c t or g

<400> SEQUENCE: 46
gaaccaaaaa chgtntgyta ytayg                                          25

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 47
gtaaaacgac ggccagt                                                   17

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 48
gatatggaac atttyachca acayaargg                                      29

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 49
gtaatacgac tcactatagg gc                                             22
```

DERMATOPHAGOIDES PROTEINS AND USES THEREOF

CROSS REFERENCE TO RELATED APPLICATIONS

This application is a divisional of U.S. application Ser. No. 09/292,225, filed Apr. 15, 1999 now U.S. Pat. No. 6,455,686, entitled "NOVEL DERMATOPHAGOIDES NUCLEIC ACID MOLECULES, PROTEINS AND USES THEREOF".

FIELD OF THE INVENTION

The present invention relates to high molecular weight Dermatophagoides proteins, nucleic acid molecules and therapeutic and diagnostic reagents derived from such proteins.

BACKGROUND OF THE INVENTION

Immunoglobulin E (IgE) mediated allergic symptoms afflict many animals. IgE antibody production in an animal can induce pathogenic IgE responses including, for example, atopic disease, asthma and rhinitis. Allergens are proteins or peptides characterized by their ability to induce a pathogenic IgE response in susceptible individuals.

House dust mite (e.g., *Dermatophagoides farinae* and *Dermatophagoides pteronyssinus*; Der f and Der p, respectively) allergens are major causative agents associated with IgE-mediated pathogenesis. Previous investigators have identified two major groups of dust mite allergens in humans, group I (Der f I and Der p I, Mr 25,000) and group 2 (Der f II and Der p II, Mr 14,000); reviewed in Chapman, et al., *Allergy*, vol. 52, pp.37-379, 1997. Prior investigators have disclosed nucleotide and/or amino acid sequences for: Der f I, Der f II, Der p I and Der p II, U.S. Pat. No. 5,552,142, to Thomas et al., issued Sep. 3, 1996, U.S. Pat. No. 5,460,977, to Ando et al., issued Oct. 24, 1995, PCT Patent Publication No. WO 95/28424, by Chen et al., published Oct. 26, 1995, U.S. Pat. No. 5,433,948, to Thomas et al., issued Jul. 18, 1995, PCT Patent Publication No. WO 93/08279, by Garmen et al., published Mar. 4, 1993, or Chapman, ibid.; Der p III, PCT Patent Publication No. WO 95/15976, by Thomas et al., published Jun. 15, 1995; Der p VII, PCT Patent Publication No. WO 94/20614, by Thomas et al., published Sep. 15, 1994; a 40-kilodalton (kd) Der f allergen, U.S. Pat. No. 5,405,758, to Oka et al., issued Apr. 11, 1995, U.S. Pat. No. 5,314,991, to Oka et al., issued May 24, 1994; a 70-kd Der f allergen which is a heat shock protein (Hsp70), Aki et al., *J. Biochem.*, vol. 115, pp. 435-440, 1994; or Noli et al., *Vet. Immunol. Immunopath.*, vol. 52, pp. 147-157, 1996; and a 98-kd Der f paramyosin-like allergen, Tsai et al, *J. Allergy Clin. Immunol.*, vol. 102, pp. 295-303, 1998. None of these published sequences indicates, suggests or predicts any of the mite allergic nucleic acid molecules or proteins of the present invention, nor the relevance of such proteins as being immunoreactive with IgE antibodies in canine, feline, or human sera.

Products and processes of the present invention are needed in the art that provide specific detection and treatment of mite allergy.

SUMMARY OF THE INVENTION

The present invention relates to novel proteins having molecular weights of about 60 kilodaltons (kd or kD), 70 kD, or from about 98 kD to about 109 kD. Such proteins include at least one epitope of a protein allergen of a mite of the genus *Dermatophagoides* and are designated herein as Der HMW-map proteins. Preferred proteins are *Dermatophagoides farinae* or *Dermatophagoides pteronyssius* proteins. The present invention also provides proteins that are fragments or peptides of full-length or mature proteins, as well as antibodies, mimetopes or muteins of any of such proteins. The present invention also provides nucleic acid molecules encoding any of such proteins, as well as complements thereof. The present invention also includes methods to obtain such proteins, nucleic acid molecules, antibodies, mimetopes or muteins, as well as methods to use such compounds in diagnostic or therapeutic applications. The present invention also relates to reagents comprising non-proteinaceous epitopes that bind to IgE in mite-allergic dogs and/or cats as well as to antibodies raised against such epitopes. The present invention also relates to therapeutic compositions or assay kits comprising such non-proteinaceous epitopes, as well as to methods to identify and/or desensitize an animal susceptible to an allergic response to a mite, comprising the use of non-proteinaceous epitopes of the present invention.

One embodiment of the present invention is at least one of the following isolated nucleic acid molecules: (a) a nucleic acid molecule comprising at least about 150 nucleotides, wherein such a nucleic acid molecule hybridizes, in a solution comprising 1×SSC and 0% formamide, at a temperature of about 50° C., to a nucleic acid molecule comprising at least one of the following nucleic acid sequences: SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45, and a nucleic acid sequence encoding a protein comprising the amino acid sequence of SEQ ID NO:33 and a complement thereof; and (b) a nucleic acid molecule comprising a fragment of any of the nucleic acid molecules of (a) wherein the fragment comprises at least about 15 nucleotides. The present invention also includes recombinant molecules, recombinant viruses and recombinant cells comprising such nucleic acid sequences as well as methods to produce them.

Another embodiment of the present invention is an isolated protein encoded by at least one of the following nucleic acid molecules: (a) a nucleic acid molecule comprising at least about 150 nucleotides, wherein such a nucleic acid molecule hybridizes, in a solution comprising 1×SSC and 0% formamide, at a temperature of about 50° C., to a nucleic acid molecule comprising at least one of the following nucleic acid sequences: SEQ ID NO:16, SEQ ID NO:19, SEQ ID NO:22, SEQ ID NO:36, SEQ ID NO:39, SEQ ID NO:42, SEQ ID NO:45, and a complement of a nucleic acid sequence encoding a protein comprising the amino acid sequence SEQ ID NO:33; and (b) a nucleic acid molecule comprising a fragment of any of the nucleic acid molecules of (a), wherein the fragment comprises at least about 15 nucleotides. An isolated protein of the present invention can also be encoded by a nucleic acid molecule that hybridizes under stringent hybridization conditions with the complement of a nucleic acid molecule that encodes a protein having at least one of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, and SEQ ID NO:44. The present invention also includes an antibody that selectively binds to a protein of the present invention as well as methods to produce and use such proteins or antibodies.

The present invention also includes a therapeutic composition for treating an allergic response to a mite. Such a therapeutic composition includes at least one of the following desensitizing compounds: (a) an isolated nucleic acid molecule of the present invention; (b) an isolated mite allergenic protein of the present invention; (c) a mimetope of such a mite allergenic protein; (d) a mutein of such a mite allergenic protein; (e) an antibody to such a mite allergic protein; and (f) an inhibitor of binding of such a mite allergic protein to IgE. Also included is a method to desensitize a host animal to an allergic response to a mite. Such a method includes the step of administering to the animal a therapeutic composition of the present invention.

One embodiment of the present invention is an assay kit for testing if an animal is susceptible to or has an allergic response to a mite. Such a kit includes an isolated protein of the present invention and a means for determining if the animal is susceptible to or has that allergic response. Such a means includes use of such a protein to identify animals susceptible to or having allergic responses to mites. The present invention also includes a method to identify an animal susceptible to or having an allergic response to a mite. Such a method includes the steps of: (a) contacting an isolated protein of the present invention with antibodies of an animal; and (b) determining immunocomplex formation between the protein and the antibodies, wherein formation of the immunocomplex indicates that the animal is susceptible to or has such an allergic response.

The present invention includes a reagent that comprises a non-proteinaceous epitope having at least one of the following identifying characteristics: (a) the epitope is resistant to β-elimination of peptides; (b) the epitope is resistant to Proteinase-K digestion; and (c) the epitope is reactive to a test designed to detect glycosylated proteins. Such an epitope binds to at least one of the following antibodies: canine IgE from dogs allergic to mites and feline IgE from cats allergic to mites. Also included is an isolated antibody that selectively binds such a non-proteinaceous epitope as well as derivatives of such an epitope.

The present invention also relates to therapeutic compositions and assay kits comprising a non-proteinaceous epitope of the present invention, as well as methods to identify and/or desensitize an animal susceptible to an allergic response to a mite, comprising the use of a non-proteinaceous epitope of the present invention.

DETAILED DESCRIPTION OF THE INVENTION

Figure 1:
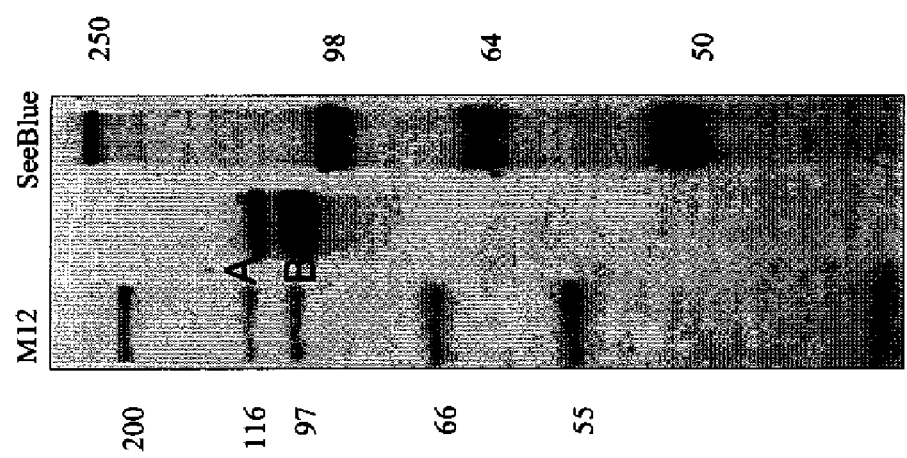
FIG. 1 illustrates high molecular weight Der f proteins resolved by 12% Tris-Glycine SDS-PAGE.

The present invention provides for isolated proteins having molecular weights ranging from about 60 kilodaltons (kD) to about 109 kD, that include at least one epitope of a protein allergen of a mite of the genus *Dermatophagoides*, in particular a mite of the species *Dermatophagoides farinae* and/or *Dermatophagoides pteronyssius*. Such proteins are referred to herein as Der HMW-map proteins. The present invention further includes methods to isolate and identify nucleic acid molecules encoding DerHMW-map proteins, antibodies directed against Der HMW-map proteins and inhibitors of Der HMW-map protein activity. As used herein, the term isolated Der HMW-map proteins refers to Der HMW-map proteins derived from *Dermatophagoides*, and more preferably from *Dermatophagoides farinae* and/or *Dermatophagoides pteronyssius* and, as such, can be obtained from its natural source or can be produced using, for example, recombinant nucleic acid technology or chemical synthesis. Also included in the present invention is the use of this protein and antibodies in a method to detect immunoglobulin that specifically binds to Der HMW-map proteins, to treat pathogenesis against mite allergens, and in other applications, such as those disclosed below. The products and processes of the present invention are advantageous because they enable the detection of anti-Der HMW-map antibodies in fluids of animals and the inhibition of IgE or Der HMW-map protein activity associated with disease.

One embodiment of the present invention is an isolated *Dermatophagoides* allergenic composition including: (a) a composition produced by a method comprising: (1) applying soluble proteins of a *Dermatophagoides* extract to a gel filtration column; (2) collecting excluded protein from the gel filtration column and applying the excluded protein to an anion exchange column; and (3) eluting proteins bound to the anion exchange column with about 0.3 M Tris-HCl, pH 8 to obtain the *Dermatophagoides* allergenic composition; and (b) a composition comprising a peptide of a protein produced in accordance with step (a), in which the allergenic composition is capable of a biological function including binding to IgE, stimulating a B lymphocyte response and stimulating a T lymphocyte response. Such *Dermatophagoides* allergenic composition is also referred to herein as a Der HMW-map composition. A suitable gel filtration column includes any gel filtration column capable of excluding proteins having a molecular weight between about 50 kD and about 150 kD. A preferred gel filtration column includes, but is not limited to a Sephacryl S-100 column. A suitable anion exchange column includes any anion exchange column capable of binding to a protein having a pI of less than about pI 6. A preferred anion exchange column includes, but is not limited to a Q-Sepharose column. As used herein, "stimulating a B lymphocyte response" refers to increasing a humoral immune response in an animal that is induced preferentially by a Der HMW-map of the present invention and involves the activity of a B lymphocyte in the animal. As used herein, "stimulating a T lymphocyte response" refers to increasing a cellular immune response in an animal that is induced preferentially by a Der HMW-map of the present invention and involves the activity of a T lymphocyte in the animal.

One embodiment of the present invention is an isolated protein that includes a Der HMW-map protein. It is to be noted that the term "a" or "an" entity refers to one or more of that entity; for example, a protein, a nucleic acid molecule, an antibody, an inhibitor, a compound or a therapeutic composition refers to "one or more" or "at least one" protein, nucleic acid molecule, antibody, inhibitor, compound or therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, a Der HMW-map protein can be a fill-length protein or any homolog of such a protein. As used herein, a protein can be a polypeptide or a peptide, as the terms are used by those of skill in the art. Preferably, a Der HMW-map protein comprises at least a portion of a Der HMW-map protein that comprises at least one epitope recognized by an IgE antibody (i.e., a protein of the present invention binds to an IgE antibody), an antibody on the surface of a B lymphocyte and/or a T cell receptor in the presence of a major histocompatability complex (MHC) molecule from an animal demonstrating IgE-mediated pathogenesis to a Der HMW-map protein.

A peptide of the present invention includes a Der HMW-map protein of the present invention that is capable of binding to IgE, desensitizing an animal against mite allergen, stimulating a B lymphocyte response, and/or stimulating a T lymphocyte response. Preferably, a peptide of the present invention comprises a B lymphocyte epitope or a T lymphocyte epitope. A peptide having a B lymphocyte epitope can bind to an antibody. A peptide having a T lymphocyte epitope can bind to a MHC molecule in such a manner that the peptide can stimulate a T lymphocyte through a T cell receptor. According to the present invention, a peptide comprising a B lymphocyte epitope can be from about 4 residues to about 50 residues in length, preferably from about 5 residues to about 20 residues in length. According to the present invention, a peptide comprising a T lymphocyte epitope can be from about 4 residues to about 20 residues in length, preferably from about 8 residues to about 16 residues in length.

A Der HMW-map protein of the present invention, including a homolog, can be identified in a straight-forward manner by the protein's ability to induce an allergic response to Der HMW-map protein. Examples of Der HMW-map protein homologs include Der HMW-map protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog is capable of inducing an allergic response to a natural Der HMW-map protein.

Der HMW-map protein homologs can be the result of natural allelic variation or natural mutation. Der HMW-map protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

One embodiment of the present invention is a Der HMW-map gene that includes the nucleic acid sequence SEQ ID NO:14, SEQ ID NO:16, SEQ ID NO:17, SEQ ID NO:19, SEQ ID NO:20 SEQ ID NO:22, SEQ ID NO:34, SEQ ID NO:36, SEQ ID NO:37, SEQ ID NO:39, SEQ ID NO:40, SEQ ID NO:42, SEQ ID NO:43, and SEQ ID NO:45 as well as the complements of any of these nucleic acid sequences. These nucleic acid sequences are further described herein. For example, nucleic acid sequence SEQ ID NO:14 represents the deduced sequence of the coding strand of a cDNA (complementary DNA) denoted herein as Der HMW-map gene nucleic acid molecule $nDerf98_{1752}$, the production of which is disclosed in the Examples. Nucleic acid molecule $nDerf98_{1752}$ comprises an apparently full-length coding region. The complement of SEQ ID NO:14 (represented herein by SEQ ID NO:16) refers to the nucleic acid sequence of the strand complementary to the strand having SEQ ID NO:14, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:14 (as well as other nucleic acid and protein sequences presented herein) represents an apparent nucleic acid sequence of the nucleic acid molecule encoding a Der HMW-map protein of the present invention.

In another embodiment, a Der HMW-map gene or nucleic acid molecule can be an allelic variant that includes a similar but not identical sequence to SEQ ID NO:14 or SEQ ID NO:16, or any other Der HMW-map nucleic acid sequence cited herein. For example, an allelic variant of a Der HMW-map gene including SEQ ID NO:14 or SEQ ID NO:16, is a gene that occurs at essentially the same locus (or loci) in the genome as the gene including SEQ ID NO:14 and SEQ ID NO:16, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given dust mite such as *Dermatophagoides*, since the respective genomes are diploid, and sexual reproduction will result in the reassortment of alleles.

In one embodiment of the present invention, an isolated Der HMW-map protein is encoded by a nucleic acid molecule that hybridizes under stringent hybridization conditions to a gene encoding a Der HMW-map protein. The minimal size of a Der HMW-map protein of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the Der HMW-map nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a Der HMW-map protein is typically at least about 12 nucleotides to about 15 nucleotides in length if the nucleic acid molecule is GC-rich and at least about 15 to about 17 bases in length if it is AT-rich. The minimal size of a nucleic acid molecule used to encode a Der HMW-map protein homolog of the present invention is from about 12 to about 18 nucleotides in length, preferably about 12 nucleotides, or about 15 nucleotides, or about 18 nucleotides in length. Thus, the minimal size of a Der HMW-map protein homolog of the present invention is from about 4 to about 6 amino acids in length. There is no limit, other than a practical limit, on the maximal size of a nucleic acid molecule encoding a Der HMW-map protein of the present invention because a nucleic acid molecule of the present invention can include a portion of a gene, an entire gene, or multiple genes. The preferred size of a protein encoded by a nucleic acid molecule of the present invention depends on whether a full-length, fusion, multivalent, or functional portion of such a protein is desired. Preferably, the preferred size of a protein encoded by a nucleic acid molecule of the present invention is a portion of the protein that induces an immune response which is about 30 amino acids, more preferably about 35 amino acids and even more preferably about 44 amino acids in length.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° C. + 16.6 \log M + 0.41(\% G+C) - 500/n - 0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a *Dermatophagoides farinae* and/or *Dermatophagoides pteronyssius* nucleic acid molecule of about 150 bp in length, the following conditions could preferably be used. The average G+C content of *Dermatophagoides farinae* and *Dermatophagoides pteronyssius* DNA is about 39%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1×SSC and 0% formamide, the $T_m$ of perfect hybrids would be about 80° C.:

$$81.5° C. + 16.6 \log(0.15M) + (0.41 \times 39) - (500/150) - (0.61 \times 0) = 80.4° C.$$

Thus, to achieve hybridization with nucleic acid molecules having about 30% base-pair mismatch, hybridization washes would be carried out at a temperature of about 50° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 50° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

One embodiment of the present invention includes Der HMW-map proteins. In one embodiment, Der HMW-map proteins of the present invention include proteins that, when submitted to reducing 12% Tris glycine SDS-PAGE, migrate as bands at a molecular weight of from about 98 kD to about 109 kD, as shown in FIG. 1. The bands in FIG. 1 are obtained when proteins are collected from *Dermataphagoides farinae* mites using the method described in detail in Example 1. Preferably, Der HMW-map proteins of the present invention includes proteins having a molecular weight ranging from about 90 kD to about 120 kD, and more preferably from about 98 kD to about 109 kD. Preferred Der HMW-map proteins of the present invention include mapA and mapB, the identification of which is described in the Examples section.

Figure 2:
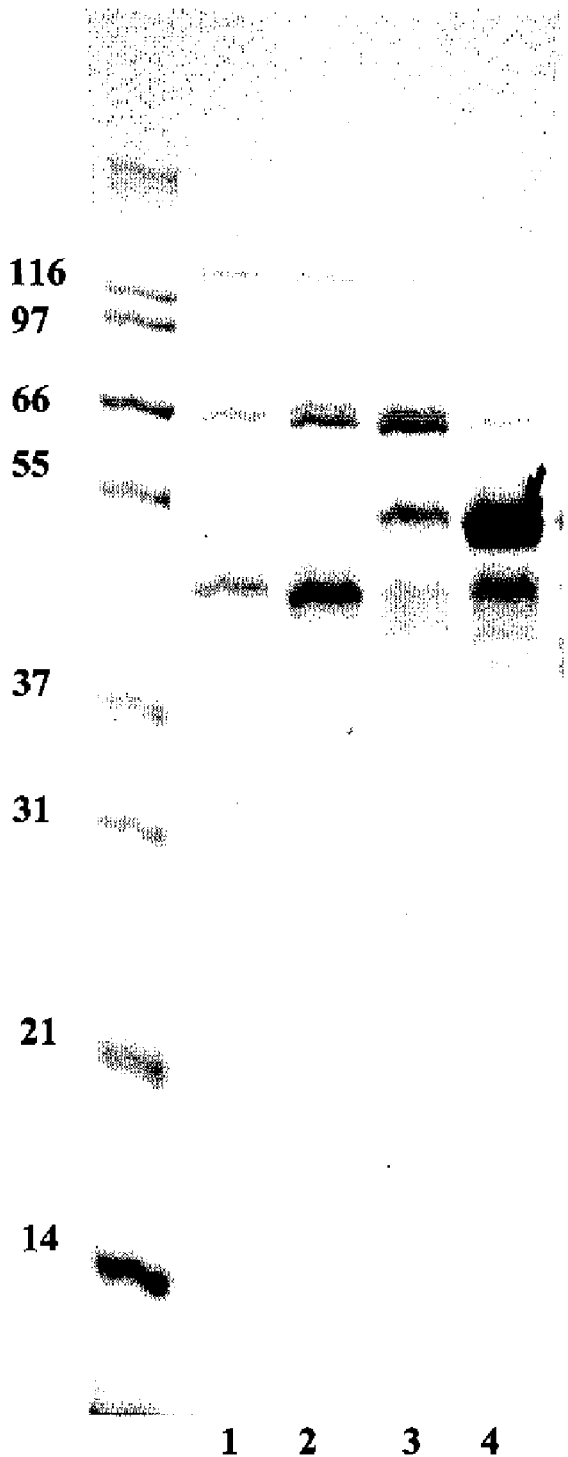
FIG. 2 illustrates an about 60 kD Der f protein resolved by 14% Tris-Glycine SDS-PAGE.

In another embodiment, Der HMW-map proteins of the present invention include proteins that, when submitted to reducing 14% Tris glycine SDS-PAGE, migrate as a band at a molecular weight of about 60 kD, as shown in FIG. 2. The band in FIG. 2 is obtained when proteins are collected from *Dermataphagoides farinae* mites using the method described in detail in Example 9. Preferably, Der HMW-map proteins of the present invention includes proteins having a molecular weight of about 60 kD. Preferred Der HMW-map proteins of the present invention include mapD, the identification of which is described in the Examples section.

In another embodiment, a preferred Der HMW-map protein includes a protein encoded by a nucleic acid molecule which is at least about 50 nucleotides, or about 150 nucleotides, and which hybridizes under conditions which preferably allow about 40% or less base pair mismatch, more preferably under conditions which allow about 35% or less base pair mismatch, more preferably under conditions which allow about 30% or less base pair mismatch, more preferably under conditions which allow about 25% or less base pair mismatch, more preferably under conditions which allow about 20% or less base pair mismatch, more preferably under conditions which allow about 15% or less base pair mismatch, more preferably under conditions which allow about 10% or less base pair mismatch and even more preferably under conditions which allow about 5% or less base pair mismatch with a nucleic acid molecule selected from the group consisting of SEQ ID NO:16, SEQ ID NO:19, SEQ ID NO:22, SEQ ID NO:36, SEQ ID NO:39, SEQ ID NO:42, SEQ ID NO:45 and a nucleic acid sequence encoding a protein comprising the amino acid sequence SEQ ID NO:33 the complement thereof.

Another embodiment of the present invention includes a Der HMW-map protein encoded by a nucleic acid molecule selected from the group consisting of: a nucleic acid molecule comprising at least about 150 nucleotides, wherein said nucleic acid molecule comprising at least about 150 nucleotides hybridizes, in a solution comprising 1×SSC and 0% formamide, at a temperature of about 50° C., to a nucleic acid sequence selected from the group consisting of SEQ ID NO:16, SEQ ID NO:19, SEQ ID NO:22, SEQ ID NO:36, SEQ ID NO:39, SEQ ID NO:42, SEQ ID NO:45, and a complement of a nucleic acid sequence encoding a protein comprising the amino acid sequence SEQ ID NO:33; and a nucleic acid molecule comprising a fragment of any of said nucleic acid molecules comprising at least about 15 nucleotides.

Yet another preferred Der HMW-map protein of the present invention includes a protein encoded by a nucleic acid molecule which is preferably at least about 60% identical, more preferably at least about 65% identical, more preferably at least about 70% identical, more preferably at least about 75% identical, more preferably at least about 80% identical, more preferably at least about 85% identical, more preferably at least about 90% identical and even more preferably at least about 95% identical to a nucleic acid molecule having the nucleic acid sequence SEQ ID NO:14, SEQ ID NO:17, SEQ ID NO:20, SEQ ID NO:34, SEQ ID NO:37, SEQ ID NO:40, SEQ ID NO:43, and/or a complement of a nucleic acid sequence encoding a protein comprising the amino acid sequence SEQ ID NO:33; also preferred are fragments of such proteins. Percent identity as used herein is determined using the Compare function by maximum matching within the program DNAsis Version 2.1 using default parameters.

Additional preferred Der HMW-map proteins of the present invention include proteins having the amino acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, SEQ ID NO:44, and proteins comprising homologs of a protein having the amino acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, SEQ ID NO:44 in which such a homolog comprises at least one epitope that elicits an immune response against a protein having an amino acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, SEQ ID NO:44 Likewise, also preferred are proteins encoded by nucleic acid molecules encoded by nucleic acid molecules having nucleic acid sequence SEQ ID NO:14, SEQ ID NO:17, SEQ ID NO:20, SEQ ID NO:34, SEQ ID NO:37, SEQ ID NO:40, SEQ ID NO:43 and/or a nucleic acid sequence encoding a protein comprising the amino acid sequence SEQ ID NO:33, or by homologs thereof.

A preferred isolated protein of the present invention is a protein encoded by at least one of the following nucleic acid molecules: $nDerf98_{1752}$, $nDerf98_{1665}$, $nDerf98_{1608}$, $nDerp98_{1621}$, $nDerp98_{1527}$, $nDerp98_{1470}$, $nDerf60_{510}$, or allelic variants of any of these nucleic acid molecules. Another preferred isolated protein is encoded by a nucleic acid molecule having nucleic acid sequence SEQ ID NO:14, SEQ ID NO:17, SEQ ID NO:20, SEQ ID NO:34, SEQ ID NO:37, SEQ ID NO:40, SEQ ID NO:43; or a protein encoded by an allelic variant of any of these listed nucleic acid molecule.

Translation of SEQ ID NO:14, the coding strand of $nDerf98_{1752}$, yields a protein of about 555 amino acids, denoted herein as $PDerf98_{555}$, the amino acid sequence of which is presented in SEQ ID NO:15, assuming a first in-frame codon extending from nucleotide 1 to nucleotide 3 of SEQ ID NO:14. The complementary strand of SEQ ID NO:14 is presented herein as SEQ ID NO:16. The amino acid sequence of $PDerf98_{555}$ is encoded by the nucleic acid molecule $nDerf98_{1665}$, having a coding strand denoted SEQ ID NO:17 and a complementary strand denoted SEQ ID NO:19. Analysis of SEQ ID NO:15 suggests the presence of a signal peptide spanning from about amino acid 1 through about amino acid 19. The proposed mature protein, denoted herein as $PDerf98_{536}$, contains about 536 amino acids, the sequence of which is represented herein as SEQ ID NO:21, and is encoded by a nucleic acid molecule referred to herein as $nDerf98_{1608}$, represented by SEQ ID NO:20, the coding strand, and SEQ ID NO:22, the complementary strand.

Translation of SEQ ID NO:34, the coding strand of $nDerp98_{1621}$, yields a protein of about 509 amino acids, denoted herein as $PDerp98_{509}$, the amino acid sequence of which is presented in SEQ ID NO:35, assuming a first in-frame codon extending from nucleotide 14 to nucleotide 16 of SEQ ID NO:34. The complementary strand of SEQ ID NO:34 is presented herein as SEQ ID NO:36. The amino acid sequence of $PDerpf98_{509}$ is encoded by the nucleic acid molecule $nDerp98_{1527}$, having a coding strand denoted SEQ ID NO:37 and a complementary strand denoted SEQ ID NO:39. Analysis of SEQ ID NO:35 suggests the presence of a signal peptide spanning from about amino acid 1 through about amino acid 19. The proposed mature protein, denoted herein as $PDerp98_{490}$, contains about 490 amino acids, the sequence of which is represented herein as SEQ ID NO:41, and is encoded by a nucleic acid molecule referred to herein as $nDerp98_{1470}$, represented by SEQ ID NO:40, the coding strand, and SEQ ID NO:42, the complementary strand.

Translation of SEQ ID NO:43, the coding strand of $nDerf60_{510}$, a nucleic acid molecule encoding a portion of the *D. farinae* 60-kD antigen protein yields a protein of about 170 amino acids, denoted herein as $PDerf60_{170}$, the amino acid sequence of which is presented as SEQ ID NO:44, assuming a first in-frame codon extending from nucleotide 1 to nucleotide 3 of SEQ ID NO:43. The complementary sequence to SEQ ID NO:43 is presented herein as SEQ ID NO:45.

Preferred Der HMW-map proteins of the present invention include proteins that are at least about 45%, preferably at least about 50%, more preferably at least about 55%, even more preferably at least about 60%, even more preferably at least about 65%, even more preferably at least about 70%, even more preferably at least about 75%, even more preferably at least about 80%, even more preferably at least about 85%, even more preferably at least about 90%, and even more preferably about 95% identical to $PDerf98_{555}$. More preferred is a Der HMW-map protein comprising $PDerf98_{555}$, $PDerf98_{536}$, $PDerp98_{509}$, $PDerp98_{490}$, and/or $PDerf60_{170}$; and proteins encoded by allelic variants of nucleic acid molecules encoding proteins $PDerf98_{555}$, $PDerf98_{536}$, $PDerp98_{509}$, $PDerp98_{490}$, and/or $PDerf60_{170}$.

Other preferred Der HMW-map proteins of the present invention include proteins having amino acid sequences that are at least about 45%, preferably at least about 50%, more preferably at least about 55%, even more preferably at least about 60%, even more preferably at least about 65%, even more preferably at least about 70%, even more preferably at least about 75%, even more preferably at least about 80%, even more preferably at least about 85%, even more preferably at least about 90%, and even more preferably about 95% identical to amino acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, and/or SEQ ID NO:44. More preferred are Der HMW-map proteins comprising amino acid sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, and/or SEQ ID NO:44; and Der HMW-map proteins encoded by allelic variants of nucleic acid molecules encoding Der HMW-map proteins having amino acid sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, and/or SEQ ID NO:44.

In one embodiment of the present invention, Der HMW-map proteins comprise amino acid sequence SEQ ID NO:15, SEQ ID NO:35, and/or SEQ ID NO:44 (including, but not limited to, the proteins consisting of amino acid sequence SEQ ID NO:15, SEQ ID NO:35, and/or SEQ ID NO:44, fragments thereof, fusion proteins and multivalent proteins), and proteins encoded by allelic variants of nucleic acid molecules encoding proteins having amino acid sequence SEQ ID NO:15, SEQ ID NO:35, and/or SEQ ID NO:44.

In one embodiment, a preferred Der HMW-map protein comprises an amino acid sequence of at least about 35 amino acids in length, preferably at least about 50 amino acids in length, more preferably at least about 100 amino acids in length, more preferably at least about 200 amino acids in length, even more preferably at least about 250 amino acids in length. Within this embodiment, a preferred Der HMW-map protein of the present invention has an amino acid sequence comprising at least a portion of SEQ ID NO:15. In another embodiment, a preferred Der HMW-map protein comprises a full-length protein, i.e., a protein encoded by a full-length coding region.

Additional preferred Der HMW-map proteins of the present invention include proteins encoded by nucleic acid molecules comprising at least a portion of $nDerf98_{1752}$, $nDerf98_{1665}$, $nDerf98_{1608}$, $nDerp98_{1621}$, $nDerp98_{1527}$, $nDerp98_{1470}$, and $nDerf60_{510}$, as well as well as Der HMW-map proteins encoded by allelic variants of such nucleic acid molecules.

Also preferred are Der HMW-map proteins encoded by nucleic acid molecules having nucleic acid sequences comprising at least a portion of SEQ ID NO:14, SEQ ID NO:17, SEQ ID NO:20, SEQ ID NO:34, SEQ ID NO:37, SEQ ID NO:40 SEQ ID NO:43 and/or a nucleic acid sequence encoding a protein comprising the amino acid sequence SEQ ID NO:33, as well as allelic variants of these nucleic acid molecules.

In another embodiment, a preferred Der HMW-map protein of the present invention is encoded by a nucleic acid molecule comprising at least about 12 nucleotides, preferably at least about 16 nucleotides, more preferably at least about 18 nucleotides, more preferably at least about 20 nucleotides, more preferably at least about 25 nucleotides, more preferably at least about 50 nucleotides, more preferably at least about 100 nucleotides, more preferably at least about 350 nucleotides, more preferably at least about 450 nucleotides, more preferably at least about 500 nucleotides, and even more preferably at least about 800 nucleotides. Within this embodiment is a Der HMW-map protein encoded by at least a portion $nDerf98_{1752}$, $nDerp98_{1621}$, and/or $nDerf60_{510}$ or by an allelic variant of these nucleic acid molecules. In yet another embodiment, a preferred Der HMW-map protein of the present invention is encoded by a nucleic acid molecule comprising an apparently full-length Der HMW-map coding region, i.e., a nucleic acid molecule encoding an apparently full-length Der HMW-map protein.

One embodiment of a Der HMW-map protein of the present invention is a fusion protein that includes a Der HMW-map protein-containing domain attached to one or more fusion segments. Suitable fusion segments for use with the present invention include, but are not limited to, segments that can: enhance a protein's stability; act as an immunopotentiator to enhance an immune response against a Der HMW-map protein, reduce an IgE response against a Der HMW-map protein; and/or assist purification of a Der HMW-map protein (e.g., by affinity chromatography). A suitable fusion segment can be a domain of any size that has the desired function (e.g., imparts increased stability, imparts increased immunogenicity to a protein, reduces an IgE response, and/or simplifies purification of a protein). Fusion segments can be joined to amino and/or carboxyl termini of the Der HMW-map protein-containing domain of the protein and can be susceptible to cleavage in order to enable straight-forward recovery of a Der HMW-map protein. Fusion proteins are preferably produced by culturing a recombinant cell transformed with a fusion nucleic acid molecule that encodes a protein including the fusion segment attached to either the carboxyl and/or amino terminal end of a Der HMW-map protein-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); a "tag" domain (e.g., at least a portion of -galactosidase, a strep tag peptide, other domains that can be purified using compounds that bind to the domain, such as monoclonal antibodies); and/or a linker and enzyme domain (e.g., alkaline phosphatase domain connected to a Der HMW-map protein by a linker). More preferred fusion segments include metal binding domains, such as a poly-histidine segment; a maltose binding domain; a strep tag peptide, such as that available from Biometra in Tampa, Fla.; and a phage T7 S 10 peptide.

In another embodiment, a Der HMW-map protein of the present invention also includes at least one additional protein segment that is capable of desensitizing an animal from one or more allergens. Such a multivalent desensitizing protein can be produced by culturing a cell transformed with a nucleic acid molecule comprising two or more nucleic acid domains joined together in such a manner that the resulting nucleic acid molecule is expressed as a multivalent desensitizing compound containing at least two desensitizing compounds capable of desensitizing an animal from allergens.

Examples of multivalent desensitizing compounds include, but are not limited to, a Der HMW-map protein of the present invention attached to one or more compounds that desensitize against allergies caused by one or more allergens, such as a plant allergen, an animal allergen, a parasite allergen or an ectoparasite allergen, including, but not limited to: pant allergens from grass, Meadow Fescue, Curly Dock, plantain, Mexican Firebush, Lamb's Quarters, pigweed, ragweed, sage, elm, cocklebur, Box Elder, walnut, cottonwood, ash, birch, cedar, oak, mulberry, cockroach, *Dermatophagoides, Alternaria, Aspergillus, Cladosporium, Fusarium, Helminthosporium, Mucor, Penicillium, Pullularia, Rhizopus* and/or *Tricophyton*; parasite allergens from helminths; or ectoparasite allergens from arachnids, insects and leeches, including fleas, ticks, flies, mosquitos, sand flies, black flies, horse flies, horn flies, deer flies, tsetse flies, stable flies, myiasis-causing flies and biting gnats, ants, spiders, lice; mites and true bugs.

The present invention also includes mimetopes of a Der HMW-map protein of the present invention. As used herein, a mimetope of a Der HMW-map protein of the present invention refers to any compound that is able to mimic the activity of such a Der HMW-map protein (e.g., ability to bind to induce an immune response against Der HMW-map protein), often because the mimetope has a structure that mimics the Der HMW-map protein. It is to be noted, however, that the mimetope need not have a structure similar to a Der HMW-map protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of Der HMW-map protein of the present invention. Mimetopes can also be obtained by generating random samples of molecules, such as oligonucleotides, peptides or other organic molecules, and screening such samples by affinity chromatography techniques using the corresponding binding partner, (e.g., an anti-Der HMW-map protein antibody). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source. Specific examples of Der HMW-map protein mimetopes include anti-idiotypic antibodies, oligonucleotides produced using Selex™ technology, peptides identified by random screening of peptide libraries and proteins identified by phage display technology. A preferred mimetope is a peptidomimetic compound that is structurally and/or functionally similar to a Der HMW-map protein of the present invention, particularly to an epitope of Der HMW-map protein that induces an immune response.

The present invention also includes muteins of a Der HMW-map protein of the present invention. As used herein, a mutein refers to a particular homolog of a Der HMW-map protein in which desired amino acid residues have been substituted or removed. Preferred muteins of the present invention include Der HMW-map protein homologs in which amino acid residues have been changed to reduce an anaphylactic reaction by an animal when the mutein is administered to the animal in therapeutic doses. More preferred muteins of the present invention include Der HMW-map protein homologs in which one or more cysteine residues of a Der HMW-map protein have been replaced or removed. Methods to produce muteins are known to those of skill in the art and are disclosed herein. Preferably, a mutein is produced using recombinant techniques.

Another embodiment of the present invention is an isolated nucleic acid molecule comprising a Der HMW-map nucleic acid molecule. The identifying characteristics of such nucleic acid molecules are heretofore described. A nucleic acid molecule of the present invention can include an isolated natural Der HMW-map gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated Der HMW-map nucleic acid molecule of the present invention, or a homolog thereof, can be isolated from its natural source or produced using recombinant DNA technology (e.g., polymerase chain reaction (PCR) amplification or cloning) or chemical synthesis. Isolated Der HMW-map nucleic acid molecules, and homologs thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a Der HMW-map protein of the present invention.

A Der HMW-map nucleic acid molecule homolog can be produced using a number of methods known to those skilled in the art, see, for example, Sambrook et al., 1989, *Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof Nucleic acid molecule homologs can be selected by hybridization with a Der HMW-map nucleic acid molecule or by screening the function of a protein encoded by the nucleic acid molecule (e.g., ability to elicit an immune response against at least one epitope of a Der HMW-map protein or to effect Der HMW-map activity).

Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given dust mite since the genome is diploid and/or among a group of two or more dust mites. The present invention also includes variants due to laboratory manipulation, such as, but not limited to, variants produced during polymerase chain reaction amplification.

An isolated nucleic acid molecule of the present invention can include a nucleic acid sequence that encodes at least one Der HMW-map protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a Der HMW-map protein.

A preferred nucleic acid molecule of the present invention, when administered to an animal, is capable of desensitizing that animal from allergic reactions caused by a Der HMW-map allergen. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a desensitizing protein (e.g., a Der HMW-map protein of the present invention), the nucleic acid molecule being delivered to the animal, for example, by direct injection (i.e, as a DNA reagent) or in a vehicle such as a recombinant virus reagent or a recombinant cell reagent.

One embodiment of the present invention is an isolated nucleic acid molecule that hybridizes under stringent hybridization conditions with a Der HMW-map gene. Stringent hybridization conditions refer to standard hybridization conditions described herein. A preferred nucleic acid molecule of the present invention includes an isolated nucleic acid molecule that hybridizes under stringent hybridization conditions with a gene encoding a protein comprising an amino acid sequence including SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, and/or SEQ ID NO:44. A more preferred nucleic acid molecule of the present invention includes an isolated nucleic acid molecule that hybridizes under stringent hybridization conditions with the complement of a nucleic acid sequence that encodes a protein comprising an amino acid sequence including SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, and/or SEQ ID NO:44.

A more preferred nucleic acid molecule of the present invention includes an isolated nucleic acid molecule selected from the group consisting of: a nucleic acid molecule comprising at least about 150 nucleotides, wherein said nucleic acid molecule comprising at least about 150 nucleotides hybridizes, in a solution comprising 1×SSC and 0% formamide, at a temperature of about 50° C., to a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45 and/or a nucleic acid sequence encoding a protein comprising the amino acid sequence SEQ ID NO:33 and a complement thereof.

The present invention also includes fragments of any nucleic acid molecule disclosed herein. According to the present invention, a fragment can include any nucleic acid molecule or nucleic acid sequence, the size of which can range between a length that is smaller than a sequence identified by a SEQ ID NO of the present invention and the minimum size of an oligonucleotide as defined herein. For example, the size of a fragment of the present invention can be any size that is less than about 1752 nucleotides and greater than 11 nucleotides in length.

In one embodiment of the present invention, a preferred Der HMW-map nucleic acid molecule includes an isolated nucleic acid molecule which is at least about 50 nucleotides, or at least about 150 nucleotides, and which hybridizes under conditions which preferably allow about 40% or less base pair mismatch, more preferably under conditions which allow about 35% or less base pair mismatch, more preferably under conditions which allow about 30% or less base pair mismatch, more preferably under conditions which allow about 25% or less base pair mismatch, more preferably under conditions which allow about 20% or less base pair mismatch, more preferably under conditions which allow about 15% or less base pair mismatch, more preferably under conditions which allow about 10% or less base pair mismatch and even more preferably under conditions which allow about 5% or less base pair mismatch with a nucleic acid molecule selected from the group consisting of SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:40, SEQ ID NO:42, SEQ ID NO:43, SEQ ID NO:45, and a nucleic acid sequence encoding a protein comprising the amino acid sequence SEQ ID NO:33 and a complement thereof.

Another embodiment of the present invention includes a nucleic acid molecule comprising at least about 150 base-pairs, wherein the nucleic acid molecule hybridizes, in a solution comprising 1×SSC and 0% formamide, at a temperature of about 50° C., to a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45, and/or a nucleic acid sequence encoding a protein comprising the amino acid sequence SEQ ID NO:33 and a complement thereof. Additional preferred nucleic acid molecules of the present invention include fragments of an isolated nucleic acid molecule comprising at least about 150 base-pairs, wherein said nucleic acid molecule hybridizes, in a solution comprising 1×SSC and 0% formamide, at a temperature of about 50° C., to a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45 and a nucleic acid sequence encoding a protein comprising the amino acid sequence SEQ ID NO:33 and complement thereof.

Additional preferred Der HMW-map nucleic acid molecules of the present invention include an isolated nucleic acid molecule which is at least about 50 nucleotides, or at least about 150 nucleotides, comprising a nucleic acid sequence that is preferably at least about 60% identical, more preferably at least about 65% identical, more preferably at least about 70% identical, more preferably at least about 75% identical, more preferably at least about 80% identical, more preferably at least about 85% identical, more preferably at least about 90% identical and even more preferably at least about 95% identical to a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45, and a nucleic acid sequence encoding a protein comprising the amino acid sequence SEQ ID NO:33 and a complement thereof. Also preferred are fragments of any of such nucleic acid molecules. Percent identity may be determined using the Compare function by maximum matching within the program DNAsis Version 2.1 using default parameters.

One embodiment of the present invention is a nucleic acid molecule comprising all or part of nucleic acid molecules nDerf98$_{1752}$, nDerf98$_{1665}$ and nDerf98$_{1608}$, nDerp98$_{1621}$, nDerp98$_{1527}$, nDerp98$_{1470}$, and/or nDerf60$_{510}$, or allelic variants of these nucleic acid molecules. Another preferred nucleic acid molecule of the present invention includes at least a portion of nucleic acid sequence SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45 and/or a nucleic acid sequence encoding a protein comprising the amino acid sequence SEQ ID NO:33, as well as allelic variants of nucleic acid molecules having these nucleic acid sequences and homologs of nucleic acid molecules having these nucleic acid sequences; preferably such a homolog encodes or is complementary to a nucleic acid molecule that encodes at least one epitope that elicits and an immune response against a protein having an amino acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, SEQ ID NO:41, and/or SEQ ID NO:44. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, a Der HMW-map nucleic acid molecule of the present invention encodes a protein that is at least about 45%, preferably at least about 50%, more preferably at least about 55%, even more preferably at least about 60%, even more preferably at least about 65%, even more preferably at least about 70%, even more preferably at least about 75%, even more preferably at least about 80%, even more preferably at least about 85%, even more preferably at least about 90%, and even more preferably about 95% identical to PDerf98$_{555}$, PDerp98$_{509}$, and/or PDerf60$_{170}$. Even more preferred is a nucleic acid molecule encoding PDerf98$_{555}$, PDerf98$_{536}$, PDerp98$_{509}$, PDerp98$_{490}$, and/or PDerf60$_{170}$, and/or an allelic variant of such nucleic acid molecules.

In another embodiment, a Der HMW-map nucleic acid molecule of the present invention encodes a protein having an amino acid sequence that is at least about 45%, preferably at least about 50%, more preferably at least about 55%, even more preferably at least about 60%, even more preferably at least about 65%, even more preferably at least about 70%, even more preferably at least about 75%, even more preferably at least about 80%, even more preferably at least about 85%, even more preferably at least about 90%, and even more preferably about 95% identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID NO:30, SEQ ID NO:31, SEQ ID NO:32, SEQ ID NO:33, SEQ ID NO:35, SEQ ID NO:38, SEQ ID NO:41, SEQ ID NO:41, and/or SEQ ID NO:44. The present invention also includes a Der HMW-map nucleic acid molecule encoding a protein having at least a portion of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:29, SEQ ID N0:30, SEQ ID NO:31, SEQ ID NO:32, SEQ ID NO:33, SEQ ID NO:35, SEQ ID NO:38, SEQ ID NO:41, SEQ ID NO:41, and/or SEQ ID NO:44, as well as allelic variants of a Der HMW-map nucleic acid molecule encoding a protein having these sequences, including nucleic acid molecules that have been modified to accommodate codon usage properties of the cells in which such nucleic acid molecules are to be expressed.

In another embodiment, a preferred Der HMW-map nucleic acid molecule encodes a Der HMW-map protein comprising at least about at least about 35 amino acids in length, preferably at least about 50 amino acids in length, more preferably at least about 100 amino acids in length, more preferably at least about 200 amino acids in length, even more preferably at least about 250 amino acids in length.

Knowing the nucleic acid sequences of certain Der HMW-map nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other Der HMW-map nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. A preferred library to screen or from which to amplify nucleic acid molecules includes a *Dermatophagoides farinae* and/or *Dermatophagoides pteronyssius* library, such as the libraries disclosed herein in the Examples. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising Der HMW-map nucleic acid molecules or other Der HMW-map nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably about 200 nucleotides, more preferably about 150 nucleotides and even more preferably about 100 nucleotides. The present invention includes oligonucleotides that can be used as, for example, probes to identify nucleic acid molecules.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of Der HMW-map nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, Heliothis zea insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with canines or felines.

Suitable and preferred nucleic acid molecules to include in recombinant vectors of the present invention are as disclosed herein. Preferred nucleic acid molecules to include in recombinant vectors, and particularly in recombinant molecules, include nDerf98$_{1752}$, nDerf98$_{1665}$ nDerf98$_{1608}$, nDerp98$_{1621}$, nDerp98$_{1527}$, nDerp98$_{1470}$, and nDerf60$_{510}$.

Recombinant molecules of the present invention may also (a) contain secretory signals (i.e., signal segment nucleic acid sequences) to enable an expressed Der HMW-map protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include Der HMW-map nucleic acid molecules disclosed herein. Particularly preferred nucleic acid molecules with which to transform a cell include nDerf98$_{1752}$, nDerf98$_{1665}$ nDerf98$_{1608}$, nDerp98$_{1621}$, nDerp98$_{1527}$, nDerp98$_{1470}$, and nDerf60$_{510}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing Der HMW-map proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacterial, yeast, parasite, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are Escherichia coli, including E. coli K-12 derivatives; Salmonella typhi; Salmonella typhimurium, including attenuated strains such as UK-1 $_{x}$3987 and SR-11 $_{x}$4072; Spodoptera frugiperda; Trichoplusia ni; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein.

A recombinant cell of the present invention includes any cell transformed with at least one of any Der HMW-map nucleic acid molecule of the present invention. Suitable and preferred Der HMW-map nucleic acid molecules as well as suitable and preferred recombinant molecules with which to transform cells are disclosed herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated Der HMW-map proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a Der HMW-map protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in E. coli; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of desensitizing a treated animal.

The present invention also includes isolated (i.e., removed from their natural milieu) antibodies that selectively bind to a Der HMW-map protein of the present invention or a mimetope thereof (i.e., anti-Der HMW-map protein antibodies). As used herein, the term "selectively binds to" a Der HMW-map protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-Der HMW-map protein antibody preferably selectively binds to a portion of a Der HMW-map protein that induces an immune response in an animal.

Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce Der HMW-map proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as tools to detect mite allergen, in particular Der HMW-map protein; (b) as tools to screen expression libraries; and/or (c) to recover desired proteins of the present invention from a mixture of proteins and other contaminants. Antibodies of the present invention can also be used, for example, to inhibit binding of Der HMW-map protein to IgE that binds specifically to Der HMW-map protein, to prevent immunocomplex formation, thereby reducing hypersensitivity responses to mite allergens.

A Der HMW-map protein of the present invention can be included in a chimeric molecule comprising at least a portion of a Der HMW-map protein that induces an immune response in an animal and a second molecule that enables the chimeric molecule to be bound to a substrate in such a manner that the Der HMW-map protein portion can bind to IgE in essentially the same manner as a Der HMW-map protein that is not bound to a substrate. An example of a suitable second molecule includes a portion of an immunoglobulin molecule or another ligand that has a suitable binding partner that can be immobilized on a substrate, e.g., biotin and avidin, or a metal-binding protein and a metal (e.g., His), or a sugar-binding protein and a sugar (e.g., maltose).

A Der HMW-map protein of the present invention can be contained in a formulation, herein referred to as a Der HMW-map protein formulation. For example, a Der HMW-map protein can be combined with a buffer in which the Der HMW-map protein is solubilized, and/or with a carrier. Suitable buffers and carriers are known to those skilled in the art. Examples of suitable buffers include any buffer in which a Der HMW-map protein can function to selectively bind to an antibody that specifically binds to Der HMW-map protein, such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be mixed with Der HMW-map protein or conjugated (i.e., attached) to Der HMW-map protein in such a manner as to not substantially interfere with the ability of the Der HMW-map protein to selectively bind to an antibody that specifically binds to Der HMW-map protein.

A Der HMW-map protein of the present invention can be produced by a cell comprising the Der HMW-map protein. A preferred Der HMW-map protein-bearing cell includes a recombinant cell comprising a nucleic acid molecule encoding a Der HMW-map protein of the present invention.

In addition, a Der HMW-map protein formulation of the present invention can include not only a Der HMW-map protein but also one or more additional antigens or antibodies useful in desensitizing an animal against allergy, or preventing or treating mite allergen pathogenesis. As used herein, an antigen refers to any molecule capable of being selectively bound by an antibody. As used herein, an allergen refers to any antigen that is capable of stimulating production of antibodies involved in an allergic response in an animal. As used herein, selective binding of a first molecule to a second molecule refers to the ability of the first molecule to preferentially bind (e.g., having higher affinity higher avidity) to the second molecule when compared to the ability of a first molecule to bind to a third molecule. The first molecule need not necessarily be the natural ligand of the second molecule. Allergens of the present invention are preferably derived from mites, and mite-related allergens including, but not limited to, other insect allergens and plant allergens.

In accordance with the present invention, virtually any substance can act as an antigen and elicit an antibody response, i.e., can function as an epitope. For example, antibodies can be raised in response to carbohydrate epitopes, including saccharides and/or polysaccharides that are attached to a protein, a so-called glycosylated protein. However, a saccharide and/or polysaccharide may act as an antigen alone, without a protein being present. The terminal sugar of a carbohydrate moiety, as well as internal sugars can serve as an epitope. Polysaccharide may be present as a branched chain, in which case epitopes may comprise sugars that are not contiguous in sequence, but are adjacent spatially. Unusual, insect-specific sugars, not normally seen in mammalian proteins, may be present on glycoprotein derived from insect nucleic acid molecules, and these unusual sugars can comprise an epitope recognized by a mammalian immune system.

One embodiment of the present invention is a reagent comprising a non-proteinaceous epitope that is capable of binding to IgE of an animal that is allergic to mites, of desensitizing an animal against mite allergen, of stimulating a B lymphocyte response, and/or of stimulating a T lymphocyte response. Such an epitope, referred to herein as a Der NP epitope, can exist as part of a Der HMW-map protein of the present invention or can be isolated therefrom. Such an epitope exists, for example, on a protein contained in the *D. farinae* HMW-map composition produced in accordance with Example 1. A Der NP epitope of the present invention can be isolated from its natural source or produced synthetically. Such an epitope can be, but need not be, joined to a carrier or other molecule. A Der NP epitope has at least one of the following identifying characteristics: (a) the epitope is resistant to β-elimination of peptides; (b) the epitope is resistant to Proteinase-K digestion; and (c) the epitope is reactive to a test designed to detect glycosylated proteins. A preferred Der NP epitope has all such identifying characteristics. A Der NP epitope can selectively bind to IgE of dogs or cats that are allergic to mites. While not being bound by theory, it is believed that a Der NP epitope comprises a carbohydrate moiety that apparently does not include an N-linked glycan. Identification of the structural characteristics of such an epitope can be determined by one skilled in the art. In one embodiment, there is provided an isolated antibody that selectively binds to a Der NP epitope. The present invention also includes a derivative of a Der NP epitope, i.e., a compound that mimics the activity of such an epitope (e.g. is a Der NP epitope mimetope) and is capable of binding to antibody raised against a native (i.e. seen in nature) Der NP epitope.

A reagent comprising a Der NP epitope of the present invention can be used in a variety of ways in accordance with the present invention. Such a reagent can be a desensitizing compound or a detection reagent to test for mite allergy susceptibility or sensitivity. In one embodiment, a therapeutic composition of the present invention includes a reagent comprising a Der NP epitope. In another embodiment, an assay kit of the present invention includes a reagent comprising a Der NP epitope. One embodiment of the present invention is a method to identify an animal susceptible to or having an allergic response to a mite. Such a method includes the steps of contacting a reagent comprising a Der NP epitope with antibodies of an animal and determining immunocomplex formation between the reagent and the antibodies, wherein formation of the immunocomplex indicates that the animal is susceptible to or has said allergic response. Another embodiment of the present invention is a method to desensitize a host animal to an allergic response to a mite. Such a method includes the step of administering to the animal a therapeutic composition that includes a reagent comprising a Der NP epitope as a desensitizing compound.

Another embodiment of the present invention is a Der HMW-map protein lacking Der NP epitopes. Without being bound by theory, it is believed that such a protein would be a better desensitizing compound since such a protein is expected to have a reduced ability to bind to IgE. Such a protein can be produced by, for example, removing Der NP epitopes from a native Der HMW-map protein or by producing the protein recombinantly, for example in E. coli.

One embodiment of the present invention is an in vivo test that is capable of detecting whether an animal is hypersensitive to Der HMW-map protein. An in vivo hypersensitivity test of the present invention is particularly useful for identifying animals susceptible to or having allergy to mite allergens. A suitable in vivo hypersensitivity test of the present invention can be, but is not limited to, a skin test comprising administering (e.g., intradermally injecting or superficial scratching) an effective amount of a formulation containing Der HMW-map protein, or a mimetope thereof. Methods to conduct skin tests of the present invention are known to those of skill in the art and are briefly disclosed herein.

Suitable formulations to use in an in vivo skin test include Der HMW-map protein, homologs of Der HMW-map protein and/or mimetopes of Der HMW-map protein.

It is understood by one of skill in the art that a suitable amount of Der HMW-map protein formulation for use in a skin test of the present invention can vary widely depending on the allergenicity of the formulation used in the test and on the site at which the product is delivered. Suitable amounts of Der HMW-map protein formulation for use in a skin test of the present invention include an amount capable of forming reaction, such as a detectable wheal or induration (hardness) resulting from an allergic reaction to the formulation. Preferred amounts of Der HMW-map protein for use in a skin test of the present invention range from about $1\times10^{-8}$ micrograms (μg) to about 100 μg, more preferably from about $1\times^{-7}$ μg to about 10 μg, and even more preferably from about $1\times10^{-6}$ μg to about 1 μg of Der HMW-map protein. It is to be appreciated by those of skill in the art that such amounts will vary depending upon the allergenicity of the protein being administered.

According to the present invention, Der HMW-map protein of the present invention can be combined with an immunopotentiator (e.g., carriers or adjuvants of the present invention as defined in detail below). A novel aspect, however, of the present invention is that Der HMW-map protein of the present invention can induce a hypersensitive response in the absence of an immunopotentiator, particularly in canines.

A skin test of the present invention further comprises administering a control solution to an animal. A control solution can include a negative control solution and/or a positive control solution. A positive control solution of the present invention contains an effective amount of at least one compound known to induce a hypersensitive response when administered to an animal. A preferred compound for use as positive control solution includes, but is not limited to, histamine. A negative control solution of the present invention can comprise a solution that is known not to induce a hypersensitive response when administered to an animal. As such, a negative control solution can comprise a solution having compounds essentially incapable of inducing a hypersensitive response or simply a buffer used to prepare the formulation, such as saline. An example of a preferred negative control solution is phenolated phosphate buffered saline (available from Greer Laboratories, Inc., Lenoir, N.C.).

Hypersensitivity of an animal to one or more formulations of the present invention can be evaluated by measuring reactions (e.g., wheal size, induration or hardness; using techniques known to those skilled in the art) resulting from administration of one or more experimental sample(s) and control sample(s) into an animal and comparing the reactions to the experimental sample(s) with reactions resulting from administration of one or more control solution. Preferred devices for intradermal injections include individual syringes. Preferred devices for scratching include devices that permit the administration of a number of samples at one time. The hypersensitivity of an animal can be evaluated by determining if the reaction resulting from administration of a formulation of the present invention is larger than the reaction resulting from administration of a negative control, and/or by determining if the reaction resulting from administration of the formulation is at least about the same size as the reaction resulting from administration of a positive control solution. As such, if an experimental sample produces a reaction greater than or equal to the size of a wheal produced by administration of a positive control sample to an animal, then that animal is hypersensitive to the experimental sample. Conversely, if an experimental sample produces a reaction similar to the reaction produced by administration of a negative control sample to an animal, then that animal is not hypersensitive to the experimental sample.

Preferred wheal sizes for evaluation of the hypersensitivity of an animal range from about 16 mm to about 8 mm, more preferably from about 15 mm to about 9 mm, and even more preferably from about 14 mm to about 10 mm in diameter.

Preferably, the ability or inability of an animal to exhibit an immediate hypersensitive response to a formulation of the present invention is determined by measuring wheal sizes from about 2 minutes to about 30 minutes after administration of a sample, more preferably from about 10 minutes to about 25 minutes after administration of a sample, and even more preferably about 15 minutes after administration of a sample.

Preferably, the ability or inability of an animal to exhibit a delayed hypersensitive response to a formulation of the present invention is determined by measuring induration and/or erythema from about 18 hours to about 30 hours after administration of a sample, more preferably from about 20 hours to about 28 hours after administration of a sample, and even more preferably at about 24 hours after administration of a sample. A delayed hypersensitivity response can also be measured using other techniques such as by determining, using techniques known to those of skill in the art, the extent of cell infiltrate at the site of administration during the time periods defined directly above.

In a preferred embodiment, a skin test of the present invention comprises intradermally injecting into an animal at a given site an effective amount of a formulation that includes Der HMW-map protein, and intradermally injecting an effective amount of a control solution into the same animal at a different site. It is within the scope of one of skill in the art to use devices capable of delivering multiple samples simultaneously at a number of sites, preferably enabling concurrent evaluation of numerous formulations. A preferred Der HMW-map protein for use with a skin test includes full-length protein. A preferred positive control sample can be a sample comprising histamine. A preferred negative control sample can be a sample comprising diluent.

Animals suitable and preferred to test for hypersensitivity to Der HMW-map protein using a skin test of the present invention are disclosed herein. Particularly preferred animals to test with a skin test of the present invention include humans, canines, felines and equines, with human, canines and felines being even more preferred. As used herein, canine refers to any member of the dog family, including domestic dogs, wild dogs and zoo dogs. Examples of dogs include, but are not limited to, domestic dogs, wild dogs, foxes, wolves, jackals and coyotes. As used herein, feline refers to any member of the cat family, including domestic cats, wild cats and zoo cats. Examples of cats include, but are not limited to, domestic cats, lions, tigers, leopards, panthers, cougars, bobcats, lynx, jaguars, cheetahs and servals. As used herein, equine refers to any member of the horse family, including horses, donkeys, mules and zebras.

One embodiment of the present invention is a method to detect antibodies in vitro that bind to Der HMW-map protein (referred to herein as anti-Der HMW-map antibody) which includes the steps of: (a) contacting an isolated Der HMW-map protein with a putative anti-Der HMW-map antibody-containing composition under conditions suitable for formation of a Der HMW-map protein:antibody complex; and (b) detecting the presence of the antibody by detecting the Der HMW-map protein:antibody complex. Presence of such a Der HMW-map protein:antibody complex indicates that the animal is producing antibody to a mite allergen. Preferred anti-Der HMW-map antibody to detect include antibodies having an IgE or IgG isotype. Preferred anti-Der HMW-map antibody to detect include feline antibody, canine antibody, equine antibody and human antibody, with feline, canine and human antibody being particularly preferred.

As used herein, the term "contacting" refers to combining or mixing, in this case a putative antibody-containing composition with a Der HMW-map protein. Formation of a complex between a Der HMW-map protein and an antibody refers to the ability of the Der HMW-map protein to selectively bind to the antibody in order to form a stable complex that can be measured (i.e., detected). As used herein, the term selectively binds to an antibody refers to the ability of a Der HMW-map protein of the present invention to preferentially bind to an antibody, without being able to substantially bind to other antibodies that do not specifically bind to Der HMW-map protein. Binding between a Der HMW-map protein and an antibody is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., ibid.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, between Der HMW-map protein and an antibody in the composition can be measured (i.e., detected, determined) using a variety of methods standard in the art (see, for example, Sambrook et al. ibid.), examples of which are disclosed herein.

In one embodiment, a putative antibody-containing composition of the present method includes a biological sample from an animal. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, milk and feces. Such a composition of the present method can, but need not be, pretreated to remove at least some of the non-IgE or non-IgG isotypes of immunoglobulin and/or other proteins, such as albumin, present in the fluid. Such removal can include, but is not limited to, contacting the bodily fluid with a material, such as the lectin jacalin or an antibody that specifically binds to the constant region of an IgA immunoglobulin (i.e., anti-IgA isotype antibody), to remove IgA antibodies and/or affinity purifying IgE or IgG antibodies from other components of the body fluid by exposing the fluid to, for example, Concanavalin A or protein G, respectively. In another embodiment, a composition includes collected bodily fluid that is pretreated to concentrate immunoglobulin contained in the fluid. For example, immunoglobulin contained in a bodily fluid can be precipitated from other proteins using ammonium sulfate. A preferred composition of the present method is serum.

In another embodiment, an antibody-containing composition of the present method includes a cell that produces IgE or IgG. Such a cell can have IgE or IgG bound to the surface of the cell and/or can secrete IgE or IgG. An example of such a cell includes myeloma cells. IgE or IgG can be bound to the surface of a cell either directly to the membrane of the cell or bound to a molecule (e.g., an antigen) bound to the surface of the cell.

A complex can be detected in a variety of ways including, but not limited to use of one or more of the following assays: an enzyme-linked immunoassay, a radioimmunoassay, a fluorescence immunoassay, a chemiluminescent assay, a lateral flow assay, an agglutination assay, a particulate-based assay (e.g., using particulates such as, but not limited to, magnetic particles or plastic polymers, such as latex or polystyrene beads), an immunoprecipitation assay, a BioCore™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker.

In other assays, conjugation (i.e., attachment) of a detectable marker to the Der HMW-map protein, to antibody bound to the Der HMW-map protein, or to a reagent that selectively binds to the Der HMW-map protein or to the antibody bound to the Der HMW-map protein (described in more detail below) aids in detecting complex formation. Examples of detectable markers include, but are not limited to, a radioactive label, an enzyme, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin available from Pierce, Rockford, Ill.).

In one embodiment, a complex is detected by contacting a putative antibody-containing composition with a Der HMW-map protein that is conjugated to a detectable marker. A suitable detectable marker to conjugate to a Der HMW-map protein includes, but is not limited to, a radioactive label, a fluorescent label, an enzyme label, a chemiluminescent label, a chromophoric label or a ligand. A detectable marker is conjugated to a Der HMW-map protein in such a manner as not to block the ability of the Der HMW-map protein to bind to the antibody being detected.

In another embodiment, a Der HMW-map protein: antibody complex is detected by contacting a putative antibody-containing composition with a Der HMW-map protein and then contacting the complex with an indicator molecule. Suitable indicator molecules of the present invention include molecules that can bind to either the Der HMW-map protein or to the antibody bound to the Der HMW-map protein. As such, an indicator molecule can comprise, for example, an antigen and an antibody, depending upon which portion of the Der HMW-map protein:antibody complex is being detected. Preferred indicator molecules that are antibodies include, for example, anti-IgE antibodies, anti-IgG antibodies and antibodies that are known bind to Der HMW-map protein but bind to a different epitope on Der HMW-map protein than antibodies identified in the putative antibody-containing composition. Preferred lectins include those lectins that bind to high-mannose groups. An indicator molecule itself can be attached to a detectable marker of the present invention. For example, an antibody can be conjugated to biotin, horseradish peroxidase, alkaline phosphatase or fluorescein.

In one preferred embodiment, a Der HMW-map protein: antibody complex is detected by contacting the complex with an indicator molecule that selectively binds to an IgE antibody (referred to herein as an anti-IgE reagent) or an IgG antibody (referred to herein as an anti-IgG reagent. Examples of such an anti-IgE or an anti-IgG antibody include, but are not limited to, a secondary antibody that is an anti-isotype antibody (e.g., an antibody that selectively binds to the constant region of an IgE or an IgG), an antibody-binding bacterial surface protein (e.g., Protein A or Protein G), an antibody-binding cell (e.g., a B cell, a T cell, a natural killer cell, a polymorphonuclear leukocyte cell, a monocyte cell or a macrophage cell), an antibody-binding eukaryotic cell surface protein (e.g., a Fc receptor), and an antibody-binding complement protein. Preferred indicator molecules include, but are not limited to, an anti-feline IgE antibody, an anti-feline IgG antibody, an anti-canine IgE antibody, an anti-canine IgG antibody, an anti-human IgE antibody, and an anti-human IgG antibody. As used herein, an anti-IgE or anti-IgG antibody includes not only a complete antibody but also any subunit or portion thereof that is capable of selectively binding to an IgE or IgG heavy chain constant region. For example, an anti-IgE reagent or anti-IgG reagent can include an Fab fragment or a F(ab')$_2$ fragment, both of which are described in detail in Janeway et al., in *Immunobiology, the Immune System in Health and Disease*, Garland Publishing, Inc., NY, 1996 (which is incorporated herein by this reference in its entirety).

In another preferred embodiment, a Der HMW-map protein:antibody complex is detected by contacting the complex with an indicator molecule that selectively binds to Der HMW-map protein at a different epitope than the epitope at which an antibody in a putative antibody-containing composition binds to Der HMW-map protein.

In one embodiment a complex can be formed and detected in solution. In another embodiment, a complex can be formed in which one or more members of the complex are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker.

A preferred method to detect antibody that binds to Der HMW-map protein is an immunoabsorbent assay. An immunoabsorbent assay of the present invention comprises a capture molecule and an indicator molecule. A capture molecule of the present invention binds to an IgE or an IgG in such a manner that the IgE or IgG is immobilized to a substrate. As such, a capture molecule is preferably immobilized to a substrate of the present invention prior to exposure of the capture molecule to a putative IgE-containing composition or a putative IgG-containing composition. An indicator molecule of the present invention detects the presence of an IgE or an IgG bound to a capture molecule. As such, an indicator molecule preferably is not immobilized to the same substrate as a capture molecule prior to exposure of the capture molecule to a putative IgE-containing composition or a putative IgG-containing composition.

A preferred immunoabsorbent assay method includes a step of either: (a) immobilizing a Der HMW-map protein on a substrate prior to contacting a Der HMW-map protein with a putative IgE-containing composition or a putative IgG-containing composition to form a Der HMW-map protein-immobilized substrate; and (b) binding a putative IgE-containing composition or a putative IgG-containing composition on a substrate prior to contacting Der HMW-map protein with a putative IgE-containing composition or a putative IgG-containing composition, to form a putative IgE-containing composition-bound substrate or a putative IgG-containing composition-bound substrate, respectively. Preferably, the substrate includes a non-coated substrate, a Der HMW-map protein-immobilized substrate, an anti-IgE antibody-immobilized substrate or anti-IgG antibody-immobilized substrate.

Both a capture molecule and an indicator molecule of the present invention are capable of binding to an IgE, an IgG or Der HMW-map protein. Preferably, a capture molecule binds to a different region of an IgE, an IgG or Der HMW-map protein than an indicator molecule, thereby allowing a capture molecule to be bound to an IgE, an IgG or Der HMW-map protein at the same time as an indicator molecule. The use of a reagent as a capture molecule or an indicator molecule depends upon whether the molecule is immobilized to a substrate when the molecule is exposed to an IgE, an IgG or Der HMW-map protein. For example, a Der HMW-map protein of the present invention is used as a capture molecule when the Der HMW-map protein is bound on a substrate. Alternatively, a Der HMW-map protein is used as an indicator molecule when the Der HMW-map protein is not bound on a substrate. Suitable molecules for use as capture molecules or indicator molecules include, but are not limited to, a Der HMW-map protein of the present invention, an anti-IgE antibody reagent or an anti-IgG antibody reagent of the present invention.

An immunoabsorbent assay of the present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be selected by those of skill in the art. Preferred secondary molecules of the present invention include an antigen, an anti-IgE idiotypic antibody (i.e., an antibody that binds to an epitope unique to the anti-IgE antibody), an anti-IgE isotypic antibody, an anti-IgG idiotypic antibody (i.e., an antibody that binds to an epitope unique to the anti-IgG antibody), and an anti-IgG isotypic antibody. Preferred tertiary molecules can be selected by a skilled artisan based upon the characteristics of the secondary molecule. The same strategy is applied for subsequent layers.

In one embodiment, Der HMW-map protein is used as a capture molecule by being immobilized on a substrate, such as a microtiter dish well or a dipstick. A biological sample collected from an animal is applied to the substrate and incubated under conditions suitable (i.e., sufficient) to allow for Der HMW-map protein:antibody complex formation bound to the substrate (i.e., IgE or IgG in a sample binds to Der HMW-map protein immobilized on a substrate). Excess non-bound material (i.e., material from the biological sample that has not bound to the Der HMW-map protein), if any, is removed from the substrate under conditions that retain antigen:antibody complex binding to the substrate. Preferred conditions are generally disclosed in Sambrook et al., ibid. An indicator molecule that can selectively bind to an IgE or an IgG bound to the antigen is added to the substrate and incubated to allow formation of a complex between the indicator molecule and the Der HMW-map protein:antibody complex. Excess indicator molecule is removed, a developing agent is added if required, and the substrate is submitted to a detection device for analysis. A preferred indicator molecule for this embodiment is an anti-IgG antibody to detect IgG antibody bound to Der HMW-map protein or an anti-IgE antibody to detect IgE antibody bound to Der HMW-map protein. Preferably the anti-IgG or anti-IgE antibody are conjugated to biotin, to a fluorescent label or to an enzyme label.

In one embodiment, an anti-IgE or anti-IgG antibody (e.g., isotype or idiotype specific antibody) is used as a capture molecule by being immobilized on a substrate, such as a microtiter dish well or a dipstick. A biological sample collected from an animal is applied to the substrate and incubated under conditions suitable to allow for anti-IgE antibody:IgE complex or anti-IgG antibody:IgG complex formation, respectively, bound to the substrate. Excess non-bound material, if any, is removed from the substrate under conditions that retain anti-IgE antibody:IgE complex or anti-IgG antibody:IgG complex binding to the substrate. Der HMW-map protein is added to the substrate and incubated to allow formation of a complex between the Der HMW-map protein and the anti-IgE antibody:IgE complex or anti-IgG antibody:IgG complex. Preferably, the Der HMW-map protein is conjugated to a detectable marker (preferably to biotin, an enzyme label or a fluorescent label). Excess Der HMW-map protein is removed, a developing agent is added if required, and the substrate is submitted to a detection device for analysis.

In one embodiment, an immunoabsorbent assay of the present invention does not utilize a capture molecule. In this embodiment, a biological sample collected from an animal is applied to a substrate, such as a microtiter dish well or a dipstick, and incubated under conditions suitable to allow for IgE or IgG binding to the substrate. Any IgE or IgG present in the bodily fluid is immobilized on the substrate. Excess non-bound material, if any, is removed from the substrate under conditions that retain IgE or IgG binding to the substrate. Der HMW-map protein is added to the substrate and incubated to allow formation of a complex between the Der HMW-map protein and the IgE or IgG. Preferably, the Der HMW-map protein is conjugated to a detectable marker (preferably to biotin, an enzyme label or a fluorescent label). Excess Der HMW-map protein is removed, a developing agent is added if required, and the substrate is submitted to a detection device for analysis.

Another preferred method to detect IgE or IgG is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; (b) a labeling reagent comprising a bead conjugated to Der HMW-map protein, the labeling reagent being impregnated within the support structure in a labeling zone; and (c) a capture reagent comprising an IgE-binding or an IgG-binding composition. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose (NC), PVDF, carboxymethylcellulose (CM). The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the biological sample is applied to the sample receiving zone which includes a portion of the support structure. The labeling zone receives the sample from the sample receiving zone which is directed downstream by the flow path. The labeling zone comprises the labeling reagent that binds to IgE or IgG, or both. A preferred labeling reagent is Der HMW-map protein conjugated, either directly or through a linker, to a plastic bead substrate, such as to a latex bead. The substrate also includes a detectable marker, preferably a colorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, in this case an anti-IgE or anti-IgG antibody, or both, as disclosed above, that immobilizes the IgE and/or IgG complexed to the Der HMW-map protein in the capture zone. The capture reagent is preferably fixed to the support structure by drying or lyophilizing. The labeling reagent accumulates in the capture zone and the accumulation is assessed visually or by an optical detection device.

In another embodiment, a lateral flow apparatus used to detect IgE or IgG includes: (a) a support structure defining a flow path; (b) a labeling reagent comprising an anti-IgE or an anti-IgG antibody, or both, as described above, the labeling reagent impregnated within the support structure in a labeling zone; and (c) a capture reagent comprising Der HMW-map protein, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path.

An animal hypersensitive to Der HMW-map protein is identified by comparing the level of immunocomplex formation using samples of body fluid with the level of immunocomplex formation using control samples. An immunocomplex refers to a complex comprising an antibody and Der HMW-map protein (i.e., Der HMW-map protein:antibody complex). As such, immunocomplexes form using positive control samples and do not form using negative control samples. As such, if a body fluid sample results in immunocomplex formation greater than or equal to immunocomplex formation using a positive control sample, then the animal from which the fluid was taken is hypersensitive to the Der HMW-map protein bound to the substrate. Conversely, if a body fluid sample results in immunocomplex formation similar to immunocomplex formation using a negative control sample, then the animal from which the fluid was taken is not hypersensitive to the Der HMW-map protein bound to the substrate.

It is within the scope of the present invention that two or more different skin tests and/or in vitro tests can be used in combination for diagnostic purposes. For example, the immediate hypersensitivity of an animal to Der HMW-map protein can be tested using an in vitro immunoabsorbent test capable of detecting IgE antibodies specific for Der HMW-map protein in the animal's bodily fluid. While most animals that display delayed hypersensitivity to Der HMW-map protein also display immediate hypersensitivity to the allergen, a small number of animals that display delayed hypersensitivity to an allergen do not display immediate hypersensitivity to the allergen. In such cases, following negative results from the IgE-specific in vitro test, the delayed hypersensitivity of the animal to Der HMW-map protein can be tested using an skin test of the present invention.

The present invention also includes kits to detect antibodies that bind specifically to Der HMW-map protein based on each of the disclosed detection methods. One embodiment is a kit to detect Der HMW-map protein-specific antibodies comprising Der HMW-map protein and a means for detecting an IgE and/or an IgG. Suitable means of detection include compounds disclosed herein that bind to either the Der HMW-map protein or to an IgE and/or an IgG. A preferred kit of the present invention further comprises a detection means including an antibody capable of selectively binding to an IgE or IgG disclosed herein and/or a compound capable of binding to a detectable marker conjugated to a Der HMW-map protein (e.g., avidin, streptavidin and ImmunoPure® NeutrAvidin when the detectable marker is biotin).

Another preferred kit of the present invention is an allergen kit comprising Der HMW-map protein and an allergen commonly detected in the same environment as mite allergen. Suitable and preferred mite-related allergens for use with the present kit include those mite-related allergens disclosed herein.

A preferred kit of the present invention includes those in which Der HMW-map protein is immobilized on a substrate. If a kit comprises Der HMW-map protein and another allergen, the kit can comprise one or more compositions, each composition comprising one allergen. As such, each allergen can be tested separately. A kit can also contain two or more diagnostic reagents for IgE or IgG, or other compounds as disclosed herein. Particularly preferred are kits used in a lateral flow assay format. It is within the scope of the present invention that a lateral flow assay kit can include one or more lateral flow assay apparatuses. Multiple lateral flow apparatuses can be attached to each other at one end of each apparatus, thereby creating a fan-like structure.

Another aspect of the present invention includes treating animals susceptible to or having mite allergy, with a Der HMW-map protein formulation of the present invention. According to the present invention, the term treatment can refer to the regulation of a hypersensitive response by an animal to mite allergens. Regulation can include, for example, immunomodulation of cells involved in the animal's hypersensitive response. Immunomodulation can include modulating the activity of molecules typically involved in an immune response (e.g., antibodies, antigens, major histocompatibility molecules (MHC) and molecules co-reactive with MHC molecules). In particular, immunomodulation refers to modulation of antigen:antibody interactions resulting in inflammatory responses, immunosuppression, and immunotolerization of cells involved in a hypersensitive response. Immunosuppression refers to inhibiting an immune response by, for example, killing particular cells involved in the immune response. Immunotolerization refers to inhibiting an immune response by anergizing (i.e., diminishing reactivity of a T cell to an antigen) particular cells involved in the immune response.

One embodiment of the present invention is a therapeutic composition that includes desensitizing compounds capable of inhibiting an immune response to Der HMW-map protein of the present invention. Such desensitizing compounds include blocking compounds, toleragens and/or suppressor compounds. Blocking compounds comprise compounds capable of modulating antigen:antibody interactions that can result in inflammatory responses, toleragens are compounds capable of immunotolerizing an animal, and suppressor compounds are capable of immunosuppressing an animal. A desensitizing compound of the present invention can be soluble or membrane-bound. Membrane-bound desensitizing compounds can be associated with biomembranes, including cells, liposomes, planar membranes or micelles. A soluble desensitizing compound of the present invention is useful for: (1) inhibiting a Type I hypersensitivity reaction by blocking IgE:antigen mediated de-granulation of mast cells; (2) inhibiting a Type III hypersensitivity reaction by blocking IgG:antigen complex formation leading to complement destruction of cells; and (3) inhibiting a Type IV hypersensitivity reaction by blocking T helper cell stimulation of cytokine secretion by macrophages. A membrane-bound desensitizing compound of the present invention is useful for: (1) inhibiting a Type II hypersensitivity reaction by blocking IgG:antigen complex formation on the surface of cells leading to complement destruction of cells; (2) inhibiting a Type II hypersensitivity reaction by blocking IgG regulated signal transduction in immune cells; and (3) inhibiting a Type IV hypersensitivity reaction by blocking T cytotoxic cell killing of antigen-bearing cells. Examples of desensitizing compounds include, but are not limited to, muteins, mimetopes and antibodies of the present invention, as well as other inhibitors of the present invention that inhibit binding between a protein of the present invention and IgE.

A desensitizing compound of the present invention can also be covalently linked to a ligand molecule capable of targeting the desensitizing compound to a specific cell involved in a hypersensitive response to Der HMW-map protein. Appropriate ligands with which to link a desensitizing compound include, for example, at least a portion of an immunoglobulin molecule, cytokines, lectins, heterologous allergens, CD8 molecules or major histocompatibility molecules (e.g., MHC class I or MHC class II molecules). Preferred portions of immunoglobulin molecules to link to a desensitizing compound include variable regions capable of binding to immune cell specific surface molecules and constant regions capable of binding to Fc receptors on immune cells, in particular IgE constant regions. Preferred CD8 molecules include at least the extracellular functional domains of the α chain of CD8. An immune cell refers to a cell involved in an immune response, in particular, cells having MHC class I or MHC class II molecules. Preferred immune cells include antigen presenting cells, T cells and B cells.

In one embodiment, a therapeutic composition of the present invention includes Der HMW-map protein of the present invention, a mimetope or mutein thereof, or a Der HMW-map nucleic acid molecule of the present invention. Suitable therapeutic compositions of the present invention for treating mite allergy include Der HMW-map protein, a mimetope or mutein thereof, or a Der HMW-map nucleic acid molecule of the present invention. Preferred therapeutic compositions include: an isolated mite allergenic protein encoded a nucleic acid molecule that hybridizes under stringent hybridization conditions with the complement of a nucleic acid molecule that encodes an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:30, SEQ ID NO:31, SEQ ID NO:32, SEQ ID NO:33, SEQ ID NO:33, SEQ ID NO:35, SEQ ID NO:38, SEQ ID NO:41, and SEQ ID NO:44; a mimetope of the mite allergenic protein; a mutein of the mite allergenic protein; and an isolated nucleic acid molecule selected from the group consisting of: a nucleic acid molecule comprising at least about 150 nucleotides, wherein said nucleic acid molecule comprising at least about 150 nucleotides hybridizes, in a solution comprising 1×SSC and 0% formamide, at a temperature of about 50° C., to a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45, and a nucleic acid sequence encoding a protein comprising the amino acid sequence SEQ ID NO:33 and a complement thereof; and a nucleic acid molecule comprising a fragment of any of said nucleic acid molecules comprising at least about 150 nucleotides. A preferred Der HMW-map mutein comprises at least a portion of Der HMW-map protein, in which a suitable number of cysteine residues have been removed or replaced with a non-cysteine residue such that the altered Der HMW-map protein is not toxic to an animal (e.g., does not cause anaphylaxis).

In another embodiment, a therapeutic composition of the present invention includes a nucleic acid molecule encoding a Der HMW-map protein that can be administered to an animal in a fashion to enable expression of that nucleic acid molecule into a Der HMW-map protein in the animal. Nucleic acid molecules can be delivered to an animal in a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, *Science* 247, 1465-1468) or (b) administering a nucleic acid molecule packaged as a recombinant virus or as a recombinant cell (i.e., the nucleic acid molecule is delivered by a viral or cellular vehicle).

A naked nucleic acid molecule of the present invention includes a nucleic acid molecule of the present invention and preferably includes a recombinant molecule of the present invention that preferably is replication, or otherwise amplification, competent. A naked nucleic acid of the present invention can comprise one or more nucleic acid molecules of the present invention in the form of, for example, a bicistronic recombinant molecule having, for example one or more internal ribosome entry sites. Preferred naked nucleic acid molecules include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid molecules of the present invention can be administered by a variety of methods. Suitable delivery methods include, for example, intramuscular injection, subcutaneous injection, intradermal injection, intradermal scarification, particle bombardment, oral application, and nasal application, with intramuscular injection, intradermal injection, intradermal scarification and particle bombardment being preferred, and intramuscular injection being even more preferred. A preferred single dose of a naked DNA molecule ranges from about 1 nanogram (ng) to about 1 milligram (mg), depending on the route of administration and/or method of delivery, as can be determined by those skilled in the art. Examples of administration methods are disclosed, for example, in U.S. Pat. No. 5,204,253, by Bruner, et al., issued Apr. 20, 1993, PCT Publication No. WO 95/19799, published Jul. 27, 1995, by McCabe, and PCT Publication No. WO 95/05853, published Mar. 2, 1995, by Carson, et al. Naked DNA molecules of the present invention can be contained in an aqueous excipient (e.g., phosphate buffered saline) and/or with a carrier (e.g., lipid-based vehicles), or it can be bound to microparticles (e.g., gold particles).

A recombinant virus of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, picornaviruses and retroviruses. Preferred recombinant viruses are those based on alphaviruses (such as Sindbis virus), raccoon poxviruses, species-specific herpesviruses and species-specific poxviruses. An example of methods to produce and use alphavirus recombinant virus is disclosed in PCT Publication No. WO 94/17813, by Xiong et al., published Aug. 18, 1994, which is incorporated by reference herein in its entirety.

When administered to an animal, a recombinant virus of the present invention infects cells within the recipient animal and directs the production of a protein or RNA nucleic acid molecule that is capable of reducing Der HMW-map protein-mediated biological responses in the animal. For example, a recombinant virus comprising a Der HMW-map nucleic acid molecule of the present invention is administered according to a protocol that results in the animal producing an amount of protein or RNA sufficient to reduce Der HMW-map protein-mediated biological responses. A preferred single dose of a recombinant virus of the present invention is from about $1 \times 10^4$ to about $1 \times 10^7$ virus plaque forming units (pfu) per kilogram body weight of the animal. Administration protocols are similar to those described herein for protein-based compositions, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli, Listeria, Mycobacterium, S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to desensitize an animal against mite allergy can be tested in a variety of ways including, but not limited to, using in vivo skin test methods disclosed herein, detection of cellular immunity activity in the treated animal, or determine levels of IgE that bind specifically to a Der HMW-map protein of the present invention. Methods to determine cellular immunity activity and IgE levels in an animal are known to those of skill in the art. In one embodiment, therapeutic compositions can be tested in animal models such as dogs, cats, rabbits and mice, and can also be tested in humans. Such techniques are known to those skilled in the art.

Preferred nucleic acid molecules to use with a therapeutic composition of the present invention include any Der HMW-map nucleic acid molecule disclosed herein, in particular SEQ ID NO:14, SEQ ID NO:16, SEQ ID NO:17, SEQ ID NO:19, SEQ ID NO:20, SEQ ID NO:22, SEQ ID NO:34, SEQ ID NO:36, SEQ ID NO:37, SEQ ID NO:39, SEQ ID NO:40, SEQ ID NO:42, SEQ ID NO:43, SEQ ID NO:45 and/or a nucleic acid sequence encoding a protein comprising the amino acid sequence SEQ ID NO:33 and a complement thereof.

A recombinant cell useful in a therapeutic composition of the present invention includes recombinant cells of the present invention that comprises Der HMW-map protein of the present invention. Preferred recombinant cells for this embodiment include *Salmonella, E. coli, Listeria, Mycobacterium, S. frugiperda*, yeast, (including *Saccharomyces cerevisiae*), BHK, CV-1, myoblast G8, COS (e.g., COS-7), Vero, MDCK and CRFK recombinant cells. A recombinant cell of the present invention can be administered in a variety of ways but have the advantage that they can be administered orally, preferably at doses ranging from about $10^8$ to about $10^{12}$ cells per kilogram body weight. Administration protocols are similar to those described herein for protein compositions. Recombinant cells can comprise whole cells, cells stripped of cell walls or cell lysates.

One embodiment of the present invention is a method of immunotherapy comprising administering to an animal an effective amount of a therapeutic composition comprising a Der HMW-map protein of the present invention. Suitable therapeutic compositions and methods of administration are disclosed herein. According to the present invention, a therapeutic composition and method of the present invention can be used to prevent or alleviate symptoms associated with mite allergen pathogenesis.

The efficacy of a therapeutic composition of the present invention to effect an allergic response to Der HMW-map protein can be tested using standard methods for detecting Der HMW-map protein-mediated immunity including, but not limited to, immediate hypersensitivity, delayed hypersensitivity, antibody-dependent cellular cytotoxicity (ADCC), immune complex activity, mitogenic activity, histamine release assays and other methods such as those described in Janeway et al., ibid.

The present invention also includes a therapeutic composition comprising one or more therapeutic compounds of the present invention. Examples of such therapeutic compounds include, for example, other allergens disclosed herein.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), Flt-3 ligand, erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a therapeutic composition of the present invention into the blood of an animal at a constant rate sufficient to attain therapeutic dose levels of the composition to reduce mite allergy in the animal. As used herein, mite allergy refers to cellular responses that occur when mite allergens contact an animal. For example, IgE that specifically binds to mite allergen becomes coupled with Fc epsilon receptor, resulting in Fc epsilon receptor-mediated biological response including release of biological mediators, such as histamine, prostaglandins and/or proteases, that can trigger clinical symptoms of allergy. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be sterilized by conventional methods which do not result in protein degradation (e.g., filtration) and/or lyophilized.

A therapeutic composition of the present invention can be administered to any animal susceptible to mite allergy as herein described. Acceptable protocols by which to administer therapeutic compositions of the present invention in an effective manner can vary according to individual dose size, number of doses, frequency of dose administration, and mode of administration. Determination of such protocols can be accomplished by those skilled in the art. An effective dose refers to a dose capable of treating an animal against hypersensitivity to mite allergens. Effective doses can vary depending upon, for example, the therapeutic composition used and the size and type of the recipient animal. Effective doses to immunomodulate an animal against mite allergens include doses administered over time that are capable of alleviating a hypersensitive response by an animal to mite allergens. For example, a first tolerizing dose can comprise an amount of a therapeutic composition of the present invention that causes a minimal hypersensitive response when administered to a hypersensitive animal. A second tolerizing dose can comprise a greater amount of the same therapeutic composition than the first dose. Effective tolerizing doses can comprise increasing concentrations of the therapeutic composition necessary to tolerize an animal such that the animal does not have a hypersensitive response to exposure to mite allergens. An effective dose to desensitize an animal can comprise a concentration of a therapeutic composition of the present invention sufficient to block an animal from having a hypersensitive response to exposure to a mite allergen present in the environment of the animal. Effective desensitizing doses can include repeated doses having concentrations of a therapeutic composition that cause a minimal hypersensitive response when administered to a hypersensitive animal.

A suitable single dose is a dose that is capable of treating an animal against hypersensitivity to mite allergens when administered one or more times over a suitable time period. For example, a preferred single dose of a mite allergen, or mimetope therapeutic composition is from about 0.5 ng to about 1 g of the therapeutic composition per kilogram body weight of the animal. Further treatments with the therapeutic composition can be administered from about 1 day to 1 year after the original administration. Further treatments with the therapeutic composition preferably are administered when the animal is no longer protected from hypersensitive responses to mite allergens. Particular administration doses and schedules can be developed by one of skill in the art based upon the parameters discussed above. Modes of administration can include, but are not limited to, subcutaneous, intradermal, intravenous, nasal, oral, transdermal and intramuscular routes.

A therapeutic composition of the present invention can be used in conjunction with other compounds capable of modifying an animal's hypersensitivity to mite allergens. For example, an animal can be treated with compounds capable of modifying the function of a cell involved in a hypersensitive response, compounds that reduce allergic reactions, such as by systemic agents or anti-inflammatory agents (e.g., anti-histamines, anti-steroid reagents, anti-inflammatory reagents and reagents that drive immunoglobulin heavy chain class switching from IgE to IgG). Suitable compounds useful for modifying the function of a cell involved in a hypersensitive response include, but are not limited to, antihistamines, cromolyn sodium, theophylline, cyclosporin A, adrenalin, cortisone, compounds capable of regulating cellular signal transduction, compounds capable of regulating adenosine 3',5'-cyclic phosphate (cAMP) activity, and compounds that block IgE activity, such as peptides from IgE or IgE specific Fc receptors, antibodies specific for peptides from IgE or IgE-specific Fc receptors, or antibodies capable of blocking binding of IgE to Fc receptors.

Compositions of the present invention can be administered to any animal having or susceptible to mite allergen hypersensitivity. Preferred animals to treat include mammals and birds, with felines, canines, equines, humans and other pets, work and/or economic food animals. Particularly preferred animals to protect are felines and canines.

Another aspect of the present invention includes a method for prescribing treatment for animals susceptible to or having hypersensitivity to mite allergens, using a formulation of the present invention. A preferred method for prescribing treatment for mite allergen hypersensitivity, for example, comprises: (1) intradermally injecting into an animal at one site an effective amount of a formulation containing a mite allergen of the present invention, or a mimetope thereof (suitable and preferred formulations are disclosed herein); (2) intradermally injecting into the animal at a second site an effective amount of a control solution; (3) evaluating if the animal has mite allergen hypersensitivity by measuring and comparing the wheal size resulting from injection of the formulation with the wheal size resulting from injection of the control solution; and (4) prescribing a treatment for the mite allergen hypersensitivity.

An alternative preferred method for prescribing treatment for mite allergen hypersensitivity comprises: (1) contacting a first portion of a sample of bodily fluid obtained from an animal to be tested with an effective amount of a formulation containing mite allergen, or a mimetope thereof (suitable and preferred formulations are disclosed herein) to form a first immunocomplex solution; (2) contacting a positive control antibody to form a second immunocomplex solution; (3) evaluating if the animal has mite allergen hypersensitivity by measuring and comparing the amount of immunocomplex formation in the first and second immunocomplex solutions; and (4) prescribing a treatment for the mite allergen hypersensitivity. It is to be noted that similar methods can be used to prescribe treatment for allergies using mite allergen formulations as disclosed herein.

Another aspect of the present invention includes a method for monitoring animals susceptible to or having mite allergen hypersensitivity, using a formulation of the present invention. In vivo and in vitro tests of the present invention can be used to test animals for mite allergen hypersensitivity prior to and following any treatment for mite allergen hypersensitivity. A preferred method to monitor treatment of mite allergen hypersensitivity (which can also be adapted to monitor treatment of other allergies) comprises: (1) intradermally injecting an animal at one site with an effective amount of a formulation containing mite allergen, or a mimetope thereof (suitable and preferred formulations are disclosed herein); (2) intradermally injecting an effective amount of a control solution into the animal at a second site; and (3) determining if the animal is desensitized to mite allergens by measuring and comparing the wheal size resulting from injection of the formulation with the wheal size resulting from injection of the control solution.

An alternative preferred method to monitor treatment of mite allergen hypersensitivity (which can be adapted to monitor treatments of other allergies) comprises: (1) contacting a first portion of a sample of bodily fluid obtained from an animal to be tested with an effective amount of a formulation containing a mite allergen or mimetope thereof (suitable and preferred formulations are disclosed herein) to form a first immunocomplex solution; (2) contacting a positive control antibody to form a second immunocomplex solution; and (3) determining if the animal is desensitized to mite allergens by measuring and comparing the amount of immunocomplex formation in the first and second immunocomplex solutions.

The present invention also includes antibodies capable of selectively binding to mite allergen, or mimetope thereof. Such an antibody is herein referred to as an anti-mite allergen antibody. As used herein, the term "selectively binds to" refers to the ability of such an antibody to preferentially bind to mite allergens and mimetopes thereof. In particular, the present invention includes antibodies capable of selectively binding to Der HMW-map protein. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to Der HMW-map proteins, or mimetopes thereof. More preferred Der HMW-map protein against which to raise an antibody includes at least a portion of a protein having the amino acid sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:18, SEQ ID NO:21, SEQ ID NO:23, SEQ ID NO:24, SEQ ID NO:30, SEQ ID NO:31, SEQ ID NO:32, SEQ ID NO:33, SEQ ID NO:33, SEQ ID NO:35, SEQ ID NO:38, SEQ ID NO:41, and/or SEQ ID NO:44, or homologs thereof. Preferably, an antibody of the present invention has a single site binding affinity of from about $10^3 M^{-1}$ to about $10^{12} M^{-1}$ for a Der HMW-map protein of the present invention.

A preferred method to produce antibodies of the present invention includes administering to an animal an effective amount of a Der HMW-map protein or mimetope thereof to produce the antibody and recovering the antibodies. Antibodies raised against defined products or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from mite allergen hypersensitivity, (b) as positive controls in test kits, and/or (c) as tools to recover desired mite allergens from a mixture of proteins and other contaminants.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., and related references.

Example 1

This example describes the identification of high molecular weight proteins that bind to IgE from dogs known to be allergic to mite allergens.

About 5.5 grams (g) of frozen wet *Dermataphagoides farinae* (Der f) mites (available from Bayer Allergy, Spokane, Wash.) were homogenized in a ground glass homogenizer, in either about 30 ml of phosphate buffered saline (PBS) or 0.1 M Tris-HCl, pH 8, each containing complete protease inhibitors (available from Boehringer Mannheim, Indianapolis, Ind.) to obtain a Der f crude extract. The resulting supernatants were collected and each concentrated in a Centriprep 30 concentrator (available from Amicon, Beverly, Mass.) by centrifugation at 16,000×g for about 30 minutes. The concentrated supernatants were applied to separate Sephacryl S-100 columns (2.7×70 cm; available from Pharmacia, Piscataway, N.J.) in PBS or 0.1 M Tris-HCl, pH 8, respectively. The excluded fractions from each column were pooled. Fractions were dialyzed against 10 mM Tris-HCl, pH 8, when PBS was used. The fractions were applied to separate Q-Sepharose columns (2.5×5 cm; available from Pharmacia). The Q-Sepharose column was pre-equilibrated in 10 mM Tris-HCl, pH 8, when the fractions containing 0.1 M Tris-HCl, pH 8 were used. Each column was sequentially eluted with about 45 ml of 10 mM Tris-HCl, pH 8, then 0.1 M Tris-HCl, pH 8, then 0.2 M Tris-HCl, pH 8, then 0.3 M Tris-HCl, pH 8, then 0.4 M Tris-HCl, pH 8 and then 0.5 M Tris-HCl, pH 8. Fractions were collected from each elution step. Each fraction was analyzed by western blot for the presence of protein that bound to IgE antibodies present in dog sera isolated from dogs known to be allergic to mite allergens (referred to herein as mite allergic dog antisera or mite allergic antisera). Specifically, proteins contained in the fractions were resolved by 12% Tris-glycine SDS-PAGE and then blotted onto nitrocellulose. The blot was incubated with a pool of sera obtained from dogs known to be allergic to mite allergens, diluted 1:20, using standard buffers. The blot was incubated and then washed using standard procedures. The blot was then incubated with the mouse monoclonal anti-dog IgE antibody DEI38 (1 mg/ml, 1:1000 dilution). The blot was incubated and then washed using standard procedures. The blot was then incubated with donkey anti-mouse IgG antibody conjugated to horseradish peroxidase (1:1000 dilution; available from Jackson Labs, Maine). The presence of HRP-conjugated antibody bound to the blot was detected using standard techniques. An about 70-kD protein was identified in the 0.2 M Tris-HCl, pH 8 fraction, an about 98-kD protein and an about 109-kD protein were identified in the 0.3 M Tris-HCl, pH 8 fraction.

The fraction described above that was eluted using 0.3 M Tris-HCl, pH 8 was concentrated in a Centriprep 30 concentrator and then diluted in 20 mM Na-Ac, pH 5.6. The diluted fraction was then applied to a PolyCat A HPLC cation exchange column (available from PolyLC, Columbia, Md.). The column was eluted with about 10 ml of 20 mM Na—Ac, pH 5.6, and then with about 45 ml of a linear gradient from 0 to 0.5 M NaCl in the 20 mM Na—Ac, pH 5.6 buffer at a flow rate of about 1 ml/min. Fractions were collected from the elution procedure and assayed for the presence of high molecular weight proteins using the mite allergic antisera and western blot protocol described above. Fractions containing the high molecular weight proteins were pooled. Trifluoroacetic acid (TFA) was added to a concentration of about 0.05%. The solution was applied to a TSK-Gel TMS-250 C1 reverse phase column (available from TosoHaas, Montgomeryville, Pa.) that had been pre-equilibrated in 80% solvent A and 20% solvent B. Solvent A was composed of about 0.05% TFA in water and solvent B was composed of about 0.05% TFA in 90% acetonitrile in water. The column was eluted with about 5 ml of 20% solvent B and then with 36 ml of a linear gradient of about 20% to about 70% solvent B at 0.6 m/min. The proteins eluted from the column were resolved by 12% Tris-Glycine PAGE. The gel was stained with Comassie blue. The stained gel is shown in FIG. 1. Lane 1 contains Mark-12 protein molecular weight markers (available from Novex, San Diego, Calif.), lane 2 contains the protein eluted from the reverse phase column, and lane 3 contains SeeBlue™ protein molecular weight markers (available from Novex). Two major proteins were identified in the eluant. The molecular weights of the proteins were determined using a BioRad™ Multi-Analyst™/PC Image System (available from BioRad Corp.). The higher molecular weight protein in lane 2 of FIG. 1 was determined to be about 109 kD, referred to herein as mite allergen protein A (mapA). The lower molecular weight protein in lane 2 of FIG. 1 was determined to be about 98 kD, referred to herein as mite allergen protein B (mapB). The purity of the combined proteins was greater than 85% purity, i.e., less than 15% impurities. This purified eluant is referred to herein as the *D. farinae* high molecular weight map (HMW-map) composition.

Example 2

This example describes N-terminal sequencing of proteins in the *D. farinae* HMW-map composition.

Proteins contained in the 0.3 M Tris-HCl, pH 8 fraction obtained as described above in Example 1 were resolved by SDS-PAGE using a 12% Tris-glycine polyacrylamide-SDS gel, followed by coomasie staining. The proteins were blotted onto PVDF, stained with Coomasie R-250 and destained using standard procedures. The proteins corresponding to the about 98 kD and about 109 kD bands were excised and subjected separately to N-terminal amino acid sequencing using techniques known to those skilled in the art. A partial N-terminal amino acid sequence of about 14 amino acids was deduced for both proteins and the sequences were determined to be identical. The N-terminal amino acid sequence is represented herein as SEQ ID NO:1, having the amino acid sequence: Ser Ile Lys Arg Asp His Asn Asp Tyr Ser Lys Asn Pro Met.

The proteins in the *D. farinae* HMW-map composition were also submitted to proteolytic cleavage in order to obtain internal amino acid sequence data. Specifically, the *D. farinae* HMW-map composition was cleaved with Endoproteinase Asp-N (available from Boehringer Mannheim Biochemica, Indianapolis, Ind.) using methods standard in the art. The digested protein was then resolved by HPLC using the method described by Stone et al., Enzymatic Digestion of Proteins and HPLC Peptide Isolation, in A Practical Guide to Protein and Peptide Purification for Microsequencing, PT Matsudaira ed., Academic Press, San Diego, Calif. Twelve proteolytic fragments were isolated, that are referred to herein as map(1), map(2), map(3), map(4), map(5), map(6), map(7), map(8), map(9), map(10), map(11) and map(12).

The N-terminal partial amino acid sequence of map(1) was determined to be Asp Tyr Glu Tyr Pro Gly Ser Arg Leu Gly Asn Pro Lys Ala Pro Leu Tyr Lys Arg Pro, also denoted SEQ ID NO:2. The N-terminal partial amino acid sequence of map(2) was determined to be Asp Ile Pro His Pro Thr Asn Ile His Lys Tyr Leu Val Cys Glu Ser Val Asn Gly Gly, also denoted SEQ ID NO:3. The N-terminal partial amino acid sequence of map(3) was determined to be Asp Pro Ala Lys Gly Met Ser Pro Pro Gly Phe Ile Val Gly Glu Glu Gly Val Leu Ser, also denoted SEQ ID NO:4. The N-terminal partial amino acid sequence of map(4) was determined to be Asp Glu Lys Asn Ser Phe Glu Cys Ile Leu Gly Pro, also denoted SEQ ID NO:5. The N-terminal partial amino acid sequence of map(5) was determined to be Asp Ala Phe Glu Pro His Gly Tyr Leu Leu Thr Ala Ala Val Ser Pro Gly Lys, also denoted SEQ ID NO:6. The N-terminal partial amino acid sequence of map(6) was determined to be Asp Lys Gln Asn Tyr Leu Ala Leu Val Arg Glu Leu Lys, also denoted SEQ ID NO:7. The N-terminal partial amino acid sequence of map (7) was determined to be Asp Met Ala Gln Asn Tyr Lys Tyr Arg Gln Gln Phe Ile Gln Ser Val Leu Asn Asn Gly Ala Thr Arg Gln, also denoted SEQ ID NO:8. The N-terminal partial amino acid sequence of map(8) was determined to be Asp Glu Xaa Asn Val Met Xaa Tyr Val Leu Tyr Thr Met His Tyr Tyr Leu Asn Asn Gly Ala Thr Arg, also denoted SEQ ID NO:9, in which Xaa represents any amino acid. The N-terminal partial amino acid sequence of map(9) was determined to be Asp Lys Leu Val Met Gly Val Pro Phe Tyr Gly Arg Ala Xaa Ser Ile Glu, also denoted SEQ ID NO:10, in which Xaa represents any amino acid. The N-terminal partial amino acid sequence of map(10) was determined to be Asp Ile Pro His Pro Thr Asn Ile His Lys Tyr Leu Val Cys Glu Ser Val Asn Gly, also denoted SEQ ID NO:11. The N-terminal partial amino acid sequence of map(11) was determined to be Asp Tyr Ala Lys Asn Pro Lys Arg Ile Val Cys Ile Val Gly Thr Glu Gly Val Leu Ser, also denoted SEQ ID NO:12. The N-terminal partial amino acid sequence of map(12) was determined to be Asp Pro Ala Lys Gly Met Ser Pro Pro Gly He Ile Val Gly Glu Glu Gly Val Leu Ser, also denoted SEQ ID NO:13. Since the amino acid sequences for map(1), map(2), map(3), map(4), map(5), map(6), map(7), map(8), map(9), map(10), map(11), map(12), and map(13) were generated from a mixture of mapA and mapB proteins, these sequences do not necessarily represent partial sequences of a single protein.

Example 3

This example describes the purification of a 70-kD protein that binds to IgE from dogs known to be allergic to mite allergens.

The fraction described above in Example 1 that was eluted using 0.2 M Tris-HCl, pH 8 was concentrated in a Centriprep 30 concentrator and then diluted in 20 mM Na—Ac, pH 5.6. The diluted protein was then applied to a PolyCat A HPLC cation exchange column. The column was eluted with about 10 ml of 20 mM Na—Ac, pH 5.6, and then with about 45 ml of a linear gradient from 0 to 0.5 M NaCl in the 20 mM Na—Ac, pH 5.6 buffer at a flow rate of about 1 ml/min. Fractions were collected from the elution procedure and assayed for the presence of 70-kD protein using the mite allergic antisera and western blot protocol described above. Fractions containing the 70-kD protein were pooled. Trifluoroacetic acid (TFA) was added to a concentration of about 0.05%. The solution was applied to a TSK-Gel TMS-250 C1 reverse phase column that had been pre-equilibrated in 80% solvent A and 20% solvent B. Solvent A was composed of about 0.05% TFA in water and solvent B was composed of about 0.05% TFA in 90% acetonitrile in water. The column was eluted with about 3 ml of 20% solvent B and then with 36 ml of a linear gradient of about 20% to about 70% solvent B at 0.6 ml/min. An about 70-kD protein of >90% purity was obtained. The about 70-kD protein is referred to herein as mapC.

N-terminal sequence of a region on an SDS-PAGE corresponding to the 70 kD protein (mapC) was obtained as described in Example 2. An N-terminal amino acid sequence of about 21 amino acids was deduced with an 80% confidence level, and is represented herein as SEQ ID NO:33, having the following amino acid sequence: Gln Ser Arg Asp Arg Asn Asp Lys Pro Tyr Xaa Ile Val Lys Lys Lys Lys Ala Leu Asp.

Example 4

This example describes the binding of the *D. farinae* HMW-map composition (i.e., containing mapA and mapB) to canine IgE in dog sera isolated from dogs known to be allergic to mite allergens.

Multiple wells of an Immulon II microtiter plate were coated with about 100 nanograms per well (ng/well) of a *D. farinae* HMW-map composition isolated according to the method described above in Example 1, diluted in CBC buffer. The plate was incubated overnight at 4° C. Following incubation, the *D. farinae* HMW-map composition-containing solution was removed from the plate, and the plate was blotted dry. The plate was then blocked using about 200 μl/well of 4.0% fetal calf serum contained in phosphate buffered saline (PBS) having 0.05% Tween-20 (PBSTFCS) for about 1 hour at room temperature. The plate was then washed four times with 0.05% Tween-20 in PBS (PBST) using an automatic washer (available from Dynatech, Chantilly, Va.). About 100 μl/well of a 1:10 dilution in PBSTFCS of serum samples isolated from different dogs known to be sensitive to mite allergens in intradermal skin tests were added to the plate. A negative control group of sera was also added to the plate comprising a combination of sera from six dogs that were raised in a barrier facility (available from Harlan Bioproducts, Indianapolis, Ind.). Some wells did not receive dog sera so that background binding levels could be determined. The plate was incubated for about 1 hour at room temperature and then washed four times with PBST. About 100 μl/well of a 1:4000 dilution of 40 μg/ml biotinylated human FceR alpha chain protein (produced as described in Frank et al., WO 98/23964, published Nov. 24, 1997) contained in PBSTFCS was added. The plate was incubated for about 1 hour at room temperature and then washed four times with PB ST. About 100 μl of about 0.25 μg/ml streptavidin conjugated to horseradish peroxidase (available from Kirkegaard and Perry Laboratories (KPL), Gaithersburg, Md.; diluted in PBST) was added to each well that received experimental or control samples. The plates were then incubated for about 1 hour at room temperature and washed four times with PBST. About 100 μl of TMB substrate (available from KPL), that had been pre-warmed to room temperature, was added to each well. The plate was then incubated for about 10 minutes at room temperature and then about 100 μl/well of Stop Solution (available from KPL) was added. Optical densities (O.D.) of wells were read on a Spectramax Microtiter Plate (available from Molecular Devices Inc.) reader at 450 nm within 10 minutes of adding the stop solution.

The O.D. readings obtained using the negative control sample and the background wells were 0 O.D. Sera from 5 of 26 mite allergen sensitive dogs generated O.D. readings between about 2,000 O.D. and about 3,200 O.D. Sera from 3 other mite allergen sensitive dogs generated O.D. readings between about 1,000 O.D. and 2,000 O.D. Sera from 3 other mite allergen sensitive dogs generated O.D. readings between about 500 O.D. and 1,000 O.D. Sera from 7 other mite allergen sensitive dogs generated O.D. readings between about 200 O.D. and 500 O.D. Sera from 6 other mite allergen sensitive dogs generated O.D. readings less than 50 O.D. Thus, the results indicate that sera from dogs known to be sensitive to mite allergens contain IgE antibodies that bind specifically to the mapA and mapB proteins of the present invention.

Example 5

This example describes the binding of the 70-kD *D. farinae* protein to canine IgE in dog sera isolated from dogs known to be allergic to mite allergens.

Multiple wells of an Immulon II microtiter plate were coated with about 100 ng/well of 70-kD *D. farinae* protein (referred to herein as mapC) isolated according to the method described above in Examples 1 and 3, diluted in CBC buffer. The plate was incubated overnight at 4° C. The plate was blocked and washed using the method described in Example 4. About 100 µl/well of a 1:10 dilution in PBST-FCS of serum samples isolated from different dogs known to be sensitive to mite allergens in intradermal skin tests were added to the plate. Negative control samples were also added to the plate comprising SPF serum samples (serum from dogs maintained in a barrier facility and therefore never exposed to mite allergens). Some wells did not receive dog sera so that background binding levels could be determined. The plate was incubated for about 1 hour at room temperature and then washed four times with PBST. Biotinylated human FceR alpha chain protein was then added and the presence of IgE bound to the plate was detected using the methods described in Example 4.

The O.D. readings obtained using the negative control sample and the background wells were 0 O.D. Sera from 3 of 26 mite allergen sensitive dogs generated O.D. readings between about 1,500 O.D. and about 2,700 O.D. Sera from 5 other mite allergen sensitive dogs generated O.D. readings between about 800 and about 1,500 O.D. Sera from 4 other mite allergen sensitive dogs generated O.D. readings between about 500 O.D. and about 800 O.D. Sera from 6 other mite allergen sensitive dogs generated O.D. readings between about 200 O.D. and 500 O.D. Sera from 8 other mite allergen sensitive dogs generated O.D. readings less than 50 O.D. Thus, the results indicate that sera from dogs known to be sensitive to mite allergens contain IgE antibodies that bind specifically to the mapC protein of the present invention.

Example 6

This example describes the binding of mapA, mapB or mapC proteins to feline IgE in cat sera isolated from cats shown by in vitro testing to be hypersensitive to mite allergens.

Multiple wells of an Immulon II microtiter plate were coated with about 100 ng/well of a *D. farinae* HMW-map composition (isolated according to the method described above in Example 1) and 70-kD *D. farinae* protein (isolated according to the method described above in Example 3). Other wells of the plate were coated with 400 ng/well of whole *Dermatophagoides pteronyssius* extract (available from Greer Laboratories, Inc., Lenoir, N.C.; concentrated 8-fold prior to use) or whole *D. farinae* extract (available from Miles, Inc., Elkhart, Ind.). All samples were diluted in CBC buffer. The plates were incubated overnight at 4° C. The plates were blocked and washed using the method described in Example 4. About 100 µl/well of a 1:10 dilution in PBSTFCS of serum samples isolated from different cats known to be sensitive to mite allergens in in vitro allergen testing were added to the plate. Sera from seven control cats (#15, #16, #17, #18, #19, #20, and #21), shown not to be sensitive by in vitro test to dust mite allergens, were also tested. Some wells did not receive cat sera so that background binding levels could be determined. The plate was incubated for about 1 hour at room temperature and then washed four times with PBST. Biotinylated human FceR alpha chain protein was then added and the presence of IgE bound to the plate was detected using the methods described in Example 4.

The results are shown below in Table 1. All values represent O.D. values times 1,000. HDM refers to cats that are sensitive to house dust mite allergens (by serological test, i.e. an ELISA to whole *D. farinae* extract).

TABLE 1

| Cat # | HDM | Whole Der p | Whole Der f | mapA and mapB | mapC |
|---|---|---|---|---|---|
| 1 | + | 54 | 173 | 211 | 400 |
| 2 | + | 437 | 454 | 245 | 352 |
| 3 | + | 96 | 88 | 17 | 36 |
| 4 | + | 35 | 179 | 278 | 758 |
| 5 | + | 123 | 23 | 0 | 0 |
| 6 | + | 2 | 10 | 0 | 0 |
| 7 | + | 84 | 321 | 439 | 445 |
| 8 | + | 125 | 333 | 611 | 599 |
| 9 | + | 2459 | 2737 | 1613 | 507 |
| 10 | + | 17 | 0 | 0 | 0 |
| 11 | + | 146 | 347 | 243 | 586 |
| 12 | + | 31 | 100 | 102 | 223 |
| 13 | + | 56 | 171 | 267 | 292 |
| 14 | + | 121 | 146 | 163 | 185 |
| 15 | − | 0 | 0 | 0 | 8 |
| 16 | − | 0 | 0 | 0 | 0 |
| 17 | − | 0 | 0 | 0 | 0 |
| 18 | − | 0 | 0 | 0 | 0 |
| 19 | − | 0 | 0 | 0 | 0 |
| 20 | − | 0 | 0 | 0 | 0 |
| 21 | − | 23 | 0 | 0 | 0 |

The results indicate that sera from some of the cats known to be sensitive to mite allergens contain IgE antibodies that bound specifically to the mapA, mapB or mapC proteins of the present invention. In addition, some sera containing IgE that bound to the mapA, mapB or mapC proteins also contain IgE antibodies that bound to whole *D. pteronyssius* extract. The control sera did not contain IgE antibodies that bound to either the mapA, mapB or mapC proteins of the present invention.

Example 7

This example demonstrates the ability of the *D. farinae* HMW-map composition to induce a hypersensitive response in dogs.

To determine whether the *D. farinae* HMW-map composition described in Example 1 was capable of inducing an allergic response in animals susceptible to dust mite allergic responses, skin tests were performed on dogs that actively demonstrate clinical signs for dust mite allergy (referred to herein as atopic dogs). Normal dogs include dogs that do not show symptoms of mite allergy but may be susceptible to a mite allergic response. Each dog (i.e., 4 normal and 4 atopic dogs) was shaved in the lateral thorax/abdominal area and intradermally injected in different sites in that area with an about 1:50,000 dilution of *D. farinae* crude extract isolated by the method described in Example 1, with about 2 µg of the purified *D. farinae* HMW-map composition and/or with control solutions, i.e., saline, as a negative control, and a 1:1000 dilution of histamine as a positive control. All four normal dogs and all 4 atopic dogs received *D. farinae* whole extract. Three of the normal dogs and 2 of the atopic dogs received the *D. farinae* HMW-map composition. All 8 of the dogs received both the negative and positive control samples. The total volume per injection was 50 microliters (µl), with the compositions and controls being diluted in saline. The injections were administered as single injections.

All injection sites were objectively measured in millimeters (mm) at 15 minutes and scored either (+) or (−) when compared with the control samples. The subjective scoring was performed by Andrew Hillier, D.V.M., at Ohio State University, Columbus, Ohio. The results are shown in Table 2:

TABLE 2

|  | Normal Dog 1 | Normal Dog 2 | Normal Dog 3 | Normal Dog 4 | Atopic Dog 1 | Atopic Dog 2 | Atopic Dog 3 | Atopic Dog 4 |
| --- | --- | --- | --- | --- | --- | --- | --- | --- |
| Whole Extract | + | + | + | − | + | + | − | − |
| HMW map | + | + | − | n/a | + | − | n/a | n/a |
| Neg. Control | − | − | − | − | − | − | − | − |
| Histamine | + | + | + | + | + | + | + | + | n/a = not applicable

The results indicate that the *D. farinae* HMW-map composition was capable of inducing an immediate hypersensitive response in dogs including atopic dogs. Thus, the HMW-map composition is sufficiently allergenic to induce a hypersensitive response in dogs including atopic dogs.

Table 3 describes the results of the following experiment. IgE to the HMW-map composition was measured in the serum of three groups of dogs: *D. farinae* allergic (HDM-AD), atopic (to other allergens) but not HDM allergic (AD), and naive dogs using ELISA. These dogs were also tested by intradermal skin test to *D. farinae* whole extract and to the HMW-map composition.

TABLE 3

Skin test and ELISA data for *D. farinae* whole extract and for HMW-map composition in *D. farinae*-allergic, atopic but not HDM-allergic, and naive dogs.

| Dog | Clinical status | Df IDST 1:50,000 | Df ELISA | HMW-map IDST 1 ug | HMW-map ELISA |
| --- | --- | --- | --- | --- | --- |
| 1 | HDM-AD | + | 1968 | + | 2876 |
| 2 | HDM-AD | + | 407 | − | 954 |
| 3 | HDM-AD | + | 3921 | + | 3465 |
| 4 | HDM-AD | + | 153 | + | 198 |
| 5 | HDM-AD | + | 1712 | + | 997 |
| 6 | HDM-AD | + | 1833 | + | 2006 |
| 7 | HDM-AD | + | 4200 | + | 4200 |
| 8 | HDM-AD | + | 2851 | + | 3559 |
| 9 | HDM-AD | + | 122 | + | 209 |
| 10 | HDM-AD | + | 1627 | + | 566 |
| 11 | HDM-AD | + | 1185 | + | 1307 |
| 12 | HDM-AD | + | 308 | + | 101 |
| 13 | HDM-AD | + | 341 | + | 433 |
| 14 | AD | − | 1 | − | 0 |
| 15 | AD | − | 8 | − | 2 |
| 16 | AD | ND | 66 | ND | 87 |
| 17 | Normal | − | 24 | − | 40 |
| 18 | Normal | − | 53 | ND | 369 |
| 19 | Normal | − | 37 | − | 21 |
| 20 | SPF beagle | ND | 0 | ND | 0 |
| 21 | SPF beagle | ND | 6 | ND | 1 |

All dogs that were positive by ELISA for whole *D. farinae* extract were also positive for the HMW-map composition allergen. Of the eight dogs that were ELISA negative for whole *D. farinae* extract, 7 of 8 were also negative for the HMW-map composition.

Example 8

This example describes the isolation of nucleic acid molecules encoding a Der HMW-map composition of the present invention.

Der HMW-map composition nucleic acid molecules were identified and isolated as follows.

A. Preparation of a *Dermatophagoides farinae* cDNA Library.

A *Dermatophagoides farinae* cDNA library was prepared as follows. Total RNA was extracted from about 2 grams of flash frozen and pulverized house dust mites, using an acid-guanidinium-phenol-chloroform method similar to that described by Chomzynski et al., 1987, *Anal. Biochem.* 162,156-159. Poly A$^+$ selected RNA was separated from the total RNA preparation by oligo-dT cellulose chromatography using the mRNA Purification Kit (available from Pharmacia Biotech, Newark, N.J.), according to the method recommended by the manufacturer. A cDNA library was constructed in lambda-Uni-ZAP™ XR vector (available from Stratagene), using Stratagene's ZAP-cDNA Synthesis Kit protocol. Approximately 5 µg of Poly A$^+$ RNA was used to produce the *Dermatophadoides farinae* cDNA library.

B. Preparation of PCR Primers.

Further N-terminal amino acid sequence analysis was performed according to the methods described above in Example 2. A partial N-terminal amino acid sequence of 34 amino acids was deduced and is represented by SEQ ID NO:24, having the amino acid sequence: Ser Ile Lys Arg Asp His Asn Asp Tyr Ser Lys Asn Pro Met Met Ile Val Xaa Tyr Tyr Gly Gly Ser Ser Gly Tyr Gln Ser Xaa Lys Arg Xaa Xaa Thr (wherein "Xaa" represents any amino acid residue). The amino acid sequences of SEQ ID NO:4 (described above in Example 2) and SEQ ID NO:24 were used to design synthetic oligonucleotide primers. Sense primer Derf1 derived from SEQ ID NO:24, having the nucleotide sequence 5' AAA CGT GAT CAT AAY GAT TAY TCN AAR AAY C 3' (wherein Y represents C or T, R represents A or G, and N represents A, C, T or G), designated SEQ ID NO:25 or sense primer Derf2, derived from SEQ ID NO:24, having the nucleotide sequence 5' AAA CGT GAT CAT AAY GAT TAY AGY AAR AAY C 3', designated SEQ ID NO:26, were used in combination with antisense primer Derf3 derived from SEQ ID NO:4, having the nucleotide sequence 5' CCT TCT TCA CCN ACR ATC AAN CC 3', denoted SEQ ID NO:27, or antisense primer Derf4 derived from SEQ ID NO:4, having the nucleotide sequence 5' CCT TCT TCA CCN ACR ATG AAN CC 3', denoted SEQ ID NO:28.

The foregoing primers were then used to screen the Der f cDNA library using standard polymerase chain reaction amplification (PCR) techniques. All attempts to identify a cDNA that hybridized to the primers failed.

C. Immunoscreening the *D. farinae* cDNA Library Using Anti-Der HMW-Mapcomposition Antibodies.

Since attempts to isolate a cDNA clone using PCR methods failed, the inventors screened the *D. farinae* cDNA library using an antiserum produced as follows. Protein isolated according to the method described above in Example 1 was used as a source of antigen to generate rabbit polyclonal antibodies, referred to herein as anti-Der HMW-map composition antibodies. The preparation of rabbit polyclonal antibodies was carried out using standard techniques.

About 7.5 ml of *Escherichia coli* (XL1 Blue, O.D.$_{600}$=0.5) was incubated with $3.0 \times 10^4$ pfu of phage from a *Dermatophagoides farinae* ZAP-cDNA library ($1.8 \times 10^9$ pfu/ml), at 37° C. for 15 min and plated in 30 ml Luria-Bertani (LB) medium agar plates (150 mm). The plates were incubated at 37° C. over night. Each plate was then overlaid with an IPTG (10 mM) treated nitrocellulose filter for about 4 hours at 37° C. The filters were then removed and washed with Tris buffered saline (pH 7.5) containing 0.1% Tween (TBST), for 5 minutes. The filters were blocked with a solution of 1% dried pwder milk, 1% BSA, 2% goat serum and 0.15% gelatin, prepared in TBST, for 2 hours at room temperature. Filters were then incubated with the anti-Der HMW-map composition antibodies at a dilution of 1:1000, contained in the above blocking solution at 4° C., overnight. The mixture was then incubated with a donkey anti-rabbit IgG antibody conjugated to horseradish peroxidase (available from Jackson ImmunoResearch, West Grove, PN) for 2 hours at room temperature. All of the filters were washed with blocking solution contained in TBST (3×15 min/wash) between each incubation. All of the filters were then treated to a final wash in Tris buffered saline (pH 7.5) for 5 minutes at room temperature. Immunocomplexed plaques were identified by immersing the filters into the developing solution (TMB Peroxidase Substrate/TMB Peroxidase Solution/TMB Membrane Enhancer from Kirkegaard & Perry Laboratories) at 1/1/0.1 volume ratio to produce a color reaction. One hundred and twenty three plaques were identified and 50 plaques were further plaque purified two more times under the same immunoscreening condition as described above.

D. PCR Screening of Purified Phage Plugs

The phage plugs identified in the foregoing immunoscreening study were then further analyzed by PCR amplification using the primers described above in section 8B. DNA from the 50 plaques was amplified using a mixture of the 4 primers identified by SEQ ID NO:25, SEQ ID NO:26, SEQ ID NO:27 and SEQ ID NO:28. PCR amplification was conducted using standard techniques. One resulting PCR amplification product comprised a fragment of about 700 nucleotides. The PCR product was cloned into the InVitrogen, Corp., TA™ cloning vector (procedures provided by InVitrogen, Corp.) and subjected to DNA sequence analysis using standard techniques. The phagemid from the purified phage that were determined to contain sequences encoded in the 700-bp PCR product were rescued and subjected to DNA sequence analysis using standard techniques.

A clone was isolated that included about a 1752-nucleotide insert, referred to herein as nDerf98$_{1752}$. Nucleic acid sequence was obtained using standard techniques from nDerf98$_{1752}$, to yield a *Dermatophagoides farinae* nucleic acid molecule named nDerf98$_{1752}$ composed of a coding strand having nucleic acid sequence SEQ ID NO:14 and a complementary strand having a nucleic acid sequence SEQ ID NO:16. Translation of SEQ ID NO:14 suggests that nucleic acid molecule nDerf98$_{1752}$ encodes a full-length flea protein of about 555 amino acids, referred to herein as PDerf98$_{555}$, having amino acid sequence SEQ ID NO:15, assuming an open reading frame in which the first codon spans from nucleotide 1 through nucleotide 3 of SEQ ID NO:14 and a stop codon spanning from nucleotide 1666 through nucleotide 1668 of SEQ ID NO:14. The amino acid sequence of PDerf98$_{555}$ is encoded by the nucleic acid molecule nDerf98$_{1665}$, having a coding strand with the nucleic acid sequence SEQ ID NO:17 and a complementary strand with the nucleic acid sequence SEQ ID NO:19. PDerf98$_{555}$, also represented by SEQ ID NO:18, has an estimated molecular weight of about 63.2 kD and an estimated pI of about 5.33. Analysis of SEQ ID NO:15 suggests the presence of a signal peptide spanning from about amino acid 1 through about amino acid 19. The proposed mature protein, denoted herein as PDerf$_{536}$, contains about 536 amino acids, the sequence of which is represented herein as SEQ ID NO:21, and is encoded by a nucleic acid molecule referred to herein as nDerf98$_{1608}$, represented by SEQ ID NO:20, the coding strand, and SEQ ID NO:22, the complementary strand. The amino acid sequence of flea PDerf98$_{536}$ (i.e. SEQ ID NO:21) predicts that PDerf98$_{536}$ has an estimated molecular weight of 61.2 kD, and an estimated pI of about 5.26.

Comparison of amino acid sequence SEQ ID NO:15 with amino acid sequences reported in GenBank indicates that SEQ ID NO:15 showed the most homology, i.e., about 42% identity, with a chitinase protein from *Anopheles gambiae* (GenBank accession number 2654602). Comparison of nucleic acid sequence SEQ ID NO:17 with nucleic acid sequences reported in GenBank indicates that SEQ ID NO:17 showed the most homology, i.e., about 58% identity between SEQ ID NO:17 and *Chelonus* sp. venom chitinase mRNA (GenBank accession number U10422).

Example 9

This example describes the purification of a 60-kD protein that binds to IgE from dogs known to be allergic to mite allergens and partial amino acid sequences derived from this 60-kD protein.

A. Purification of a 60 kD Protein

*D. farinae* extract was prepared and fractionated on a Sephacryl S-100 column according to the methods described above in Example 1. Fractions were collected from the Sephacryl S-100 column after the excluded peak (fractions 29 through 35) and were pooled. The pooled fractions were then diluted 1:1 with 10 mM Tris-HCl, pH 8, and applied to a Q-sepharose column and fractions obtained using the methods described above in Example 1. The fraction that eluted in 0.4 M Tris-HCl was concentrated and further purified through a TMS 250 reverse phase HPLC column using the methods described above in Example 1. The proteins in the fractions were resolved by 14% Tris-glycine SDS-PAGE using similar methods described for resolution of proteins on the 12% gel in Example 1. The stained gel is shown in FIG. 2. A protein was identified having a molecular weight of about 60 kD (FIG. 2, lane 4) of about 90% purity that eluted at about 50% B (0.05% TA in 90% acetonitrile). The molecular weight of the denoted 60-kd protein was estimated to be 56.11 kd using the BioRad Multi-Analyst/PC Version 1.1 program and Mark-12 protein molecular weight markers. The about 60-kd protein is referred to herein as mapD protein.

B. Partial N-Terminal and Internal Sequence Obtained from the 60-kd Protein

The eluted protein from Part A, above, was blotted onto PVDF, which was stained with Coomassie R-250 and destained using standard procedures. The protein corresponding to the about 60-kd band was excised and subjected to N-terminal amino acid sequencing using techniques known to those skilled in the art. A partial N-terminal amino acid sequence of about 25 amino acids was deduced for the protein and the amino acid sequence, represented herein as SEQ ID NO:23, was determined to be: Xaa Leu Glu Pro Lys Thr Val Cys Tyr Tyr Glu Ser Trp Val His His Arg Gln Gly Glu Gly Lys Met Asp Pro (wherein Xaa refers to any amino acid).

The protein corresponding to the 60 kd region was also submitted to proteolytic cleavage in order to obtain internal amino acid sequence data. Digestion of the 60-kd protein and reverse-phase chromatography were carried out as described in Example 1. Four proteolytic fragments were isolated and sequenced, and are referred to herein as map(13), map(14), map(15), and map(16).

The N-terminal partial amino acid sequence of map(13) was determined to be Gln Tyr Gly Val Thr Gln Ala Val Val Thr Gln ProAla, also denoted SEQ ID NO:29. The N-terminal partial amino acid sequence of map(14) was determined to be Asp Glu Leu Leu Met Lys Ser Gly Pro Gly Pro, also denoted SEQ ID NO:30. The N-terminal partial amino acid sequence of map(15) was determined to be Asp Met Glu His Phe Thr Gln His Lys Gly Asn Ala Lys Ala Met Ile Ala Val Gly Gly Ser Thr Met Ser, also denoted SEQ ID NO:31. The N-terminal partial amino acid sequence of map(16) was determined to be Asp Ala Asn Glu Glu Ala Arg Ser Gln Leu Pro Glu Thr Ala Met Val Leu Ile Lys Ser Gln, denoted SEQ ID NO:32.

Example 10

This example describes the isolation and sequencing of nucleic acid molecules encoding a portion of the *D. farinae* 60 kD (mapD) allergen.

A *D. farinae* library was prepared as described previously in Example 8. A degenerate synthetic oligonucleotide primer was designed from the N-terminal amino acid sequence deduced for *D. farinae* 60 kD-protein (SEQ ID NO:23): Primer 1, a sense primer corresponding to amino acid residues from about 3 through about 11 of SEQ ID NO:23 has the sequence 5' GAACCAAAA CHGTNTGYTA YTAYG 3', also known as SEQ ID NO:46, where H represents A or C or T, N represents A or C or G or T, and Y represents C or T. PCR amplification of fragments from the *D. farinae* library was conducted using standard techniques. A PCR amplification product was generated using a combination of SEQ ID NO:46 (primer 1) and the M13 forward universal primer 5'GTAAAACGACG GCCAGT 3', denoted SEQ ID NO:47.

A second, nested PCR reaction was carried out on the products of the first PCR reaction. A synthetic oligonucleotide was synthesized that corresponded to a region spanning from about amino acid residue 1 through amino acid residue 10 of the 60-kD protein internal amino acid sequence, SEQ ID NO:31. This primer, primer 2, has the nucleic acid sequence 5' GATATGGAAC ATTTYACHCA ACAYAARGG 3', denoted SEQ ID NO:48, where R represents A or G. A PCR amplification product was generated using the combination of primer 2, SEQ ID NO:48, and the T7 standard primer, 5' GTAATACGAC TCACTATAGG GC 3', denoted SEQ ID NO:49. The resultant PCR product was subjected to DNA sequence analysis using standard techniques.

The PCR product was sequenced and found to contain 510 nucleotides, and is known as $nDerf60_{510}$. The nucleotide sequence of the coding strand of $nDerf60_{510}$ is represented herein as SEQ ID NO:43, and its complement is denoted SEQ ID NO:45. Translation of SEQ ID NO:43 suggests that $nDerf60_{510}$ encodes a partial *D. farinae* 60-kD protein of about 170 amino acids, referred to herein as $PDerf60_{170}$, with an amino acid sequence denoted SEQ ID NO:44, assuming an open reading frame in which the first codon spans from about nucleotide 1 through nucleotide 3 of SEQ ID NO:43, and the last codon spanning from about nucleotide 508 through about nucleotide 510 of SEQ ID NO:43. $PDerf60_{170}$ has an estimated molecular weight of 19.2 kD and an estimated pI of about 6.51.

Nucleic acid molecule $nDerf60_{510}$ was used as a probe to isolate a nucleic acid molecule that encodes a protein corresponding to a full-length, or larger partial *D. farinae* 60-kD protein. Using procedures described previously in Example 8, the whole *D. farinae* library was screened with the nucleic acid SEQ ID NO:43 radiolabeled with $^{32}P$ using standard techniques. Hybridization was done in 6×SSC, 5× Denhardt's solution, 0.5% SDS, 100 mg/ml ssDNA, at 55° C., for about 36 hours. The filters were washed 3 times, for 30 minutes per wash, at 55° C. in 2×SSC, 0.2% SDS, followed by a final wash of about 30 minutes in 0.2×SSC, 0.2% SDS.

PCR amplification was carried out on the primary phage plugs. Primer 1, denoted as SEQ ID NO:46, and T7 standard primer, denoted as SEQ ID NO:49, were used as the primers, and a PCR product was generated. Preliminary sequence analysis of this 1.6 kilobase PCR product showed that it represents a nucleic acid sequence that contains the complete sequence encoding the PDerf60 full-length protein.

Comparison of $PDerf60_{170}$, the amino acid sequence of SEQ ID NO:44, with amino acid sequences reported in GenBank indicates that $PDerf60_{170}$ showed the most homology, i.e. about 39% identity, with a chitinase protein precursor from *Aphanodidium album*. (GenBank accession number P32470). Nucleic acid sequence SEQ ID NO:43 showed no significant homology to any of the sequences submitted to GenBank.

Example 11

This example describes the isolation of nucleic acid molecules encoding *Dermatophagoides pteronyssius* 98 kD allergen protein.

Nucleic acid molecules with high homology to the *D. farinae* 98 kD allergen (map B) were isolated from a *D. pteronyssius* cDNA library by hybridization with a 32-P labeled cDNA encoding the *D. farinae* HMW-map composition.

A *D. pteronyssius* cDNA library was prepared as follows. Total RNA was extracted from approximately 2 grams of *D. pteronyssius* mites, using an acid-guanidium-phenol-chloroform method, described by Chomzynski et al., 1987, *Anal. Biochem* 162: pp 156-159. Poly A+ selected RNA was separated from the total RNA preparation by oligo-dT cellulose chromatography using the mRNA Purification Kit (available from Pharmacia, Newark, N.J.), according to the method recommended by the manufacturer. A whole *D. pteronyssius* cDNA library was constructed in lambda-Uni-ZAP™ XR vector (available from Stratagene, La Jolla, Calif.), using Stratagene's ZAP-cDNA Synthesis Kit protocol. Approximately 5 milligram (mg) of Poly A+ RNA was used to produce the *D. pteronyssius* cDNA library.

Using a modification of the protocol described in the cDNA Synthesis Kit (available from Stratagene), the whole *D. pteronyssius* cDNA library was screened, using duplicate plaque lifts, with a 32P-labeled cDNA encoding the *D. farinae* 97 kD Map B allergen, i.e. SEQ ID NO:17. Hybridization was done in 6×SSC (for recipe see Sambrook, et al., ibid.), 5× Denhardt's solution (for recipe see Sambrook, et al., ibid.), 0.5% sodium dodecyl sulfate (SDS) (available from Sigma), and 100 mg/ml of single stranded DNA (available from Sigma), at 55° C., for about 36 hours. The filters were washed 3 times, for about 30 minutes per wash, at 55° C., in 2×SSC, 0.2% SDS, followed by a final wash of about 30 minutes, at 55° C., in 0.2×SSC, 0.2% SDS. A plaque purified clone of the *D. pteronyssius* nucleic acid molecule encoding the *D. pteronyssius* 97 kD allergen (map B) was converted into a double stranded recombinant molecule using the ExAssist™ helper phage and SOLR™ *E. coli* according to the in vivo excision protocol described in the ZAP-cDNA Synthesis Kit (all available from Stratagene). The plasmid containing the *D. pteronyssius* clone was subjected to DNA sequence analysis using standard techniques. DNA sequence analysis, including the determination of molecular weight and isoelectric point (pI) was performed using the GCG™ program.

A clone was isolated that included an about 1621-nucleotide insert, which includes the full-length coding region, referred to herein as $nDerp98_{1621}$, with a coding strand represented as SEQ ID NO:34 and a complementary strand represented as SEQ ID NO:36. The apparent start and stop codons span from nucleotide 14 through nucleotide 16, and from nucleotide 1541 through nucleotide 1543, respectively, of SEQ ID NO:34. A putative polyadenylation signal (5' AATAAA 3') is located in a region spanning from nucleotide 1584 to 1589 of SEQ ID NO:34.

Translation of SEQ ID NO:34 yields a protein of about 509 amino acids, denoted $PDerp98_{509}$, the amino acid sequence of which is presented as SEQ ID NO:35. The nucleic acid molecule consisting of the coding region encoding $PDerp98_{509}$ is referred to herein as $nDerp98_{1527}$, the nucleic acid sequence of which is represented as SEQ ID NO:37 (the coding strand), and SEQ ID NO:39 (the complementary strand). The amino acid sequence of $PDerp98_{509}$, also represented herein as SEQ ID NO:38, has an estimated molecular weight of about 58.9 kD and an estimated pI of about 5.61. Analysis of $PDerp98_{509}$ suggests the presence of a signal peptide spanning from about amino acid 1 through about amino acid 19. The proposed mature protein, denoted herein as $PDerp98_{490}$, contains about 490 amino acids, and is represented herein as SEQ ID NO:41. The amino acid sequence of $PDerp98_{490}$ predicts the protein to have an estimated molecular weight of about 56.8 kD, and an estimated pI of about 5.49, as well as two asparagine-linked glycosylation sites extending from about amino acid 115 to about amino acid 117, and extending from about amino acid 240 to amino acid 242, respectively. The nucleic acid molecule encoding $PDerp98_{490}$ is known as $nDerp98_{1470}$, with a coding strand represented by SEQ ID NO:40 and a complementary strand represented by SEQ ID NO:42.

A BLAST search was performed as described previously. $PDerp98_{509}$, SEQ ID NO:35, showed the highest homology at the amino acid level with the *Manduca sexta* chitinase (SwissProt accession number p36362), with about a 34% identity. $nDerp98_{1621}$, SEQ ID NO:34, showed the highest homology at the nucleic acid level to *Chelonus* sp. chitinase (accession number U10422), with about a 49% identity. Comparison of cDNA regions corresponding to the coding regions for the *D. farinae* 98 kD allergen protein and the cDNA regions corresponding to the coding regions for the *D. pteronyssius* 98 kD allergen protein shows an identity of about 84%.

Example 14

This example demonstrates the binding of the *D. farinae* HMW-map composition to human IgE in human sera isolated from humans known to be allergic to mite allergens.

A technique called RAST, or radio-allergo-absorbent test, was used because the amount of human IgE present in human sera is quite low. RAST was essentially performed as described in Aalberse, R C et al., (1981) *J. Allergy Clin Immun.* 68: pp 356-364. To calculate the unit IU/ml, a standard curve was derived by performing RAST with several dilutions of a well-characterized chimeric human/mouse IgE monoclonal antibody against Derp2, (human IgE/monoclonal anti-Derp2, following the procedure of Schuurman, et al. (1997) *J Allergy Clin Immunol.* 99: pp 545-550).

Briefly, 50 μg of the HMW-map composition, purified as described in Example 1, was coupled to 50 mg of CNBr-activated Sepharose 4B (available from Pharmacia, Piscataway, N.J.), according to the manufacturer's protocols. Human sera were selected (17 different samples, total) on the basis of a positive RAST for whole mite *D. farinae* extracts, a positive RAST number is greater than 1 IU/ml). Two negative (less than 0.3 IU) control sera were also included.

To test each individual serum sample, 0.5 mg of the *D. farinae* HMW-map composition-coupled Sepharose was incubated with 50 μl serum in a total volume of 300 μl of PBS-T (Phosphate buffered saline with added 0.1% volume/volume Tween-20, available from Sigma). Incubation was overnight at 27° C., with shaking. After incubation, the coupled Sepharose was washed five times with PBS-T. Radiolabelled ($^{125}$-Iodine) sheep anti-human IgE, made by standard radioiodination protocols, (diluted in PBS-T with 4.5% bovine serum and 0.5% sheep serum, v/v) in a total volume of 750 μl, was added and incubated overnight at 27° C. After incubation, the coupled Sepharose was washed four times with PBS-T and counted in a gamma-counter to determine the amount of radiolabeled sheep anti-human IgE bound to the HMW-map composition-coupled Sepharose. The results are shown in Table 4.

TABLE 4

Binding of human IgE to HMW-map composition from *D. farinae*

| Serum number | RAST, *D. farinae* whole extract, IU | RAST, HMW-map comps'n., IU |
| --- | --- | --- |
| 1445 | >100 | 48 |
| 1456 | >100 | 42 |
| 1458 | 21.1 | 0.5 |
| 1460 | 14.1 | 2.5 |
| 1463 | 37.6 | 0.1 |
| 1464 | 37.2 | 2.0 |
| 1465 | 14.5 | 0.7 |
| 1466 | 89.9 | 7.7 |
| 1468 | >100 | 19.9 |
| 1471 | 31.9 | 0.8 |
| 1491 | 23.8 | 1.0 |
| 1496 | 25.3 | 3.6 |
| 1505 | 5.1 | 0.2 |
| 1523 | 1.0 | <0.1 |

TABLE 4-continued

Binding of human IgE to HMW-map composition from *D. farinae*

| Serum number | RAST, *D. farinae* whole extract, IU | RAST, HMW-map comps'n., IU |
|---|---|---|
| 1529 | 1.2 | 0.7 |
| 1530 (control) | 0.2 | <0.1 |
| 1531 (control) | 0.1 | <0.1 |

Almost 75% of patients (11 of 15) who showed sensitivity to *D. farinae* whole mite extracts were sensitive to the HMW-map composition antigen, implying that the HMW-map composition antigen is a major antigen for *D. farinae* sensitive humans. Sensitivity to the HMW-map composition was defined as a RAST of greater than or e to 0.5 IU.

Example 15

This example demonstrates that the *D. farinae* HMW-map composition des in Example 1 includes a glycoprotein.

About (5.4 µg) of a *D. farinae* HMW-map composition prepared in accordance with Example 1 was applied to SDS PAGE and electrophoresis was done according to standard techniques. The protein was blotted to a nitrocellulose membrane according to standard techniques, and glycoprotein was detected using the DIG™ Glycine Detection Kit (available from Boehringer Mannheim, Indianapolis, Ind.), using the manufacturer's protocol. The region corresponding to the HMW-map region showed a positive reaction with the kit, indicating that the HMW-map composition includes a glycoprotein.

Example 16

This example shows that the *D. farinae* HMW-map composition retains its character as an allergen even when the amino acid residues are removed, both by chemical and enzymatic means. The results suggest that the main epitope(s) could be a carbohydrate epitope including a polysaccharide attached to an N-linked or O-linked glycosylation site on the HMW-map composition.

A. Protein Elimination by Chemical Means (β-Elimination of Proteins)

Twelve µg (microgram) of HMW-map composition (purified as described in Example 1) was dissolved in 100 µl (microliter) of distilled deionized water. To this mixture was added 5 µl 10 M (molar) NaOH and 3.8 mg (milligram) NaBH$_4$ (available from Sigma) to give a final concentration of 0.5 M NaOH and 1 M NaBH$_4$. This reaction mixture was heated at 50° C. for 30 minutes, then cooled, and 100 µl acetone was added. To this mixture, sufficient amount, i.e. approximately 150 µl, of Dowex 50 (H+) (available from Pharmacia) was added to make the solution slightly acidic. The Dowex 50 adsorbed and removed the protein, leaving any sugar moieties in the supernatant. The mixture was centrifuged in a microcentrifuge and washed three times with 100 µl of water. The combined supernatants from the centrifugations were evaporated to dryness, then washed five times from a methanol:HCl solution (1000:1 v/v), evaporating to dryness after each wash, to remove salts. The mixture was dissolved in 100 µl of water, and a portion (20 µl) was analyzed by SDS-PAGE using standard techniques, and both Coomassie blue and Silver staining were used to determine the amount of protein in the chemically treated samples. No protein was detected by either Coomassie or Silver staining, indicating removal of protein. Any sugar moieties on the protein would be unaffected by these conditions.

The remainder of the residue from each sample was subjected to ELISA analysis as described in Example 4. Briefly, 100 ng of either the β-eliminated sample or of non-β-eliminated sample of the HMW-map composition was coated onto the Immulon plates, and ELISAs were carried out as described in Example 4 with a *D. farinae* sensitive dog sera pool, a *D. farinae* sensitive cat sera pool, and various individual dog sera that are either *D. farinae* sensitive or not sensitive (as measured by ELISA). The results are shown in Table 5.

TABLE 5

Reactivity of dog and cat sera to HMW-map composition and to β-eliminated HMW-map composition (which is carbohydrate only)

| Sera used | β-eliminated HMW-map, OD (carbohydrate antigen) | untreated HMW-map comps'n., OD × 10$^{-3}$ |
|---|---|---|
| *D. farinae* dog pool | 1233 | 1931 |
| *D. farinae* cat pool | 2837 | 3115 |
| dog 1621A | 15 | 0 |
| dog 1621C | 24 | 21 |
| dog 1621S | 59 | 420 |
| dog 1626C | 23 | 214 |
| dog SPF-2 | 16 | 0 |

Results from Table 5 indicate that the β-eliminated HMW-map composition sample still retains the ability to bind IgE from dog and cat sera that is sensitive to *D. farinae* HMW-map composition, indicating that the glycans attached to the protein constitute a major epitope of the HMW-map composition allergen protein.

B. Protein Elimination by Enzymatic Means.

14 µg of HMW-map composition (purified as described in Example 1) was digested with 1 µg Endoproteinase K, available from Sigma, to remove the protein moiety of the molecule. The digestion reaction took place at 56° C. for 24 hours, after which the endoproteinase in the reaction was heat-denatured in boiling water for 10 minutes.

A portion of this reaction was analyzed by SDS-PAGE using standard techniques, and both Coomassie blue and Silver staining were used to detect the presence of protein in the enzymatically digested samples. No HMW-map composition was detected by either Coomassie or Silver staining, indicating elimination of the HMW-map composition. Any glycan that was attached via a glycosylation site on the protein would be unaffected by these conditions.

The remainder of the enzymatically digested reaction was tested by ELISA in the manner described in Example 4. Briefly, 100 ng of either the proteinase-K-digested sample or of a non-digested sample of the HMW-map composition was coated onto Immulon plates, and ELISAs were carried out as described in Example 4 with various individual dog sera that were either *D. farinae* sensitive or not sensitive (as measured by ELISA). The results are shown in Table 6.

TABLE 6

Reactivity of dog sera to HMW-map composition and to Endoproteinase-K digested HMW-map composition.

| dog # | D. farinae sensitive?[1] | OD, wells coated with HMW-map comps'n. | OD, wells coated with Proteinase K digested HMW-map |
|---|---|---|---|
| 1 | yes | 120 | 122 |
| 2 | yes | 1637 | 1561 |
| 3 | yes | 858 | 383 |
| 4 | yes | 914 | 509 |
| 5 | yes | 277 | 227 |
| 6 | yes | 2891 | 2636 |
| 7 | no | 10 | 11 |
| 8 | yes | 4056 | 3880 |
| 9 | yes | 1920 | 1626 |
| 10 | yes | 472 | 432 |
| 11 | yes | 328 | 213 |
| 12 | yes | 2913 | 2530 |
| 13 | yes | 1232 | 984 |
| 14 | yes | 3153 | 2355 |
| 15 | no | 6 | 46 |
| 16 | yes | 860 | 339 |
| 17 | yes | 2429 | 750 |
| 18 | yes | 1194 | 351 |
| 19 | yes | 2655 | 1443 |
| 20 | yes | 3285 | 1207 |
| 21 | yes | 2636 | 1240 |
| 22 | yes | 1097 | 848 |
| 23 | yes | 1621 | 1408 |
| 24 | yes | 2113 | 1592 |
| 25 | yes | 1169 | 408 |
| 26 | yes | 4200 | 4200 |
| 27 | yes | 4200 | 4200 |
| 28 | yes | 3222 | 2932 |
| 29 | yes | 2468 | 2118 |
| 30 | yes | 3339 | 2454 |
| 31 | no | 0 | 4 |

[1] by ELISA in a separate experiment

Results from Table 6 indicate that the proteinase-K digested HMW-map composition sample still retains the ability to bind IgE from dog and cat sera that is sensitive to D. farinae HMW-map composition, suggesting that the glycans attached to the protein constitute a major epitope on the HMW-map composition.

Example 17

This example describes attempts to remove N-linked glycans from the HMW-map composition.

HMW-map composition (2 µg), purified as in Example 1, was digested with N-glycosidase F (available from Boehringer-Mannheim), according to the manufacturer's directions. The digestion was analyzed by SDS-PAGE and stained according to standard protocols. 2 µg Fetuin (available from Sigma) was used as a positive N-linked glycosylated protein control. Analysis of the SDS-PAGE showed that there were no apparent differences in the molecular weights of the intact and digested map B protein. The positive control, fetuin, did show a reduction of molecular weight after digestion with N-glycosidase F. This result indicates that there are no N-linked glycans on the HMW-map composition, or alternatively that there are only small sized N-glycans on the HMW-map composition.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein comprising the amino acid sequence of SEQ TD NO:35, SEQ ID NO:38, or SEQ ID NO:41.

2. An isolated protein consisting of the amino acid sequence of SEQ ID NO:35, SEQ ID NO:38, or SEQ ID NO:41.

3. A fragment of the isolated protein of claim 2, wherein said fragment is at least 35 residues in length.

4. A fragment of the isolated protein of claim 2, wherein said fragment is at least 50 residues in length.

5. A fragment of the isolated protein of claim 2, wherein said fragment is at least 100 residues in length.

* * * * *